(12) United States Patent
Santrock et al.

(10) Patent No.: US 12,310,603 B2
(45) Date of Patent: May 27, 2025

(54) SYSTEM AND TECHNIQUE FOR METATARSAL REALIGNMENT WITH REDUCED INCISION LENGTH

(71) Applicant: Treace Medical Concepts, Inc., Ponte Vedra, FL (US)

(72) Inventors: Robert D. Santrock, Morgantown, WV (US); Paul Dayton, Ankeny, IA (US); Daniel J. Hatch, Greeley, CO (US); W. Bret Smith, Durango, CO (US); Carlos Eduardo Gil, Memphis, TN (US); Sean F. Scanlan, Jacksonville, FL (US); Joe W. Ferguson, Ponte Vedra Beach, FL (US); John T. Treace, Ponte Vedra Beach, FL (US); Tyler Hissong, Jacksonville, FL (US); Jason May, St. John's, FL (US); William DeCarbo, Pittsburgh, PA (US); Jody McAleer, Jefferson City, MO (US)

(73) Assignee: Treace Medical Concepts, Inc., Ponte Vedra, FL (US)

( * ) Notice: Subject to any disclaimer, the term of this patent is extended or adjusted under 35 U.S.C. 154(b) by 390 days.

(21) Appl. No.: 17/674,447

(22) Filed: Feb. 17, 2022

(65) Prior Publication Data
US 2022/0257267 A1 Aug. 18, 2022

Related U.S. Application Data

(60) Provisional application No. 63/151,041, filed on Feb. 18, 2021.

(51) Int. Cl.
*A61B 17/17* (2006.01)
*A61B 17/88* (2006.01)

(52) U.S. Cl.
CPC ...... *A61B 17/1775* (2016.11); *A61B 17/1728* (2013.01); *A61B 17/88* (2013.01)

(58) Field of Classification Search
CPC .. A61B 17/1775; A61B 17/1728; A61B 17/88
See application file for complete search history.

(56) References Cited

U.S. PATENT DOCUMENTS

| 3,584,667 A | 6/1971 | Reiland |
|---|---|---|
| 3,664,022 A | 5/1972 | Small |

(Continued)

FOREIGN PATENT DOCUMENTS

| AU | 2009227957 B2 | 7/2014 |
|---|---|---|
| CA | 2491824 A1 | 9/2005 |

(Continued)

OTHER PUBLICATIONS

"Lag Screw Target Bow," Stryker Leibinger GmbH & Co. KG, Germany 2004, 8 pages.

(Continued)

*Primary Examiner* — Sameh R Boles
(74) *Attorney, Agent, or Firm* — Fredrikson & Byron, P.A.

(57) ABSTRACT

A metatarsal correction procedure may be performed so as to minimize the length of the surgical incision created during the procedure. A variety of different instruments and/or techniques and facilitate the minimal incision procedure. In some examples, a technique involves making a comparatively small surgical incision to access a tarsometatarsal joint. A metatarsal and a cuneiform separated by the tarsometatarsal joint can be prepared. In addition, the metatarsal can be moved relative to the cuneiform using a bone positioning device having a metatarsal engagement member positioned in contact with the skin of the patient on a medial side of the metatarsal. After moving the metatarsal, a fixa- (Continued)

tion device can be installed across the tarsometatarsal joint to cause fusion. In some examples, a plate holder is attached to a U-shaped bone plate to facilitate plating across the joint through the comparatively small incision.

24 Claims, 21 Drawing Sheets

(56) References Cited

U.S. PATENT DOCUMENTS

| | | |
|---|---|---|
| 3,835,858 A | 9/1974 | Hagen |
| 4,069,824 A | 1/1978 | Weinstock |
| 4,159,716 A | 7/1979 | Borchers |
| 4,187,840 A | 2/1980 | Watanabe |
| 4,197,889 A | 4/1980 | Peterson |
| 4,335,715 A | 6/1982 | Kirkley |
| 4,338,927 A | 7/1982 | Volkov et al. |
| 4,349,018 A | 9/1982 | Chambers |
| 4,409,973 A | 10/1983 | Neufeld |
| 4,440,168 A | 4/1984 | Warren |
| 4,501,268 A | 2/1985 | Comparetto |
| 4,502,474 A | 3/1985 | Comparetto |
| 4,509,511 A | 4/1985 | Neufeld |
| 4,565,191 A | 1/1986 | Slocum |
| 4,570,624 A | 2/1986 | Wu |
| 4,627,425 A | 12/1986 | Reese |
| 4,628,919 A | 12/1986 | Clyburn |
| 4,632,102 A | 12/1986 | Comparetto |
| 4,664,102 A | 5/1987 | Comparetto |
| 4,708,133 A | 11/1987 | Comparetto |
| 4,736,737 A | 4/1988 | Fargie et al. |
| 4,750,481 A | 6/1988 | Reese |
| 4,754,746 A | 7/1988 | Cox |
| 4,757,810 A | 7/1988 | Reese |
| 4,895,141 A | 1/1990 | Koeneman et al. |
| 4,952,214 A | 8/1990 | Comparetto |
| 4,959,066 A | 9/1990 | Dunn et al. |
| 4,978,347 A | 12/1990 | Ilizarov |
| 4,988,349 A | 1/1991 | Pennig |
| 4,995,875 A | 2/1991 | Coes |
| 5,021,056 A | 6/1991 | Hofmann et al. |
| 5,035,698 A | 7/1991 | Comparetto |
| 5,042,983 A | 8/1991 | Rayhack |
| 5,049,149 A | 9/1991 | Schmidt |
| 5,053,039 A | 10/1991 | Hofmann et al. |
| 5,078,719 A | 1/1992 | Schreiber |
| 5,112,334 A | 5/1992 | Alchermes et al. |
| 5,147,364 A | 9/1992 | Comparetto |
| 5,176,685 A | 1/1993 | Rayhack |
| 5,207,676 A | 5/1993 | Canadell et al. |
| 5,246,444 A | 9/1993 | Schreiber |
| 5,254,119 A | 10/1993 | Schreiber |
| 5,312,412 A | 5/1994 | Whipple |
| 5,358,504 A | 10/1994 | Paley et al. |
| 5,364,402 A | 11/1994 | Mumme et al. |
| 5,374,271 A | 12/1994 | Hwang |
| 5,413,579 A | 5/1995 | Tom Du Toit |
| 5,417,694 A | 5/1995 | Marik et al. |
| 5,449,360 A | 9/1995 | Schreiber |
| 5,470,335 A | 11/1995 | Du Toit |
| 5,490,854 A | 2/1996 | Fisher et al. |
| 5,529,075 A | 6/1996 | Clark |
| 5,540,695 A | 7/1996 | Levy |
| 5,578,038 A | 11/1996 | Slocum |
| 5,586,564 A | 12/1996 | Barrett et al. |
| 5,601,565 A | 2/1997 | Huebner |
| 5,613,969 A | 3/1997 | Jenkins, Jr. |
| 5,620,442 A | 4/1997 | Bailey et al. |
| 5,620,448 A | 4/1997 | Puddu |
| 5,643,270 A | 7/1997 | Combs |
| 5,667,510 A | 9/1997 | Combs |
| H0001706 H | 1/1998 | Mason |
| 5,722,978 A | 3/1998 | Jenkins, Jr. |
| 5,749,875 A | 5/1998 | Puddu |
| 5,779,709 A | 7/1998 | Harris, Jr. et al. |
| 5,788,695 A | 8/1998 | Richardson |
| 5,803,924 A | 9/1998 | Oni et al. |
| 5,810,822 A | 9/1998 | Mortier |
| 5,843,085 A | 12/1998 | Graser |
| 5,893,553 A | 4/1999 | Pinkous |
| 5,911,724 A | 6/1999 | Wehrli |
| 5,935,128 A | 8/1999 | Carter et al. |
| 5,941,877 A | 8/1999 | Viegas et al. |
| 5,951,556 A | 9/1999 | Faccioli et al. |
| 5,980,526 A | 11/1999 | Johnson et al. |
| 5,984,931 A | 11/1999 | Greenfield |
| 6,007,535 A | 12/1999 | Rayhack et al. |
| 6,027,504 A | 2/2000 | Mcguire |
| 6,030,391 A | 2/2000 | Brainard et al. |
| 6,149,653 A | 11/2000 | Deslauriers |
| 6,162,223 A | 12/2000 | Orsak et al. |
| 6,171,309 B1 | 1/2001 | Huebner |
| 6,203,545 B1 | 3/2001 | Stoffella |
| 6,248,109 B1 | 6/2001 | Stoffella |
| 6,391,031 B1 | 5/2002 | Toomey |
| 6,416,465 B2 | 7/2002 | Brau |
| 6,478,799 B1 | 11/2002 | Williamson |
| 6,511,481 B2 | 1/2003 | Von Hoffmann et al. |
| 6,547,793 B1 | 4/2003 | Mcguire |
| 6,676,662 B1 | 1/2004 | Bagga et al. |
| 6,719,773 B1 | 4/2004 | Boucher et al. |
| 6,743,233 B1 | 6/2004 | Baldwin et al. |
| 6,755,838 B2 | 6/2004 | Trnka |
| 6,796,986 B2 | 9/2004 | Duffner |
| 6,859,661 B2 | 2/2005 | Tuke |
| 6,964,645 B1 | 11/2005 | Smits |
| 7,018,383 B2 | 3/2006 | Mcguire |
| 7,033,361 B2 | 4/2006 | Collazo |
| 7,097,647 B2 | 8/2006 | Segler |
| 7,112,204 B2 | 9/2006 | Justin et al. |
| 7,153,310 B2 | 12/2006 | Ralph et al. |
| 7,182,766 B1 | 2/2007 | Mogul |
| 7,225,710 B2 | 6/2007 | Pacheco, Jr. |
| 7,241,298 B2 | 7/2007 | Nemec et al. |
| 7,282,054 B2 | 10/2007 | Steffensmeier et al. |
| 7,377,924 B2 | 5/2008 | Raistrick et al. |
| 7,465,303 B2 | 12/2008 | Riccione et al. |
| 7,540,874 B2 | 6/2009 | Trumble et al. |
| 7,572,258 B2 | 8/2009 | Stiernborg |
| 7,641,660 B2 | 1/2010 | Lakin et al. |
| D610,257 S | 2/2010 | Horton |
| 7,686,811 B2 | 3/2010 | Byrd et al. |
| 7,691,108 B2 | 4/2010 | Lavallee |
| 7,763,026 B2 | 7/2010 | Egger et al. |
| D629,900 S | 12/2010 | Fisher |
| 7,875,058 B2 | 1/2011 | Holmes, Jr. |
| 7,922,749 B2 | 4/2011 | Dewey |
| 7,967,823 B2 | 6/2011 | Ammann et al. |
| 7,972,338 B2 | 7/2011 | O'Brien |
| D646,389 S | 10/2011 | Claypool et al. |
| 8,057,478 B2 | 11/2011 | Kuczynski et al. |
| 8,062,301 B2 | 11/2011 | Ammann et al. |
| D651,315 S | 12/2011 | Bertoni et al. |
| D651,316 S | 12/2011 | May et al. |
| 8,080,010 B2 | 12/2011 | Schulz et al. |
| 8,080,045 B2 | 12/2011 | Wotton, III |
| 8,083,746 B2 | 12/2011 | Novak |
| 8,123,753 B2 | 2/2012 | Poncet |
| 8,137,406 B2 | 3/2012 | Novak et al. |
| 8,147,530 B2 | 4/2012 | Strnad et al. |
| 8,167,918 B2 | 5/2012 | Strnad et al. |
| 8,172,848 B2 | 5/2012 | Tomko et al. |
| 8,182,187 B2 | 5/2012 | Siong |
| 8,192,441 B2 | 6/2012 | Collazo |
| 8,197,487 B2 | 6/2012 | Poncet et al. |
| 8,231,623 B1 | 7/2012 | Jordan |
| 8,231,635 B2 | 7/2012 | Sharifi-Mehr et al. |
| 8,231,663 B2 | 7/2012 | Kay et al. |
| 8,236,000 B2 | 8/2012 | Ammann et al. |
| 8,246,561 B1 | 8/2012 | Agee et al. |
| D666,721 S | 9/2012 | Wright et al. |
| 8,262,664 B2 | 9/2012 | Justin et al. |
| 8,277,459 B2 | 10/2012 | Sand et al. |

(56) References Cited

U.S. PATENT DOCUMENTS

| | | |
|---|---|---|
| 8,282,644 B2 | 10/2012 | Edwards |
| 8,282,645 B2 | 10/2012 | Lawrence et al. |
| 8,292,966 B2 | 10/2012 | Morton |
| 8,303,596 B2 | 11/2012 | Plaky et al. |
| 8,313,492 B2 | 11/2012 | Wong et al. |
| 8,323,289 B2 | 12/2012 | Re |
| 8,337,503 B2 | 12/2012 | Lian |
| 8,343,159 B2 | 1/2013 | Bennett |
| 8,377,105 B2 | 2/2013 | Bscher |
| D679,395 S | 4/2013 | Wright et al. |
| 8,409,209 B2 | 4/2013 | Ammann et al. |
| 8,435,246 B2 | 5/2013 | Fisher et al. |
| 8,459,155 B2 | 6/2013 | Canizares, Jr. et al. |
| 8,475,462 B2 | 7/2013 | Thomas et al. |
| 8,496,662 B2 | 7/2013 | Novak et al. |
| 8,518,045 B2 | 8/2013 | Szanto |
| 8,523,870 B2 | 9/2013 | Green, II et al. |
| 8,529,571 B2 | 9/2013 | Horan et al. |
| 8,540,777 B2 | 9/2013 | Ammann et al. |
| 8,545,508 B2 | 10/2013 | Collazo |
| D694,884 S | 12/2013 | Mooradian et al. |
| D695,402 S | 12/2013 | Dacosta et al. |
| 8,652,141 B2 | 2/2014 | Rush et al. |
| 8,652,142 B2 | 2/2014 | Geissler |
| 8,657,820 B2 | 2/2014 | Kubiak et al. |
| D701,303 S | 3/2014 | Cook |
| 8,672,945 B2 | 3/2014 | Lavallee et al. |
| 8,696,716 B2 | 4/2014 | Kartalian et al. |
| 8,696,719 B2 | 4/2014 | Lofthouse et al. |
| 8,702,715 B2 | 4/2014 | Ammann et al. |
| D705,929 S | 5/2014 | Frey |
| 8,715,363 B2 | 5/2014 | Ratron et al. |
| 8,728,084 B2 | 5/2014 | Berelsman et al. |
| 8,758,354 B2 | 6/2014 | Habegger et al. |
| 8,764,760 B2 | 7/2014 | Metzger et al. |
| 8,764,763 B2 | 7/2014 | Wong et al. |
| 8,771,279 B2 | 7/2014 | Philippon et al. |
| 8,777,948 B2 | 7/2014 | Bernsteiner |
| 8,777,960 B2 | 7/2014 | Murray et al. |
| 8,784,427 B2 | 7/2014 | Fallin et al. |
| 8,784,457 B2 | 7/2014 | Graham |
| 8,795,286 B2 | 8/2014 | Sand et al. |
| 8,801,727 B2 | 8/2014 | Chan et al. |
| 8,808,303 B2 | 8/2014 | Stemniski et al. |
| 8,828,012 B2 | 9/2014 | May et al. |
| 8,858,602 B2 | 10/2014 | Weiner et al. |
| 8,870,876 B2 | 10/2014 | Lettmann et al. |
| 8,882,778 B2 | 11/2014 | Ranft |
| 8,882,816 B2 | 11/2014 | Kartalian et al. |
| 8,888,785 B2 | 11/2014 | Ammann et al. |
| D720,456 S | 12/2014 | Dacosta et al. |
| D720,459 S | 12/2014 | Faux et al. |
| 8,900,247 B2 | 12/2014 | Tseng et al. |
| 8,906,026 B2 | 12/2014 | Ammann et al. |
| 8,945,132 B2 | 2/2015 | Play et al. |
| 8,984,991 B1 | 3/2015 | English |
| 8,998,903 B2 | 4/2015 | Price et al. |
| 8,998,904 B2 | 4/2015 | Zeetser et al. |
| 8,998,921 B2 | 4/2015 | Sharifi-Mehr et al. |
| 9,011,507 B2 | 4/2015 | Schelling |
| 9,023,052 B2 | 5/2015 | Lietz et al. |
| 9,044,250 B2 | 6/2015 | Olsen et al. |
| 9,044,287 B2 | 6/2015 | Reed et al. |
| 9,060,822 B2 | 6/2015 | Wright et al. |
| 9,089,376 B2 | 7/2015 | Medoff et al. |
| 9,101,421 B2 | 8/2015 | Blacklidge |
| 9,107,715 B2 | 8/2015 | Blitz et al. |
| 9,113,920 B2 | 8/2015 | Ammann et al. |
| D738,180 S | 9/2015 | Campbell |
| 9,125,704 B2 | 9/2015 | Reed et al. |
| D740,424 S | 10/2015 | Dacosta et al. |
| 9,345,514 B2 | 5/2016 | Robinson et al. |
| 9,422,965 B2 | 8/2016 | Campbell, II |
| D765,844 S | 9/2016 | Dacosta |
| D766,434 S | 9/2016 | Dacosta |
| D766,437 S | 9/2016 | Dacosta |
| D766,438 S | 9/2016 | Dacosta |
| D766,439 S | 9/2016 | Dacosta |
| 9,433,452 B2 | 9/2016 | Weiner et al. |
| 9,452,057 B2 | 9/2016 | Dacosta et al. |
| 9,504,582 B2 | 11/2016 | Sander et al. |
| 9,522,023 B2 | 11/2016 | Haddad et al. |
| 9,572,605 B2 | 2/2017 | Shipp |
| 9,592,084 B2 | 3/2017 | Grant |
| 9,642,609 B2 | 5/2017 | Holmes, Jr. |
| 9,693,812 B2 | 7/2017 | Zeetser et al. |
| 9,750,538 B2 | 9/2017 | Soffiatti et al. |
| 9,785,747 B2 | 10/2017 | Geebelen |
| 9,814,474 B2 | 11/2017 | Montoya et al. |
| 9,980,760 B2 | 5/2018 | Dacosta et al. |
| 10,022,844 B2 | 7/2018 | Lukes et al. |
| 10,028,750 B2 | 7/2018 | Rose |
| 10,045,807 B2 | 8/2018 | Santrock et al. |
| 10,064,631 B2 | 9/2018 | Dacosta et al. |
| 10,159,499 B2 | 12/2018 | Dacosta et al. |
| 10,159,512 B2 | 12/2018 | Robinson |
| 10,166,055 B2 | 1/2019 | Eekhoff et al. |
| 10,172,645 B2 | 1/2019 | Zeetser et al. |
| 10,271,879 B2 | 4/2019 | May et al. |
| 10,278,692 B2 | 5/2019 | Bruker et al. |
| 10,292,713 B2 | 5/2019 | Fallin et al. |
| 10,292,735 B2 | 5/2019 | Robinson et al. |
| 10,327,823 B2 | 6/2019 | Geldwert |
| 10,327,829 B2 | 6/2019 | Dacosta et al. |
| 10,376,268 B2 | 8/2019 | Fallin et al. |
| 10,470,779 B2 | 11/2019 | Fallin et al. |
| 10,492,834 B2 | 12/2019 | May et al. |
| 10,561,453 B2 | 2/2020 | Rezach et al. |
| 10,582,936 B1 | 3/2020 | Hissong et al. |
| 10,646,263 B2 | 5/2020 | Lamm et al. |
| 10,653,432 B2 | 5/2020 | Luttrell et al. |
| 10,653,455 B2 | 5/2020 | Lehman, Jr. et al. |
| 10,779,867 B2 | 9/2020 | Penzimer et al. |
| 10,786,292 B2 | 9/2020 | Singh et al. |
| 10,856,886 B2 | 12/2020 | Dacosta et al. |
| 10,856,918 B2 | 12/2020 | Dacosta |
| 10,856,925 B1 | 12/2020 | Pontell |
| 10,881,436 B2 | 1/2021 | Muller et al. |
| 10,888,356 B2 | 1/2021 | Beyer |
| 10,939,939 B1 | 3/2021 | Gil et al. |
| 11,020,148 B2 | 6/2021 | Hollis et al. |
| 11,304,705 B2 | 4/2022 | Fallin et al. |
| 2002/0099381 A1 | 7/2002 | Maroney |
| 2002/0107519 A1 | 8/2002 | Dixon et al. |
| 2002/0165552 A1 | 11/2002 | Duffner |
| 2002/0198531 A1 | 12/2002 | Millard et al. |
| 2003/0045881 A1 | 3/2003 | Barouk et al. |
| 2004/0010259 A1 | 1/2004 | Keller et al. |
| 2004/0039394 A1 | 2/2004 | Conti et al. |
| 2004/0097946 A1 | 5/2004 | Dietzel et al. |
| 2004/0138669 A1 | 7/2004 | Horn |
| 2005/0004676 A1 | 1/2005 | Schon et al. |
| 2005/0059978 A1 | 3/2005 | Sherry et al. |
| 2005/0070909 A1 | 3/2005 | Egger et al. |
| 2005/0075641 A1 | 4/2005 | Singhatat et al. |
| 2005/0101961 A1 | 5/2005 | Huebner et al. |
| 2005/0149042 A1 | 7/2005 | Metzger |
| 2005/0192577 A1* | 9/2005 | Mosca ............... A61B 17/1757 606/294 |
| 2005/0228389 A1 | 10/2005 | Stiernborg |
| 2005/0251147 A1 | 11/2005 | Novak |
| 2005/0267482 A1 | 12/2005 | Hyde |
| 2005/0273112 A1 | 12/2005 | Mcnamara |
| 2006/0116679 A1* | 6/2006 | Lutz ..................... A61B 17/80 606/281 |
| 2006/0129163 A1 | 6/2006 | Mcguire |
| 2006/0206044 A1 | 9/2006 | Simon |
| 2006/0217733 A1 | 9/2006 | Plassky et al. |
| 2006/0229621 A1 | 10/2006 | Cadmus |
| 2006/0241607 A1 | 10/2006 | Myerson et al. |
| 2006/0241608 A1 | 10/2006 | Myerson et al. |
| 2006/0264961 A1 | 11/2006 | Murray-Brown |
| 2007/0010818 A1 | 1/2007 | Stone et al. |
| 2007/0123857 A1 | 5/2007 | Deffenbaugh et al. |

(56) References Cited

U.S. PATENT DOCUMENTS

| | | |
|---|---|---|
| 2007/0233138 A1 | 10/2007 | Figueroa et al. |
| 2007/0265634 A1 | 11/2007 | Weinstein |
| 2007/0276383 A1 | 11/2007 | Rayhack |
| 2008/0009863 A1 | 1/2008 | Bond et al. |
| 2008/0015603 A1 | 1/2008 | Collazo |
| 2008/0039850 A1 | 2/2008 | Rowley et al. |
| 2008/0091197 A1 | 4/2008 | Coughlin |
| 2008/0140081 A1 | 6/2008 | Heavener et al. |
| 2008/0147073 A1 | 6/2008 | Ammann et al. |
| 2008/0147128 A1 | 6/2008 | Fritzinger |
| 2008/0172054 A1 | 7/2008 | Claypool et al. |
| 2008/0195215 A1 | 8/2008 | Morton |
| 2008/0208252 A1 | 8/2008 | Holmes |
| 2008/0262500 A1 | 10/2008 | Collazo |
| 2008/0269908 A1 | 10/2008 | Warburton |
| 2008/0288004 A1 | 11/2008 | Schendel |
| 2009/0036893 A1 | 2/2009 | Kartalian et al. |
| 2009/0036931 A1 | 2/2009 | Pech et al. |
| 2009/0054899 A1 | 2/2009 | Ammann et al. |
| 2009/0093849 A1 | 4/2009 | Grabowski |
| 2009/0105767 A1 | 4/2009 | Reiley |
| 2009/0112212 A1 | 4/2009 | Murray et al. |
| 2009/0118733 A1 | 5/2009 | Orsak et al. |
| 2009/0198244 A1 | 8/2009 | Leibel |
| 2009/0198279 A1 | 8/2009 | Zhang et al. |
| 2009/0216089 A1 | 8/2009 | Davidson |
| 2009/0222047 A1 | 9/2009 | Graham |
| 2009/0254092 A1 | 10/2009 | Albiol Llorach |
| 2009/0254126 A1 | 10/2009 | Orbay et al. |
| 2009/0287309 A1 | 11/2009 | Walch et al. |
| 2010/0069910 A1 | 3/2010 | Hasselman |
| 2010/0121334 A1 | 5/2010 | Couture et al. |
| 2010/0130981 A1 | 5/2010 | Richards |
| 2010/0152782 A1 | 6/2010 | Stone et al. |
| 2010/0168799 A1 | 7/2010 | Schumer |
| 2010/0185245 A1 | 7/2010 | Paul et al. |
| 2010/0249779 A1 | 9/2010 | Hotchkiss et al. |
| 2010/0256687 A1 | 10/2010 | Neufeld et al. |
| 2010/0318088 A1 | 12/2010 | Warne et al. |
| 2010/0324556 A1 | 12/2010 | Tyber et al. |
| 2011/0009865 A1 | 1/2011 | Orfaly |
| 2011/0093084 A1 | 4/2011 | Morton |
| 2011/0118739 A1 | 5/2011 | Tyber et al. |
| 2011/0178524 A1 | 7/2011 | Lawrence et al. |
| 2011/0245835 A1 | 10/2011 | Dodds et al. |
| 2011/0264149 A1 | 10/2011 | Pappalardo et al. |
| 2011/0288550 A1 | 11/2011 | Orbay et al. |
| 2011/0301648 A1 | 12/2011 | Lofthouse et al. |
| 2012/0016426 A1 | 1/2012 | Robinson |
| 2012/0065689 A1 | 3/2012 | Prasad et al. |
| 2012/0078258 A1 | 3/2012 | Lo et al. |
| 2012/0123420 A1 | 5/2012 | Honiball |
| 2012/0123484 A1 | 5/2012 | Lietz et al. |
| 2012/0130376 A1 | 5/2012 | Loring et al. |
| 2012/0130382 A1 | 5/2012 | Iannotti et al. |
| 2012/0130383 A1 | 5/2012 | Budoff |
| 2012/0184961 A1 | 7/2012 | Johannaber |
| 2012/0185056 A1 | 7/2012 | Warburton |
| 2012/0191199 A1 | 7/2012 | Raemisch |
| 2012/0239045 A1 | 9/2012 | Li |
| 2012/0253350 A1 | 10/2012 | Anthony et al. |
| 2012/0265301 A1 | 10/2012 | Demers et al. |
| 2012/0277745 A1 | 11/2012 | Lizee |
| 2012/0303033 A1 | 11/2012 | Weiner et al. |
| 2012/0330135 A1 | 12/2012 | Millahn et al. |
| 2013/0012949 A1 | 1/2013 | Fallin et al. |
| 2013/0035694 A1 | 2/2013 | Grimm et al. |
| 2013/0085499 A1 | 4/2013 | Lian |
| 2013/0085502 A1 | 4/2013 | Harrold |
| 2013/0096563 A1 | 4/2013 | Meade et al. |
| 2013/0131821 A1 | 5/2013 | Cachia |
| 2013/0150900 A1 | 6/2013 | Haddad et al. |
| 2013/0150903 A1 | 6/2013 | Vincent |
| 2013/0158556 A1 | 6/2013 | Jones et al. |
| 2013/0165936 A1 | 6/2013 | Myers |
| 2013/0165938 A1 | 6/2013 | Chow et al. |
| 2013/0172942 A1 | 7/2013 | Wright et al. |
| 2013/0184714 A1 | 7/2013 | Kaneyama et al. |
| 2013/0190765 A1 | 7/2013 | Harris et al. |
| 2013/0190766 A1 | 7/2013 | Harris et al. |
| 2013/0204259 A1 | 8/2013 | Zajac |
| 2013/0226248 A1 | 8/2013 | Hatch et al. |
| 2013/0226252 A1 | 8/2013 | Mayer |
| 2013/0231668 A1 | 9/2013 | Olsen et al. |
| 2013/0237987 A1 | 9/2013 | Graham |
| 2013/0237989 A1 | 9/2013 | Bonutti |
| 2013/0267956 A1 | 10/2013 | Terrill et al. |
| 2013/0310836 A1 | 11/2013 | Raub et al. |
| 2013/0325019 A1 | 12/2013 | Thomas et al. |
| 2013/0325076 A1 | 12/2013 | Palmer et al. |
| 2013/0331845 A1 | 12/2013 | Horan et al. |
| 2013/0338785 A1 | 12/2013 | Wong |
| 2014/0005672 A1 | 1/2014 | Edwards et al. |
| 2014/0025127 A1 | 1/2014 | Richter |
| 2014/0039501 A1 | 2/2014 | Schickendantz et al. |
| 2014/0039561 A1 | 2/2014 | Weiner et al. |
| 2014/0046387 A1 | 2/2014 | Waizenegger |
| 2014/0066945 A1 | 3/2014 | Humphreys et al. |
| 2014/0074099 A1 | 3/2014 | Vigneron et al. |
| 2014/0074101 A1 | 3/2014 | Collazo |
| 2014/0094861 A1 | 4/2014 | Fallin |
| 2014/0094924 A1 | 4/2014 | Hacking et al. |
| 2014/0109381 A1 | 4/2014 | Hawkes et al. |
| 2014/0135775 A1 | 5/2014 | Maxson et al. |
| 2014/0163563 A1 | 6/2014 | Reynolds et al. |
| 2014/0171953 A1 | 6/2014 | Gonzalvez et al. |
| 2014/0180342 A1 | 6/2014 | Lowery et al. |
| 2014/0188139 A1 | 7/2014 | Fallin et al. |
| 2014/0188239 A1 | 7/2014 | Cummings |
| 2014/0194884 A1 | 7/2014 | Martin et al. |
| 2014/0194999 A1 | 7/2014 | Orbay et al. |
| 2014/0207144 A1 | 7/2014 | Lee et al. |
| 2014/0214087 A1 | 7/2014 | Wahl et al. |
| 2014/0236247 A1 | 8/2014 | Rezach |
| 2014/0249537 A1 | 9/2014 | Wong et al. |
| 2014/0257308 A1 | 9/2014 | Johannaber |
| 2014/0257509 A1 | 9/2014 | Dacosta et al. |
| 2014/0276815 A1 | 9/2014 | Riccione |
| 2014/0276853 A1 | 9/2014 | Long et al. |
| 2014/0277176 A1* | 9/2014 | Buchanan .......... A61B 17/8057 606/280 |
| 2014/0277214 A1 | 9/2014 | Helenbolt et al. |
| 2014/0288562 A1 | 9/2014 | Von Zabern et al. |
| 2014/0296995 A1 | 10/2014 | Reiley et al. |
| 2014/0303621 A1 | 10/2014 | Gerold et al. |
| 2014/0336658 A1 | 11/2014 | Luna et al. |
| 2014/0343555 A1 | 11/2014 | Russi et al. |
| 2014/0350561 A1 | 11/2014 | Dacosta et al. |
| 2015/0032168 A1 | 1/2015 | Orsak et al. |
| 2015/0045801 A1 | 2/2015 | Axelson, Jr. et al. |
| 2015/0045839 A1 | 2/2015 | Dacosta et al. |
| 2015/0051650 A1 | 2/2015 | Verstreken et al. |
| 2015/0057667 A1 | 2/2015 | Ammann et al. |
| 2015/0066094 A1 | 3/2015 | Anderson et al. |
| 2015/0112446 A1 | 4/2015 | Melamed et al. |
| 2015/0119944 A1 | 4/2015 | Geldwert |
| 2015/0142064 A1 | 5/2015 | Perez et al. |
| 2015/0150608 A1 | 6/2015 | Sammarco |
| 2015/0182273 A1 | 7/2015 | Stemniski et al. |
| 2015/0223851 A1 | 8/2015 | Hill et al. |
| 2015/0245858 A1 | 9/2015 | Weiner et al. |
| 2015/0250519 A1 | 9/2015 | Rezach et al. |
| 2016/0015426 A1 | 1/2016 | Dayton |
| 2016/0022315 A1 | 1/2016 | Soffiatti et al. |
| 2016/0038186 A1 | 2/2016 | Herzog et al. |
| 2016/0135858 A1 | 5/2016 | Dacosta et al. |
| 2016/0151165 A1 | 6/2016 | Fallin et al. |
| 2016/0175089 A1 | 6/2016 | Fallin et al. |
| 2016/0192950 A1 | 7/2016 | Dayton et al. |
| 2016/0192970 A1 | 7/2016 | Dayton et al. |
| 2016/0199076 A1 | 7/2016 | Fallin et al. |
| 2016/0213384 A1 | 7/2016 | Fallin et al. |
| 2016/0235414 A1 | 8/2016 | Hatch et al. |
| 2016/0242791 A1 | 8/2016 | Fallin et al. |

(56) References Cited

U.S. PATENT DOCUMENTS

| | | |
|---|---|---|
| 2016/0256204 A1 | 9/2016 | Patel et al. |
| 2016/0324532 A1 | 11/2016 | Montoya et al. |
| 2016/0338697 A1 | 11/2016 | Biedermann et al. |
| 2016/0354127 A1 | 12/2016 | Lundquist et al. |
| 2017/0014143 A1 | 1/2017 | Dayton et al. |
| 2017/0014173 A1* | 1/2017 | Smith ................ A61B 17/1775 |
| 2017/0042598 A1 | 2/2017 | Santrock et al. |
| 2017/0042599 A1 | 2/2017 | Bays et al. |
| 2017/0056031 A1 | 3/2017 | Awtrey et al. |
| 2017/0079669 A1 | 3/2017 | Bays et al. |
| 2017/0079701 A1 | 3/2017 | Geldwert |
| 2017/0143511 A1 | 5/2017 | Cachia |
| 2017/0164989 A1 | 6/2017 | Weiner et al. |
| 2018/0132868 A1 | 5/2018 | Dacosta et al. |
| 2018/0289379 A1 | 10/2018 | Dacosta et al. |
| 2018/0344334 A1 | 12/2018 | Kim et al. |
| 2019/0254729 A1 | 8/2019 | Rohlfing et al. |
| 2020/0015874 A1 | 1/2020 | Hartson et al. |
| 2020/0054374 A1 | 2/2020 | Geldwert |
| 2020/0060698 A1 | 2/2020 | Woodard et al. |
| 2020/0060743 A1 | 2/2020 | Rohlfing et al. |
| 2020/0129214 A1 | 4/2020 | Pepper et al. |
| 2020/0138491 A1* | 5/2020 | Brigido ................ A61B 17/84 |
| 2020/0229828 A1 | 7/2020 | Wagner et al. |
| 2020/0237387 A1 | 7/2020 | Luttrell et al. |
| 2020/0330109 A1 | 10/2020 | Woodard et al. |
| 2021/0022879 A1 | 1/2021 | Hollis et al. |
| 2021/0113223 A1 | 4/2021 | Schaumann et al. |
| 2021/0128313 A1 | 5/2021 | Graham |

FOREIGN PATENT DOCUMENTS

| | | |
|---|---|---|
| CA | 2854997 A1 | 5/2013 |
| CH | 695846 A5 | 9/2006 |
| CN | 2930668 Y | 8/2007 |
| CN | 201558162 U | 8/2010 |
| CN | 201572172 U | 9/2010 |
| CN | 201586060 U | 9/2010 |
| CN | 201912210 U | 8/2011 |
| CN | 101237835 B | 11/2012 |
| CN | 202801773 U | 3/2013 |
| CN | 103462675 A | 12/2013 |
| CN | 103505276 A | 1/2014 |
| CN | 203458450 U | 3/2014 |
| CN | 103735306 A | 4/2014 |
| CN | 102860860 B | 5/2014 |
| CN | 203576647 U | 5/2014 |
| CN | 104490460 A | 4/2015 |
| CN | 104510523 A | 4/2015 |
| CN | 104523327 A | 4/2015 |
| CN | 104546102 A | 4/2015 |
| CN | 204379413 U | 6/2015 |
| CN | 204410951 U | 6/2015 |
| CN | 204428143 U | 7/2015 |
| CN | 204428144 U | 7/2015 |
| CN | 204428145 U | 7/2015 |
| CN | 204446081 U | 7/2015 |
| DE | 202006010241 U1 | 3/2007 |
| DE | 102007053058 B3 | 4/2009 |
| EP | 685206 B1 | 9/2000 |
| EP | 1508316 B1 | 5/2007 |
| EP | 1897509 B1 | 7/2009 |
| EP | 2124772 A1 | 12/2009 |
| EP | 2124832 B1 | 8/2012 |
| EP | 2632349 A1 | 9/2013 |
| EP | 2665428 A1 | 11/2013 |
| EP | 2742878 A1 | 6/2014 |
| EP | 2750617 A1 | 7/2014 |
| EP | 2849684 A1 | 3/2015 |
| EP | 2624764 B1 | 12/2015 |
| EP | 3023068 A2 | 5/2016 |
| FR | 2362616 A1 | 3/1978 |
| FR | 2764183 B1 | 11/1999 |
| FR | 2953120 B1 | 1/2012 |
| FR | 3030221 A1 | 6/2016 |
| GB | 231718 A | 4/1925 |
| GB | 2154143 A | 9/1985 |
| GB | 2154144 A | 9/1985 |
| GB | 2334214 B | 1/2003 |
| JP | 63005739 A | 1/1988 |
| JP | 05031116 A | 2/1993 |
| JP | 2004174265 A | 6/2004 |
| JP | 2006158972 A | 6/2006 |
| JP | 2008537498 A | 9/2008 |
| JP | 2011092405 A | 5/2011 |
| JP | 2011523889 A | 8/2011 |
| JP | 2014511207 A | 5/2014 |
| JP | 2014521384 A | 8/2014 |
| KR | 100904142 B1 | 6/2009 |
| MD | 756 Z | 11/2014 |
| RU | 2098036 C1 | 12/1997 |
| RU | 2195892 C2 | 1/2003 |
| RU | 2320287 C1 | 3/2008 |
| RU | 2321366 C2 | 4/2008 |
| RU | 2321369 C1 | 4/2008 |
| RU | 2346663 C2 | 2/2009 |
| RU | 2412662 C1 | 2/2011 |
| SU | 1333328 A2 | 8/1987 |
| WO | 0166022 A1 | 9/2001 |
| WO | 03075775 A1 | 9/2003 |
| WO | 2004089227 A2 | 10/2004 |
| WO | 2008051064 A1 | 5/2008 |
| WO | 2008097781 A1 | 8/2008 |
| WO | 2009029798 A1 | 3/2009 |
| WO | 2009032101 A2 | 3/2009 |
| WO | 2011037885 A1 | 3/2011 |
| WO | 2012029008 A1 | 3/2012 |
| WO | 2012058344 A1 | 5/2012 |
| WO | 2012099612 A1 | 7/2012 |
| WO | 2013090392 A1 | 6/2013 |
| WO | 2013134387 A1 | 9/2013 |
| WO | 2013169475 A1 | 11/2013 |
| WO | 2014020561 A1 | 2/2014 |
| WO | 2014022055 A1 | 2/2014 |
| WO | 2014035991 A1 | 3/2014 |
| WO | 2014085882 A1 | 6/2014 |
| WO | 2014147099 A1 | 9/2014 |
| WO | 2014152219 A2 | 9/2014 |
| WO | 2014152535 A1 | 9/2014 |
| WO | 2014177783 A1 | 11/2014 |
| WO | 2014200017 A1 | 12/2014 |
| WO | 2015094409 A1 | 6/2015 |
| WO | 2015105880 A1 | 7/2015 |
| WO | 2015127515 A2 | 9/2015 |
| WO | 2016134160 A1 | 8/2016 |
| WO | 2020180598 A1 | 9/2020 |

OTHER PUBLICATIONS

Langan et al., "Maintenance of Correction of the Modified Lapidus Procedure With a First Metatarsal to Intermediate Cuneiform Cross-Screw Technique," Foot & Ankle International, vol. 41, No. 4, Apr. 1, 2020, published online: Dec. 26, 2019, pp. 426-436.

Lapidus, "The Author's Bunion Operation From 1931 to 1959," Clinical Orthopaedics, vol. 16, 1960, pp. 119-135.

"Lapidus Pearls: Gaining Joint Exposure to Decrease Non-Union," Youtube, Retrieved online from <https://www.youtube.com/watch?v=-jqJyE7pj-Y>, dated Nov. 2, 2009, 3 pages.

Le et al., "Tarsometatarsal Arthrodesis," Operative Techniques in Foot and Ankle Surgery, Section II, Chapter 40, 2011, pp. 281-285.

Lee et al., "Technique Tip: Lateral Soft-Tissue Release for Correction of Hallux Valgus Through a Medial Incision Using A Dorsal Flap Over the First Metatarsal," Foot & Ankle International, vol. 28, No. 8, Aug. 2007, pp. 949-951.

Li et al., "Evolution of Thinking of the Lapidus Procedure and Fixation," Foot and Ankle Clinics, vol. 25, No. 1, Mar. 2020, published online: Dec. 16, 2019, pp. 18 pages.

Lieske et al., "Implantation einer Sprunggelenktotalendo-prothese vom Typ Salto 2," Operative Orthopädie und Traumatologie, vol. 26, No. 4, 2014, pp. 401-413, including English Abstract on p. 403.

(56) References Cited

OTHER PUBLICATIONS

Lopez et al., "Metatarsalgia: Assessment Algorithm and Decision Making," Foot and Ankle Clinics, vol. 24, No. 4, Dec. 2019, published online: Sep. 25, 2019, pp. 561-569.
MAC (Multi Axial Correction) Fixation System, Biomet Trauma, retrieved Dec. 19, 2014, from the Internet: <http://footandanklefixation.com/product/biomet-trauma-mac-multi-axial-correction-fixation-system>, 7 pages.
Magin, "Computernavigierter Gelenkersatz am Knie mit dem Orthopilot," Operative Orthopädie und Traumatologie, vol. 22, No. 1, 2010, pp. 63-80, including English Abstract on p. 64.
Magin, "Die belastungsstabile Lapidus-Arthrodese bei Hallux-valgus-Deformität mittels IVP-Plattenfixateur (V-TEK-System)," Operative Orthopädie und Traumatologie, vol. 26, No. 2, 2014, pp. 184-195, including English Abstract on p. 186.
Michelangelo Bunion System, Surgical Technique, Instratek Incorporated, publication date unknown, 4 pages.
Mini Joint Distractor, Arthrex, retrieved Dec. 19, 2014, from the Internet: <http://www.arthrex.com/foot-ankle/mini-joint-distractor/products>, 2 pages.
MiniRail System, Small Bone Innovations, Surgical Technique, 2010, 24 pages.
Miyake et al., "Three-Dimensional Corrective Osteotomy for Malunited Diaphyseal Forearm Fractures Using Custom- Made Surgical Guides Based on Computer Simulation," JBJS Essential Surgical Techniques, vol. 2, No. 4, 2012, 11 pages.
Mizuno et al., "Detorsion Osteotomy of the First Metatarsal Bone in Hallux Valgus," Japanese Orthopaedic Association, Tokyo, 1956; 30:813-819.
Modular Rail System: External Fixator, Smith & Nephew, Surgical Technique, 2013, 44 pages.
Monnich et al., "A Hand Guided Robotic Planning System for Laser Osteotomy in Surgery," World Congress on Medical Physics and Biomedical Engineering vol. 25/6: Surgery, Nimimal Invasive Interventions, Endoscopy and Image Guided Therapy, Sep. 7-12, 2009, pp. 59-62, (Abstract Only).
Moore et al., "Effect Of Ankle Flexion Angle On Axial Alignment Of Total Ankle Replacement," Foot and Ankle International, vol. 31, No. 12, Dec. 2010, pp. 1093-1098, (Abstract Only).
Mortier et al., "Axial Rotation of the First Metatarsal Head in a Normal Population and Hallux Valgus Patients," Orthopaedics and Traumatology: Surgery and Research, vol. 98, 2012, pp. 677-683.
Mote et al., "First Metatarsal-Cuneiform Arthrodesis for the Treatment of First Ray Pathology: A Technical Guide," JFAS Techniques Guide, vol. 48, No. 5, Sep./Oct. 2009, pp. 593-601.
Myerson, "Cuneiform-Metatarsal Arthrodesis," The Foot and Ankle, Chapter 9, 1997, pp. 107-117.
Nagy et al., "The AO Ulnar Shortening Osteotomy System Indications and Surgical Technique," Journal of Wrist Surgery, vol. 3, No. 2, 2014, pp. 91-97.
NexFix from Nexa Orthopedics, MetaFix I from Merete Medical, Inc. and The BioPro Lower Extremities from BioPro, found in Foot & Ankle International Journal, vol. 28, No. 1, Jan. 2007, 4 pages.
Odenbring et al., "A guide instrument for high tibial osteotomy," Acta Orthopaedica Scandinavica, vol. 60, No. 4, 1989, pp. 449-451.
Okuda et al., "Postoperative Incomplete Reduction of the Sesamoids as a Risk Factor for Recurrence of Hallux Valgus," The Journal of Bone and Joint Surgery, vol. 91-A, No. 1, Jul. 2009, pp. 1637-1645.
Okuda et al., "The Shape of the Lateral Edge of the First Metatarsal Head as a Risk Factor for Recurrence of Hallux Valgus," The Journal of Bone and Joint Surgery, vol. 89, 2007, pp. 2163-2172.
Okuda et al., "Proximal Metatarsal Osteotomy for Hallux Valgus: Comparison of Outcome for Moderate and Severe Deformities, Foot and Ankle International," vol. 29, No. 7, Jul. 2008, pp. 664-670.
Osher et al., "Accurate Determination of Relative Metatarsal Protrusion with a Small Intermetatarsal Angle: A Novel Simplified Method," The Journal of Foot & Ankle Surgery, vol. 53, No. 5, Sep./Oct. 2014, published online: Jun. 3, 2014, pp. 548-556.

Otsuki et al., "Developing a novel custom cutting guide for curved per-acetabular osteotomy," International Orthopaedics (SICOT), vol. 37, 2013, pp. 1033-1038.
Patel et al., "Modified Lapidus Arthrodesis: Rate of Nonunion in 227 Cases," The Journal of Foot & Ankle Surgery, vol. 43, No. 1, Jan./Feb. 2004, pp. 37-42.
"Patient to Patient Precision, Accu-Cut, Osteotomy Guide System," BioPro, Foot & Ankle International Journal, vol. 23, No. 8, Aug. 2002, 2 pages.
Peters et al., "Flexor Hallucis Longus Tendon Laceration as a Complication of Total Ankle Arthroplasty," Foot & Ankle International, vol. 34, No. 1, 2013, pp. 148-149.
"Prophecy Inbone Preoperative Navigation Guides," Wright Medical Technology, Inc., Nov. 2013, 6 pages.
"Rayhack Ulnar Shortening Generation II Low-Profile Locking System Surgical Technique," Wright Medical Technology, Inc., Dec. 2013, 20 pages.
"Reconstructive Surgery of the Foot & Ankle," The Podiatry Institute, Update 2015, Conference Program, May 2015, 28 pages.
Rodriguez et al., "Ilizarov method of fixation for the management of pilon and distal tibial fractures in the compromised diabetic patient: A technique guide," The Foot and Ankle Journal Online, vol. 7, No. 2, 2014, 9 pages.
Rx-Fix Mini Rail External Fixator, Wright Medical Technology, Brochure, Aug. 15, 2014, 2 pages.
Sammarco, "Surgical Strategies: Mau Osteotomy for Correction of Moderate and Severe Hallux Valgus Deformity," Foot & Ankle International, vol. 28, No. 7, Jul. 2007, pp. 857-864.
Sandhu et al., "Digital Arthrodesis With a One-Piece Memory Nitinol Intramedullary Fixation Device: A Retrospective Review," Foot and Ankle Specialist, vol. 6, No. 5, Oct. 2013, pp. 364-366.
Saltzman et al., "Prospective Controlled Trial of STAR Total Ankle Replacement Versus Ankle Fusion: Initial Results," Foot & Ankle International, vol. 30, No. 7, Jul. 2009, pp. 579-596.
Scanlan et al. "Technique Tip: Subtalar Joint Fusion Using a Parallel Guide and Double Screw Fixation," The Journal of Foot and Ankle Surgery, vol. 49, Issue 3, May-Jun. 2010, pp. 305-309, (Abstract Only).
Schon et al., "Cuneiform-Metatarsal Arthrodesis for Hallux Valgus,"The Foot and Ankle, Second Edition, Chapter 8, 2002, pp. 99-117.
Scranton Jr. et al, "Anatomic Variations in the First Ray: Part I. Anatomic Aspects Related to Bunion Surgery," Clinical Orthopaedics and Related Research, vol. 151, Sep. 1980, pp. 244-255.
Shurnas et al., "Proximal Metatarsal Opening Wedge Osteotomy," Operative Techniques in Foot and Ankle Surgery, Section I, Chapter 13, 2011, pp. 73-78.
Siddiqui et al. "Fixation Of Metatarsal Fracture With Bone Plate In A Dromedary Heifer," Open Veterinary Journal, vol. 3, No. 1, 2013, pp. 17-20.
Sidekick Stealth Rearfoot Fixator, Wright Medical Technology, Surgical Technique, Dec. 2, 2013, 20 pages.
Simpson et al., "Computer-Assisted Distraction Ostegogenesis By Ilizarov's Method," International Journal of Medical Robots and Computer Assisted Surgery, vol. 4, No. 4, Dec. 2008, pp. 310-320, (Abstract Only).
Small Bone External Fixation System, Acumed, Surgical Technique, Effective date Sep. 2014, 8 pages.
"Accu-Cut Osteotomy Guide System," BioPro, Brochure, Oct. 2018, 2 pages.
"Acumed Osteotomiesystem Operationstechnik," Acumed, 2014, 19 pages (including 3 pages English translation).
Albano et al., "Biomechanical Study of Transcortical or Transtrabecular Bone Fixation of Patellar Tendon Graft wih Bioabsorbable Pins in ACL Reconstruction in Sheep," Revista Brasileira de Ortopedia (Rev Bras Ortop.) vol. 47, No. 1, 2012, pp. 43-49.
Alvine et al., "Peg and Dowel Fusion of the Proximal Interphalangeal Joint," Foot & Ankle, vol. 1, No. 2, 1980, pp. 90-94.
Anderson et al., "Uncemented STAR Total Ankle Prostheses," The Journal of Bone and Joint Surgery, vol. 86(1, Suppl 2), Sep. 2004, pp. 103-111, (Abstract Only).
Arthrex, "Comprehensive Foot System," Retrieved online from <https://www.arthrex.com/resources/animation/

(56) References Cited

OTHER PUBLICATIONS

8U3iaPvY6kO8bwFAwZF50Q/comprehensive-foot-system?referringTeam=foot_and_ankle>, dated Aug. 27, 2013, 3 pages.
Baravarian, "Why the Lapidus Procedure is Ideal for Bunions," Podiatry Today, Retrieved online from <https://www.hmpgloballearhmpgloballe.com/site/podipodi/article/5542>, dated May 2006, 8 pages.
Bauer et al., "Offset-V Osteotomy of the First Metatarsal Shaft in Hallux Abducto Valgus," McGlamry's Comprehensive Textbook of Foot and Ankle Surgery, Fourth Edition, vol. 1, Chapter 29, 2013, 26 pages.
Bednarz et al., "Modified Lapidus Procedure for the Treatment of Hypermobile Hallux Valgus," Foot & Ankle International, vol. 21, No. 10, Oct. 2000, pp. 816-821.
Blomer, "Knieendoprothetik—Herstellerische Probleme und technologische Entwicklungen," Orthopade, vol. 29, 2000, pp. 688-696, including English Abstract on p. 689.
Bouaicha et al., "Fixation of Maximal Shift Scarf Osteotomy with Inside-Out Plating: Technique Tip," Foot & Ankle International, vol. 32, No. 5, May 2011, pp. 567-569.
Carr et al., "Correctional Osteotomy for Metatarsus Primus Varus and Hallux Valgus," The Journal of Bone and Joint Surgery, vol. 50-A, No. 7, Oct. 1968, pp. 1353-1367.
Catanese et al., "Measuring Sesamoid Position in Hallux Valgus: When Is the Sesamoid Axial View Necessary," Foot and Ankle Specialist, 2014, 3 pages.
Claim Chart for Groves Public Use (Mar. 26, 2014), Exhibit B4 of Defendant Fusion Orthopedics LLC's Invalidity Contentions, No. CV-22-00490-PHX-SRB, US District Court for the District of Arizona, Aug. 27, 2022, 161 pages.
Coetzee et al., "Revision Hallux Valgus Correction," Operative Techniques in Foot and Ankle Surgery, Section I, Chapter 15, 2011, pp. 84-96.
Coetzee et al., "The Lapidus Procedure: A Prospective Cohort Outcome Study," Foot & Ankle International, vol. 25, No. 8, Aug. 2004, pp. 526-531.
Collan et al., "The biomechanics of the first metatarsal bone in hallux valgus: A preliminary study utilizing a weight bearing extremity CT," Foot and Ankle Surgery, vol. 19, 2013, pp. 155-161.
Conti et al., "Effect of the Modified Lapidus Procedure on Pronation of the First Ray in Hallux Valgus," Foot & Ankle International, Feb. 1, 2020, published online: Oct. 16, 2019, 8 pages.
Conti et al., "Effect of the Modified Lapidus Procedure for Hallux Valgus on Foot Width," Foot & Ankle International, Feb. 1, 2020, published online: Oct. 30, 2019, 6 pages.
Cottom, "Fixation of the Lapidus Arthrodesis with a Plantar Interfragmentary Screw and Medial Low Profile Locking Plate," The Journal of Foot & Ankle Surgery, vol. 51, 2012, pp. 517-522.
Coughlin, "Fixation of the Lapidus Arthrodesis with a Plantar Interfragmentary Screw and Medial Low Profile Locking Plate," Orthopaedics and Traumatology, vol. 7, 1999, pp. 133-143.
Cruz et al., "Does Hallux Valgus Exhibit a Deformity Inherent to the First Metatarsal Bone?" The Journal of Foot & Ankle Surgery, vol. 58, No. 6, Nov. 2019, pp. 1210-1214.
Dahlgren et al., "First Tarsometatarsal Fusion Using Saw Preparation vs. Standard Preparation of the Joint: A Cadaver Study," Foot & Ankle Orthopaedics, vol. 4, No. 4, Oct. 2019, 2 pages.
D'Amico et al., "Motion of the First Ray: Clarification Through Investigation," Journal of the American Podiatry Association, vol. 69, No. 1, Jan. 1979, pp. 17-23.
Dayton et al., "Comparison of the Mechanical Characteristics of a Universal Small Biplane Plating Technique Without Compression Screw and Single Anatomic Plate With Compression Screw," The Journal of Foot & Ankle Surgery, vol. 55, No. 3, May/Jun. 2016, published online: Feb. 9, 2016, pp. 567-571.
Dayton et al., "Is Our Current Paradigm for Evaluation and Management of the Bunion Deformity Flawed? A Discussion of Procedure Philosophy Relative to Anatomy," The Journal of Foot and Ankle Surgery, vol. 54, 2015, pp. 102-111.

Dayton et al., "Observed Changes in Radiographic Measurements of the First Ray after Frontal and Transverse Plane Rotation of the Hallux: Does the Hallux Drive the Metatarsal in a Bunion Deformity?," The Journal of Foot and Ankle Surgery, vol. 53, 2014, pp. 584-587.
Dayton et al., "Relationship Of Frontal Plane Rotation Of First Metatarsal To Proximal Articular Set Angle And Hallux Alignment In Patients Undergoing Tarsometatarsal Arthrodesis For Hallux Abducto Valgus: A Case Series And Critical Review Of The Literature," The Journal of Foot and Ankle Surgery, vol. 52, No. 3, May/Jun. 2013, pp. 348-354.
Dayton et al., "Quantitative Analysis of the Degree of Frontal Rotation Required to Anatomically Align the First Metatarsal Phalangeal Joint During Modified Tarsal-Metatarsal Arthrodesis Without Capsular Balancing," The Journal of Foot and Ankle Surgery, 2015, pp. 1-6.
Dayton et al., "Dorsal Suspension Stitch: An Alternative Stabilization After Flexor Tenotomy for Flexible Hammer Digit Syndrome," The Journal of Foot and Ankle Surgery, vol. 48, No. 5, Sep./Oct. 2009, pp. 602-605.
Dayton et al., "The Extended Knee Hemilithotomy Position for Gastrocnemius Recession," The Journal of Foot and Ankle Surgery, vol. 49, 2010, pp. 214-216.
Dayton et al., "Hallux Varus as Complication of Foot Compartment Syndrome," The Journal of Foot and Ankle Surgery, vol. 50, 2011, pp. 504-506.
Dayton et al., "Measurement of Mid-Calcaneal Length on Plain Radiographs: Reliability of a New Method," Foot and Ankle Specialist, vol. 4, No. 5, Oct. 2011, pp. 280-283.
Dayton et al., "A User-Friendly Method of Pin Site Management for External Fixators," Foot and Ankle Specialist, Sep. 16, 2011, 4 pages.
Dayton et al., "Effectiveness of a Locking Plate in Preserving Midcalcaneal Length and Positional Outcome after Evans Calcaneal Osteotomy: A Retrospective Pilot Study," The Journal of Foot and Ankle Surgery, vol. 52, 2013, pp. 710-713.
Dayton et al., "Does Postoperative Showering or Bathing of a Surgical Site Increase the Incidence of Infection? A Systematic Review of the Literature," The Journal of Foot and Ankle Surgery, vol. 52, 2013, pp. 612-614.
Dayton et al., "Technique for Minimally Invasive Reduction of Calcaneal Fractures Using Small Bilateral External Fixation," The Journal of Foot and Ankle Surgery, Article in Press, 2014, 7 pages.
Dayton et al., "Clarification of the Anatomic Definition of the Bunion Deformity," The Journal of Foot and Ankle Surgery, vol. 53, 2014, pp. 160-163.
Dayton et al., "Observed Changes in Radiographic Measurements of the First Ray after Frontal Plane Rotation of the First Metatarsal in a Cadaveric Foot Model," The Journal of Foot and Ankle Surgery, Article in Press, 2014, 5 pages.
Dayton et al., "Observed Changes in First Metatarsal and Medial Cuneiform Positions after First Metatarsophalangeal Joint Arthrodesis," The Journal of Foot and Ankle Surgery, vol. 53, 2014, pp. 32-35.
Dayton et al., "Reduction of the Intermetatarsal Angle after First Metatarsal Phalangeal Joint Arthrodesis: A Systematic Review," The Journal of Foot and Ankle Surgery, Article in Press, 2014, 4 pages.
Dayton et al., "Principles of Management of Growth Plate Fractures in the Foot and Ankle," Clinics in Podiatric Medicine and Surgery, Pediatric Foot Deformities, Oct. 2013, 17 pages.
Dayton et al., "Observed Changes in Radiographic Measurements of the First Ray after Frontal and Transverse Plane Rotation of the Hallux: Does the Hallux Drive the Metatarsal in a Bunion Deformity?," The Journal of Foot and Ankle Surgery, Article in Press, 2014, 4 pages.
Dayton et al., "Comparison of Complications for Internal and External Fixation for Charcot Reconstruction: A Systematic Review," The Journal of Foot and Ankle Surgery, Article in Press, 2015, 4 pages.
Dayton et al., "A new triplanar paradigm for bunion management," Lower Extremity Review, Apr. 2015, 9 pages.
Dayton et al., "American College of Foot and Ankle Surgeons' Clinical Consensus Statement: Perioperative Prophylactic Antibi-

(56) References Cited

OTHER PUBLICATIONS otic Use in Clean Elective Foot Surgery," The Journal of Foot and Ankle Surgery, Article in Press, 2015, 7 pages.

Dayton et al., "Complications of Metatarsal Suture Techniques for Bunion Correction: A Systematic Review of the Literature," The Journal of Foot and Ankle Surgery, Article in Press, 2015, 3 pages.

Dayton et al., "Observed Changes in Radiographic Measurements of the First Ray after Frontal Plane Rotation of the First Metatarsal in a Cadaveric Foot Model," The Journal of Foot & Ankle Surgery, vol. 53, 2014, pp. 274-278.

Dayton et al., "Relationship of Frontal Plane Rotation of First Metatarsal to Proximal Articular Set Angle and Hallux Alignment in Patients Undergoing Tarsometatarsal Arthrodesis for Hallux Abducto Valgus: A Case Series and Critical Review of the Literature," The Journal of Foot & Ankle Surgery, 2013, Article in Press, Mar. 1, 2013, 7 pages.

Dayton et al., "Biwinged Excision for Round Pedal Lesions," The Journal of Foot and Ankle Surgery, vol. 35, No. 3, 1996, pp. 244-249.

Smith et al., "Opening Wedge Osteotomies for Correction of Hallux Valgus: A Review of Wedge Plate Fixation," Foot and Ankle Specialist, vol. 2, No. 6, Dec. 2009, pp. 277-282.

"Smith & Nephew scores a HAT-TRICK with its entry into the high-growth hammer toe repair market," Smith & Nephew, Jul. 31, 2014, 2 pages.

Sokoloff, "Lapidus Procedure," Textbook of Bunion Surgery, Chapter 15, 1981, pp. 277-287.

"Speed Continuous Active Compression Implant," BioMedical Enterprises, Inc., A120-029 Rev. 3, 2013, 4 pages.

Stableloc External Fixation System, Acumed, Product Overview, Effective date Sep. 2015, 4 pages.

Stahl et al., "Derotation Of Post-Traumatic Femoral Deformities By Closed Intramedullary Sawing," Injury, vol. 37, No. 2, Feb. 2006, pp. 145-151, (Abstract Only).

Stamatis et al., "Mini Locking Plate as "Medial Buttress" for Oblique Osteotomy for Hallux Valgus," Foot & Ankle International, vol. 31, No. 10, Oct. 2010, pp. 920-922.

Stewart, "Use for BME Speed Nitinol Staple Fixation for the Lapidus Procedure," date unknown, 1 page.

Talbot et al., "Assessing Sesamoid Subluxation: How Good is the AP Radiograph?," Foot and Ankle International, vol. 19, No. 8, Aug. 1998, pp. 547-554.

TempFix Spanning the Ankle Joint Half Pin and Transfixing Pin Techniques, Biomet Orthopedics, Surgical Technique, 2012, 16 pages.

Toth et al., "The Effect of First Ray Shortening in the Development of Metatarsalgia in the Second Through Fourth Rays After Metatarsal Osteotomy," Foot & Ankle International, vol. 28, No. 1, Jan. 2007, pp. 61-63.

Tricot et al., "3D-corrective osteotomy using surgical guides for posttraumatic distal humeral deformity," Acta Orthopaedica Belgica, vol. 78, No. 4, 2012, pp. 538-542.

"Visionaire: Patient Matched Cutting Blocks Surgical Procedure," Smith & Nephew, Inc., 2009, 2 pages.

Vitek et al., "Die Behandlung des Hallux rigidus mit Cheilektomie und Akin-Moberg-Osteotomie unter Verwendung einer neuen Schnittlehre und eines neuen Schraubensystems," Orthopadische Praxis, vol. 44, Nov. 2008, pp. 563-566, including English Abstract on p. 564.

Vitek, "Neue Techniken in der Fußchirurgie Das V-tek-System," ABW Wissenschaftsverlag GmbH, 2009, 11 pages, including English Abstract.

Weber et al., "Use of the First Ray Splay Test to Assess Transverse Plane Instability Before First Metatarsocuneiform Fusion," The Journal of Foot and Ankle Surgery, vol. 45, No. 4, Jul./Aug. 2006, pp. 278-282.

Weber et al., "A Simple System For Navigation Of Bone Alignment Osteotomies Of The Tibia," International Congress Series, vol. 1268, Jan. 2004, pp. 608-613, (Abstract Only).

Weil et al., "Anatomic Plantar Plate Repair Using the Weil Metatarsal Osteotomy Approach," Foot & Ankle Specialist, vol. 4, No. 3, 2011, pp. 145-150.

Wendl et al., "Navigation in der Knieendoprothetik," OP-Journal, vol. 17, 2002, pp. 22-27, including English Abstract.

Whipple et al., "Zimmer Herbert Whipple Bone Screw System: Surgical Techniques for Fixation of Scaphoid and Other Small Bone Fractures," Zimmer, 2003, 59 pages.

Wienke et al., "Bone Stimulation For Nonunions: What the Evidence Reveals," Podiatry Today, vol. 24, No. 9, Sep. 2011, pp. 52-57.

Wukich et al., "Hypermobility of the First Tarsometatarsal Joint," Foot and Ankle Clinics, vol. 10, No. 1, Mar. 2005, pp. 157-166.

Yakacki et al. "Compression Forces of Internal and External Ankle Fixation Devices with Simulated Bone Resorption," Foot and Ankle International, vol. 31, No. 1, Jan. 2010, pp. 76-85, (Abstract Only).

Yasuda et al., "Proximal Supination Osteotomy of the First Metatarsal for Hallux Valgus," Foot and Ankle International, vol. 36, No. 6, Jun. 2015, pp. 696-704.

Defendant Fusion Orthopedics LLC's Invalidity Contentions, No. CV-22-00490-PHX-SRB, US District Court for the District of Arizona, Aug. 27, 2022, 41 pages.

Prior Art Publications, Exhibit A of Defendant Fusion Orthopedics LLC's Invalidity Contentions, No. CV-22-00490-PHX-SRB, US District Court for the District of Arizona, Aug. 27, 2022, 3 pages.

Claim Chart for Fishco, "Making the Lapidus Easy," The Podiatry Institute (Apr. 2014), Exhibit B1 of Defendant Fusion Orthopedics LLC's Invalidity Contentions, No. CV-22-00490-PHX-SRB, US District Court for the District of Arizona, Aug. 27, 2022, 97 pages.

Claim Chart for Fishco, "A Straightforward Guide to the Lapidus Bunionectomy," HMP Global (Sep. 6, 2013), Exhibit B2 of Defendant Fusion Orthopedics LLC's Invalidity Contentions, No. CV-22-00490-PHX-SRB, US District Court for the District of Arizona, Aug. 27, 2022, 67 pages.

Claim Chart for Groves, "Functional Position Joint Sectioning: Pre-Load Method for Lapidus Arthrodesis," Update 2015: Proceedings of the Annual Meeting of the Podiatry Institute, Chpt. 6, pp. 23-29 (Apr. 2015), Exhibit B3 of Defendant Fusion Orthopedics LLC's Invalidity Contentions, No. CV-22-00490-PHX-SRB, US District Court for the District of Arizona, Aug. 27, 2022, 151 pages.

Claim Chart for Mote, "First Metatarsal-Cuneiform Arthrodesis for the Treatment of First Ray Pathology: A Technical Guide," The Journal Foot & Ankle Surgery (Sep. 1, 2009), Exhibit B5 of Defendant Fusion Orthopedics LLC's Invalidity Contentions, No. CV-22-00490-PHX-SRB, US District Court for the District of Arizona, Aug. 27, 2022, 21 pages.

Claim Chart for U.S. Pat. No. 10,376,268 to Fallin et al., entitled "Indexed Tri-Planar Osteotomy Guide and Method," issued Aug. 13, 2019, Exhibit B6 of Defendant Fusion Orthopedics LLC's Invalidity Contentions, No. CV-22-00490-PHX-SRB, US District Court for the District of Arizona, Aug. 27, 2022, 155 pages.

Claim Chart for U.S. Pat. No. 8,282,645 to Lawrence et al., entitled "Metatarsal Bone Implant Cutting Guide," issued Jan. 18, 2010, Exhibit B7 of Defendant Fusion Orthopedics LLC's Invalidity Contentions, No. CV-22-00490-PHX-SRB, US District Court for the District of Arizona, Aug. 27, 2022, 76 pages.

Claim Chart for U.S. Pat. No. 9,452,057 to Dacosta et al., entitled "Bone Implants and Cutting Apparatuses and Methods," issued Apr. 8, 2011, Exhibit B8 of Defendant Fusion Orthopedics LLC's Invalidity Contentions, No. CV-22-00490-PHX-SRB, US District Court for the District of Arizona, Aug. 27, 2022, 110 pages.

Obviousness Chart, Exhibit C of Defendant Fusion Orthopedics LLC's Invalidity Contentions, No. CV-22-00490-PHX-SRB, US District Court for the District of Arizona, Aug. 27, 2022, 153 pages.

"Finite Element Analysis of a Magnesium Based ACL Interference Screw Drive to Improve Insertion Sucess" Thesis submitted by Jonquil Reve' Flowers, 2012, 75 pages.

Dayton et al., "Medial Incision Approach to the First Metatarsophalangeal Joint," The Journal of Foot and Ankle Surgery, vol. 40, No. 6, Nov./Dec. 2001, pp. 414-417.

Dayton et al., "Reduction of the Intermetatarsal Angle after First Metatarsophalangeal Joint Arthrodesis in Patients with Moderate

(56) References Cited

OTHER PUBLICATIONS and Severe Metatarsus Primus Adductus," The Journal of Foot and Ankle Surgery, vol. 41, No. 5, Sep./Oct. 2002, pp. 316-319.
Dayton et al., "Use of the Z Osteotomy for Tailor Bunionectomy," The Journal of Foot and Ankle Surgery, vol. 42, No. 3, May/Jun. 2003, pp. 167-169.
Dayton et al., "Early Weightbearing After First Metatarsophalangeal Joint Arthrodesis: A Retrospective Observational Case Analysis," The Journal of Foot and Ankle Surgery, vol. 43, No. 3, May/Jun. 2004, pp. 156-159.
DeCarbo et al., "The Weil Osteotomy: A Refresher," Techniques in Foot and Ankle Surgery, vol. 13, No. 4, Dec. 2014, pp. 191-198.
DeCarbo et al., "Resurfacing Interpositional Arthroplasty for Degenerative Joint Disease of the First Metatarsalphalangeal Joint," Podiatry Management, Jan. 2013, pp. 137-142.
DeCarbo et al., "Locking Plates: Do They Prevent Complications?," Podiatry Today, Apr. 2014, 7 pages.
De Geer et al., "A New Measure of Tibial Sesamoid Position in Hallux Valgus in Relation to the Coronal Rotation of the First Metatarsal in CT Scans," Foot and Ankle International, Mar. 26, 2015, 9 pages.
DiDomenico et al., "Correction of Frontal Plane Rotation of Sesamoid Apparatus during the Lapidus Procedure: A Novel Approach," The Journal of Foot and Ankle Surgery, vol. 53, 2014, pp. 248-251.
DiDomenico et al., "Lapidus Bunionectomy: First Metatarsal-Cuneiform Arthrodesis," McGlamry's Comprehensive Textbook of Foot and Ankle Surgery, Fourth Edition, vol. 1, Chapter 31, 2013, 24 pages.
Dobbe et al. "Patient-Tailored Plate For Bone Fixation And Accurate 3D Positioning In Corrective Osteotomy," Medical and Biological Engineering and Computing, vol. 51, No. 1-2, Feb. 2013, pp. 19-27, (Abstract Only).
Doty et al., "Hallux valgus and hypermobility of the first ray: facts and fiction," International Orthopaedics, vol. 37, 2013, pp. 1655-1660.
Easley et al., "Current Concepts Review: Hallux Valgus Part I: Pathomechanics, Clinical Assessment, and Nonoperative Management," Foot and Ankle International, vol. 28, No. 5, May 2007, pp. 654-659.
Easley et al., "Current Concepts Review: Hallux Valgus Part II: Operative Treatment," Foot and Ankle International, vol. 28, No. 6, Jun. 2007, pp. 748-758.
Easley et al., "What is the Best Treatment for Hallux Valgus?," Evidence-Based Orthopaedics—The Best Answers to Clinical Questions, Chapter 73, 2009, pp. 479-491.
EBI Extra Small Rail Fixator, Biomet Trauma, retrieved Dec. 19, 2014, from the Internet: < http://footandanklefixation.com/product/biomet-trauma-ebi-extra-small-rail-fixator>, 7 pages.
Eustace et al., "Hallux valgus, first metatarsal pronation and collapse of the medial longitudinal arch—a radiological correlation," Skeletal Radiology, vol. 23, 1994, pp. 191-194.
Fallin et al., US Provisional Application Entitled Indexed Tri-Planar Osteotomy Guide and Method, U.S. Appl. No. 62/118,378, filed Feb. 19, 2015, 62 pages.
Feilmeier et al., "Reduction of Intermetatarsal Angle after First Metatarsophalangeal Joint Arthrodesis in Patients with Hallux Valgus," The Journal of Foot and Ankle Surgery, vol. 53, 2014, pp. 29-31.
Feilmeier et al., "Incidence of Surgical Site Infection in the Foot and Ankle with Early Exposure and Showering of Surgical Sites: A Prospective Observation," The Journal of Foot and Ankle Surgery, vol. 53, 2014, pp. 173-175.
Fishco, "A Straightforward Guide To The Lapidus Bunionectomy, "Podiatry Today, Retrieved online from <https://www.hmpgloballearningnetwork.com/site/podiatry/blogged/straightforward-guide-lapidus-bunionectomy>, dated Sep. 6, 2013, 5 pages.
Fishco, "Making the Lapidus Easy," The Podiatry Institute, Update 2014, Chapter 14, 2014, pp. 91-93.
Fleming et al., "Results of Modified Lapidus Arthrodesis Procedure Using Medial Eminence as an Interpositional Autograft," The Journal of Foot & Ankle Surgery, vol. 50, 2011, pp. 272-275.

"Foot and Ankle Instrument Set," Smith & Nephew, 2013, 2 pages.
Fuhrmann, "Arthrodesis of the First Tarsometatarsal Joint for Correction of the Advanced Splayfoot Accompanied by a Hallux Valgus," Operative Orthopadie und Traumatologie, No. 2, 2005, pp. 195-210.
"Futura Forefoot Implant Arthroplasty Products," Tornier, Inc., 2008, 14 pages.
Galli et al., "Enhanced Lapidus Arthrodesis: Crossed Screw Technique With Middle Cuneiform Fixation Further Reduces Sagittal Mobility," The Journal of Foot & Ankle Surgery, vol. 54, vol. 3, May/Jun. 2015, published online: Nov. 21, 2014, pp. 437-440.
Garthwait, "Accu-Cut System Facilitates Enhanced Precision," Podiatry Today, vol. 18, No. 6, Jun. 2005, 6 pages.
Gerard et al., "The Modified Lapidus Procedure," Orthopedics, vol. 31, No. 3, Mar. 2008, 7 pages.
Giannoudis et al., "Hallux Valgus Correction," Practical Procedures in Elective Orthopaedic Surgery, Pelvis and Lower Extremity, Chapter 38, 2012, 22 pages.
Gonzalez Del Pino et al., "Variable Angle Locking Intercarpal Fusion System for Four-Corner Arthrodesis: Indications and Surgical Technique," Journal of Wrist Surgery, vol. 1, No. 1, Aug. 2012, pp. 73-78.
Gotte, "Entwicklung eines Assistenzrobotersystems für die Knieendoprothetik," Forschungsberichte, Technische Universitat Munchen, 165, 2002, 11 pages, including partial English Translation.
Gregg et al., "Plantar plate repair and Weil osteotomy for metatarsophalangeal joint instability," Foot and Ankle Surgery, vol. 13, 2007, pp. 116-121.
Greiner, "The Jargon of Pedal Movements," Foot & Ankle International, vol. 28, No. 1, Jan. 2007, pp. 109-125.
Grondal et al., "A Guide Plate for Accurate Positioning of First Metatarsophalangeal Joint during Fusion," Operative Orthopädie Und Traumatologie, vol. 16, No. 2, 2004, pp. 167-178 (Abstract Only).
Groves, "Functional Position Joint Sectioning: Pre-Load Method for Lapidus Arthrodesis," The Podiatry Institute, Update 2015, Chapter 6, 2015, pp. 23-29.
Groves, "Operative Report," St. Tammany Parish Hospital, Date of Procedure, Mar. 26, 2014, 2 pages.
Hardy et al., "Observations on Hallux Valgus," The Journal of Bone and Joint Surgery, vol. 33B, No. 3, Aug. 1951, pp. 376-391.
"HAT-TRICK Lesser Toe Repair System," Smith & Nephew, Brochure, Aug. 2014, 12 pages.
"HAT-TRICK Lesser Toe Repair System, Foot and Ankle Technique Guide, Metatarsal Shortening Osteotomy Surgical Technique," Smith & Nephew, 2014, 16 pages.
Hetherington et al., "Evaluation of surgical experience and the use of an osteotomy guide on the apical angle of an Austin osteotomy," The Foot, vol. 18, 2008, pp. 159-164.
Hirao et al., "Computer assisted planning and custom-made surgical guide for malunited pronation deformity after first metatarsophalangeal joint arthrodesis in rheumatoid arthritis: A case report," Computer Aided Surgery, vol. 19, Nos. 1-3, 2014, pp. 13-19.
"Hoffmann II Compact External Fixation System," Stryker, Brochure, Literature No. 5075-1-500, 2006, 12 pages.
"Hoffmann II Micro Lengthener," Stryker, Operative Technique, Literature No. 5075-2-002, 2008, 12 pages.
"Hoffmann Small System External Fixator Orthopedic Instruments," Stryker, retrieved Dec. 19, 2014, from the Internet: <http://www.alibaba.com/product-detail/Stryker-Hoffmann-Small-System-External-Fixator_1438850129.html>, 3 pages.
Holmes, Jr., "Correction of the Intermetatarsal Angle Component of Hallux Valgus Using Fiberwire-Attached Endo-buttons," Revista Internacional de Ciencias Podologicas, vol. 6, No. 2, 2012, pp. 73-79.
Integra, "Integra Large Qwix Positioning and Fixation Screw, Surgical Technique," 2012, 16 pages.
Kilmartin et al., "Combined rotation scarf and Akin osteotomies for hallux valgus: a patient focused 9 year follow up of 50 patients," Journal of Foot and Ankle Research, vol. 3, No. 2, 2010, 12 pages.
Kim et al., "A Multicenter Retrospective Review of Outcomes for Arthrodesis, Hemi-Metallic Joint Implant, and Resectional Arthroplasty

(56) References Cited

OTHER PUBLICATIONS in the Surgical Treatment of End-Stage Hallux Rigidus," The Journal of Foot and Ankle Surgery, vol. 51, 2012, pp. 50-56.

Kim et al., "A New Measure of Tibial Sesamoid Position in Hallux Valgus in Relation to the Coronal Rotation of the First Metatarsal in CT Scans," Foot and Ankle International, vol. 36, No. 8, 2015, pp. 944-952.

* cited by examiner

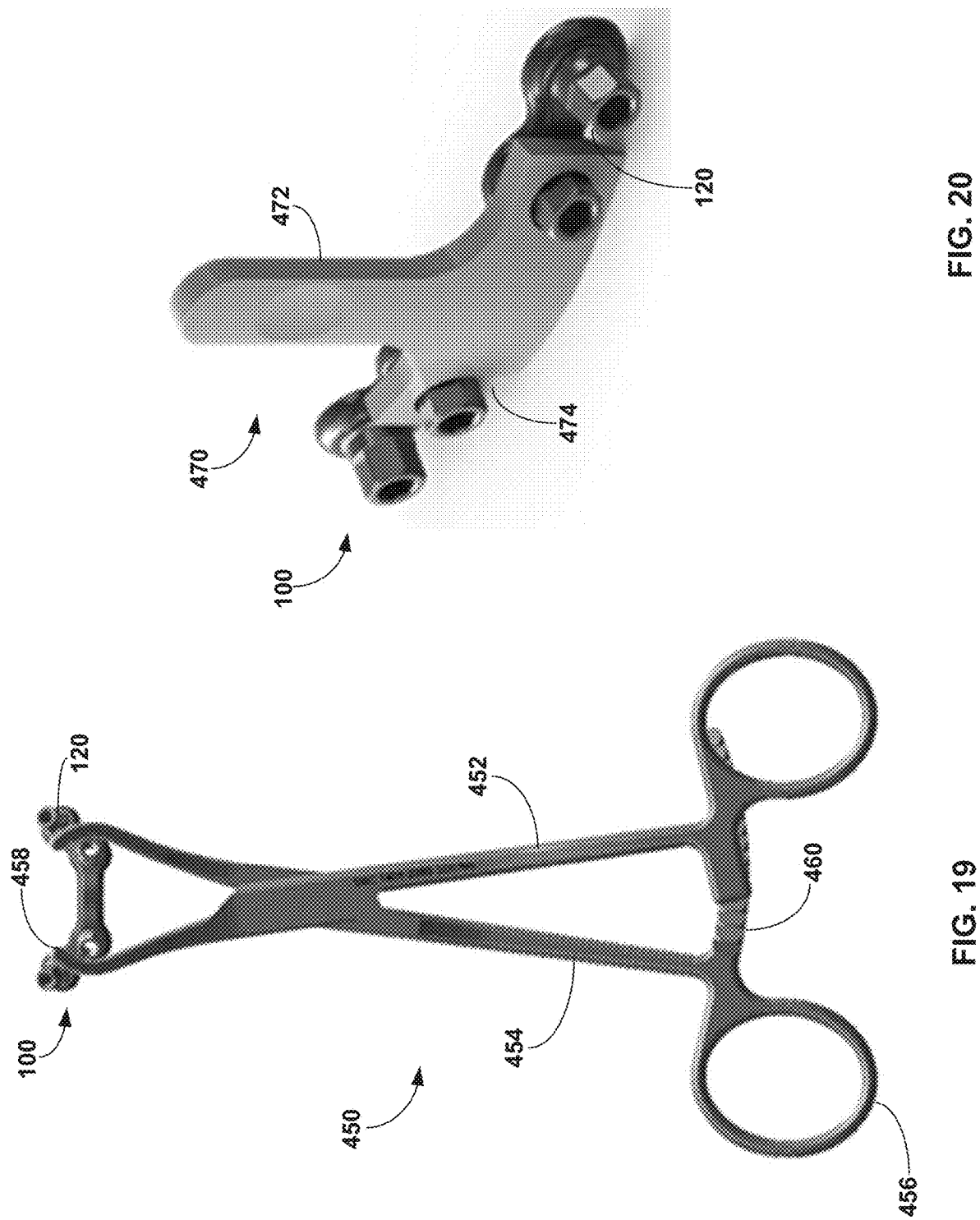

SYSTEM AND TECHNIQUE FOR METATARSAL REALIGNMENT WITH REDUCED INCISION LENGTH

RELATED MATTERS

This application claims the benefit of U.S. Provisional Patent Application No. 63/151,041, filed Feb. 18, 2021, the entire contents of which are incorporated herein by reference.

TECHNICAL FIELD

This disclosure relates generally to devices and techniques for repositioning bones and, more particularly, to devices and techniques for repositioning bones in the foot.

BACKGROUND

Bones within the human body, such as bones in the foot, may be anatomically misaligned. For example, one common type of bone deformity is hallux valgus, which is a progressive foot deformity in which the first metatarsophalangeal joint is affected and is often accompanied by significant functional disability and foot pain. The metatarsophalangeal joint is laterally deviated, resulting in an abduction of the first metatarsal while the phalanges adduct. This often leads to development of soft tissue and a bony prominence on the medial side of the foot, which is called a bunion.

Surgical intervention may be used to correct a bunion deformity. A variety of different surgical procedures exist to correct bunion deformities and may involve removing the abnormal bony enlargement on the first metatarsal and/or attempting to realign the first metatarsal relative to the adjacent metatarsal. Surgical instruments that can facilitate efficient, accurate, and reproducible clinical results are useful for practitioners performing bone realignment techniques.

For patients, surgical intervention requires making one or more incisions through the patient's skin to access the underlying bones to perform a corrective procedure. A longer incision provides the surgeon with greater access to perform the procedure. However, a longer incision results in a longer scar for the patient after healing, which can be cosmetically undesirable. For this reason, the patient may prefer a shorter incision and/or fewer incisions. This can be challenging for the surgeon because it limits access for performing the corrective procedure.

SUMMARY

In general, this disclosure is directed to devices, systems, and techniques for performing a metatarsal realignment while minimizing the length and/or number of the incision(s) needed to access the bones for performing the procedure. As a result, a patient undergoing the procedure may have a shorter, less visible incision and resulting scar line, providing healing and/or cosmetic benefits as compared to a procedure performed using a longer incision and/or more incisions.

In some implementations, a clinician surgically accesses a tarsometatarsal ("TMT") joint defined between a metatarsal and an opposed cuneiform. The TMT joint may be the first TMT joint between the first metatarsal and medial cuneiform or a lesser TMT joint between a lesser metatarsal and opposed cuneiform. In either case, the clinician can make a comparatively small incision to access the TMT joint. Once accessed, the clinician can prepare the end face of the metatarsal and the end face of the opposed cuneiform. Example preparation steps may include reaming, cutting, rongeuring, curetting, burring, fenstrating and/or other similar techniques for exposing subchondral bone and/or establishing bleeding bone faces to promote fusion following rejoining of the metatarsal and the cuneiform.

Either before or after preparation of one or both end faces, the metatarsal is realigned within one or more planes in three-dimensional space. In one example, the clinician engages a bone positioner (also referred to as a bone positioning device) with the metatarsal and a bone other than the metatarsal. The bone positioner can then be actuated to move the metatarsal in one or more planes for realignment. The bone positioner may have a metatarsal engagement member positionable in contact with an external surface of the skin overlying the metatarsal. In other words, instead of making a separate incision to place the bone positioner in contact with the metatarsal bone, the bone positioner can engage the metatarsal bone through the skin to avoid the need for an additional incision.

In some examples, the bone positioner includes a tip that can be positioned on a lateral side of a metatarsal other than the metatarsal being moved. For example, where the metatarsal being moved is a first metatarsal, a small stab incision may be made on a lateral side of a metatarsal other than the metatarsal being moved, such as between the second metatarsal and the third metatarsal. In these examples, the tip of the bone positioner can be placed in contact with the lateral side of the second metatarsal. The bone positioning may include a mechanism that moves the metatarsal engagement member and the tip towards each other, causing the metatarsal to move in one or more planes to help correct a misalignment of the metatarsal. Additionally or alternatively, the clinician may grasp a pin inserted into the metatarsal to move the metatarsal in one or more planes.

After moving the metatarsal relative to the opposed cuneiform and/or an adjacent metatarsal, the clinician can perform a variety of steps to complete the surgical procedure. In some examples, the clinician installs a compressor and utilizes the compressor to compress the prepared end face of the metatarsal together with the prepared end face of the cuneiform. Additionally or alternatively, the clinician may temporarily fixate a moved position of the metatarsal relative to the cuneiform. For example, the clinician can insert one or more fixation wires through the metatarsal into one or more adjacent bones (e.g., an adjacent metatarsal, across the TMT joint into the opposed cuneiform).

In either case, clinician may cause the metatarsal to fuse to the cuneiform. For example, the clinician may install one or more fixation devices across the TMT joint to fixate the position of the metatarsal relative to the cuneiform for subsequent healing and fusion. In some implementations, the clinician installs one more bone plates across the TMT joint. For example, the clinician may utilize a generally U-shaped bone plate have a base and two outwardly extending legs. The clinician may position the base across the TMT joint with the legs extending upwardly in a dorsal direction relative to the base. This type of plate configuration can position one or more fixation holes of the bone plate at a location accessible by the clinician through the comparatively small incision. By contrast, when utilizing a straight plate or other plate configuration, one or more fixation holes of the bone plate may be located subdermally (after inserting the bone place through the incision) in a way that can make it challenging for the clinician to install screws through the fixation holes.

In some implementations, the clinician may utilize a plate holder to help manipulate and/or hold the bone plate within the incision. The plate holder may be an instrument configured to releasably grasp an external surface of the plate and/or be inserted into a fixation hole of the plate, such as a drill guide inserted through the fixation hole. Using the plate holder, the clinician may be able to controllably and precisely position the bone plate and/or hold the bone plate during installation of one or more screws in the small incision created to access the TMT joint space. This can help address space constrains caused by the comparatively small length incision, which can make it difficult for the clinician to properly position the bone plate using their fingers along.

In one example, a method of performing a minimal incision metatarsal correction procedure is described. The method incudes preparing an end of a metatarsal and preparing an end of a cuneiform separated from the metatarsal by a tarsometatarsal joint. The method also involves moving the metatarsal relative to the cuneiform using a bone positioning device that includes a metatarsal engagement member and a tip. The example specifies that the metatarsal engagement member is positioned in contact with a skin of the patient covering a medial side of the metatarsal and that the tip is positioned on a lateral side of a different metatarsal. The method also includes, after moving the metatarsal relative to the cuneiform, causing the metatarsal to fuse to the cuneiform.

The details of one or more examples are set forth in the accompanying drawings and the description below. Other features, objects, and advantages will be apparent from the description and drawings, and from the claims.

BRIEF DESCRIPTION OF DRAWINGS

FIGS. 19-21 are illustrations of example plate holder configurations that may be used to manipulate a bone plate during a minimal incision procedure.

DETAILED DESCRIPTION

Figure 1B:
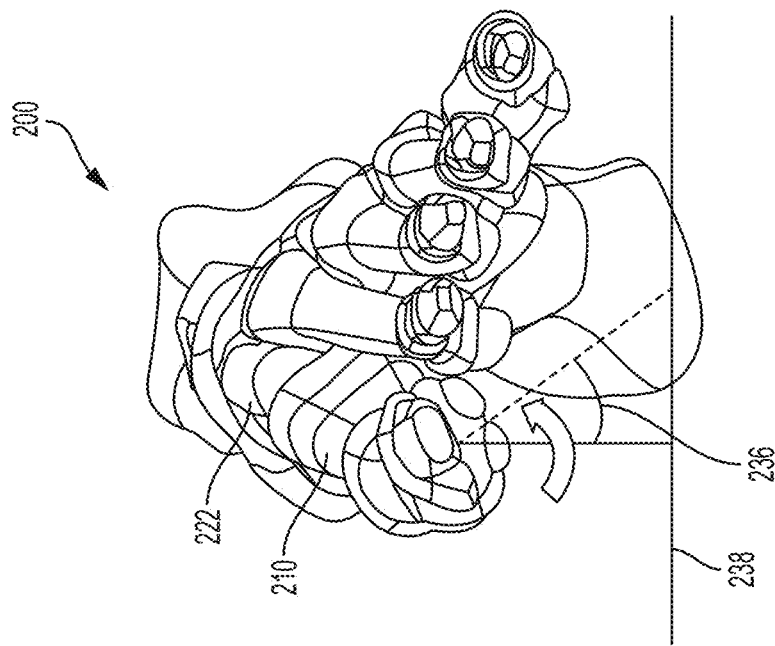
FIGS. 1A and 1B are front views of a foot showing a normal first metatarsal position and an example frontal plane rotational misalignment position, respectively.

This disclosure generally relates to devices, systems, and techniques for performing a minimal incision bone realignment procedure. In an exemplary application, the devices and techniques can be used during a surgical procedure performed on one or more bones, such as a bone alignment, osteotomy, fusion procedure, fracture repair, and/or other procedures where one or more bones are to be set in a desired position. Such a procedure can be performed, for example, on bones (e.g., adjacent bones separated by a joint or different portions of a single bone) in the foot or hand, where bones are relatively small compared to bones in other parts of the human anatomy. In one example, a procedure utilizing an embodiments of the disclosure can be performed to correct an alignment between a metatarsal (e.g. a first metatarsal) and a cuneiform (e.g., a medial cuneiform), such as a bunion correction. An example of such a procedure is a lapidus procedure. In another example, the procedure can be performed by modifying an alignment of a metatarsal (e.g. a first metatarsal). An example of such a procedure is a basilar metatarsal osteotomy procedure.

Preparation and fusion of two opposed bone portions, such as a metatarsal and cuneiform, may be performed according to the disclosure for a variety of clinical reasons and indications. Preparation and fusion of a metatarsal and cuneiform at the TMT joint may be performed to treat hallux valgus and/or other bone and/or joint conditions.

Hallux valgus, also referred to as hallux abducto valgus, is a complex progressive condition that is characterized by lateral deviation (valgus, abduction) of the hallux and medial deviation of the first metatarsophalangeal joint. Hallux valgus typically results in a progressive increase in the hallux abductus angle, the angle between the long axes of the first metatarsal and proximal phalanx in the transverse plane. An increase in the hallux abductus angle may tend to laterally displace the plantar aponeurosis and tendons of the intrinsic and extrinsic muscles that cross over the first metatarsophalangeal joint from the metatarsal to the hallux. Consequently, the sesamoid bones may also be displaced, e.g., laterally relative to the first metatarsophalangeal joint, resulting in subluxation of the joints between the sesamoid bones and the head of the first metatarsal. This can increase the pressure between the medial sesamoid and the crista of the first metatarsal head.

While techniques and devices are described herein particularly in connection with the first metatarsal and medial cuneiform of the foot, the techniques and devices may be used on other adjacent bones separated by a joint in the hand or foot. For example, the techniques and devices may be performed on a different metatarsal (e.g., second, third, fourth, or fifth metatarsal) and its opposed cuneiform/cuboid. Accordingly, reference to a first metatarsal and medial cuneiform herein may be replaced with other bone pairs without departing from the scope of the disclosure.

To further understand example techniques of the disclosure, the anatomy of the foot will first be described with respect to FIGS. 1-3 along with example misalignments that may occur and be corrected according to the present disclosure. A bone misalignment may be caused by hallux valgus (bunion), a natural growth deformity, and/or other condition.

Figure 1A:
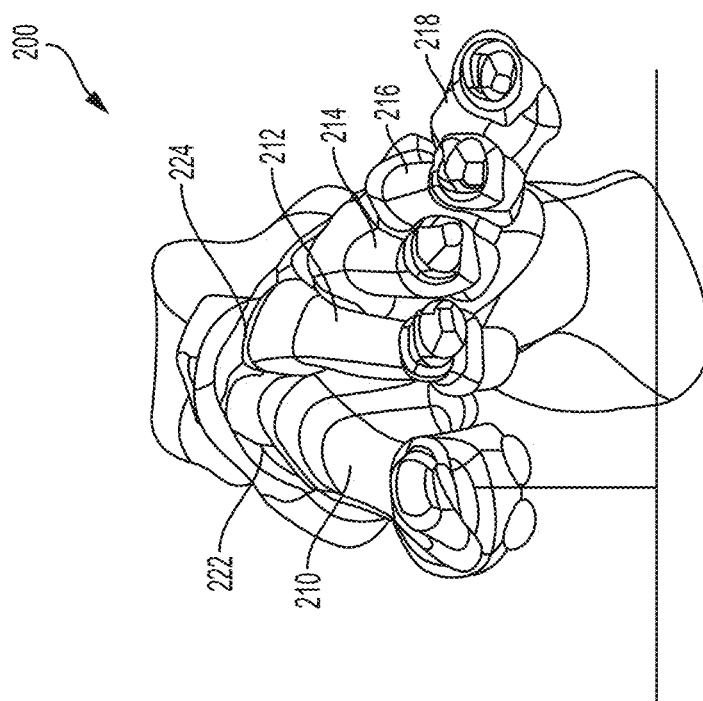
Figure 2A:
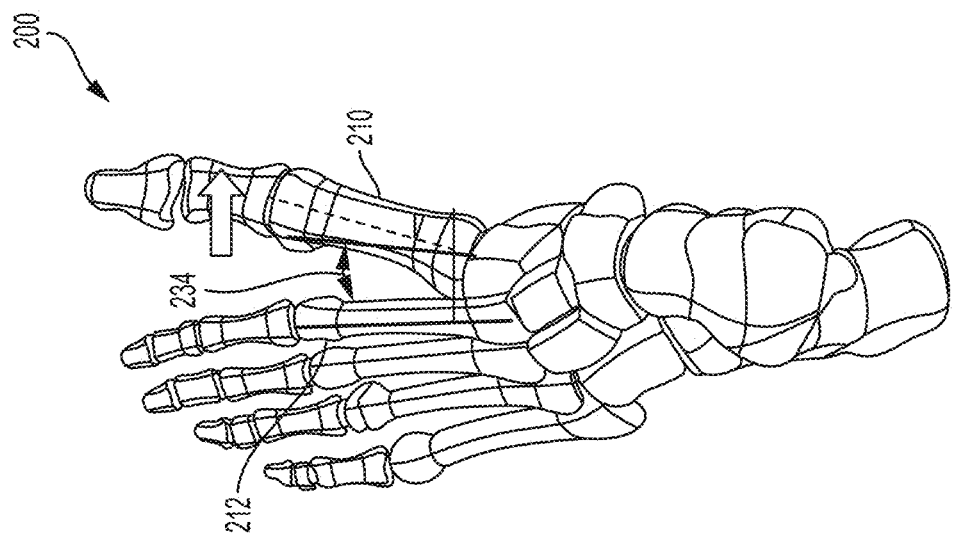
FIGS. 2A and 2B are top views of a foot showing a normal first metatarsal position and an example transverse plane misalignment position, respectively.
Figure 2B:
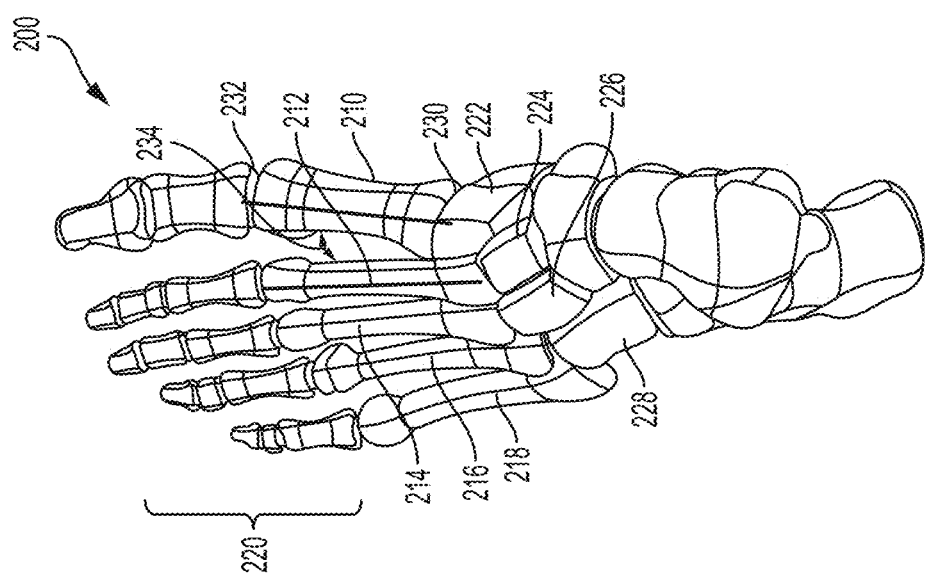
Figure 3B:
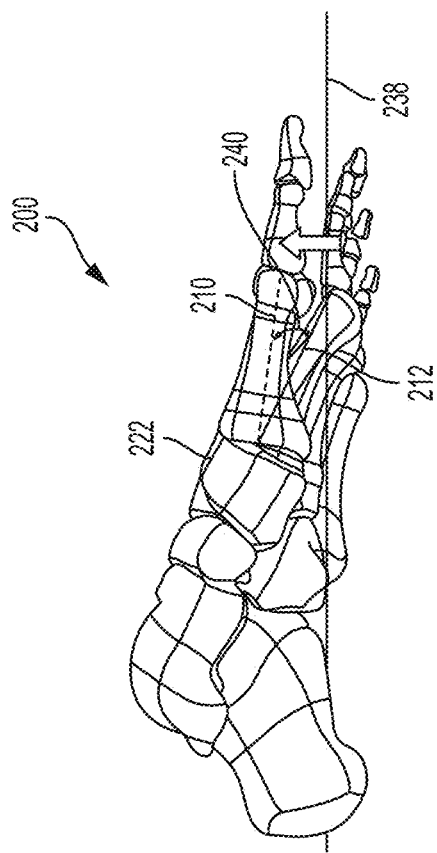
FIGS. 3A and 3B are side views of a foot showing a normal first metatarsal position and an example sagittal plane misalignment position, respectively.
Figure 3A:
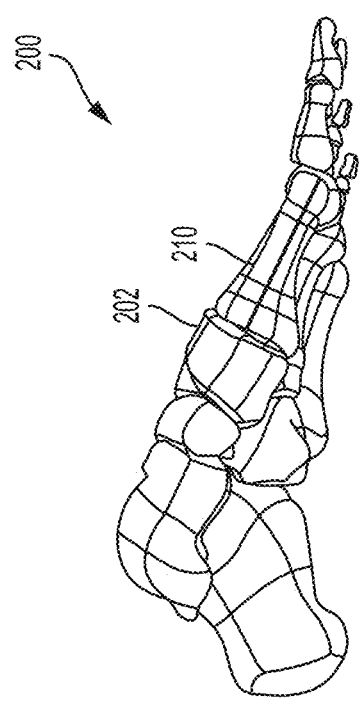

FIGS. 1A and 1B are front views of foot 200 showing a normal first metatarsal position and an example frontal plane rotational misalignment position, respectively. FIGS. 2A and 2B are top views of foot 200 showing a normal first metatarsal position and an example transverse plane misalignment position, respectively. FIGS. 3A and 3B are side views of foot 200 showing a normal first metatarsal position and an example sagittal plane misalignment position, respectively. While FIGS. 1B, 2B, and 3B show each respective planar misalignment in isolation, in practice, a metatarsal may be misaligned in any two of the three planes or even all three planes. Accordingly, it should be appreciated that the depiction of a single plane misalignment in each of FIGS. 1B, 2B, and 3B is for purposes of illustration and a metatarsal may be misaligned in multiple planes that is desirably corrected. Further, a bone condition treated according to the disclosure may not present any of the example misalignments described with respect to FIGS. 1B, 2B, and 3B, and it should be appreciated that the disclosure is not limited in this respect.

With reference to FIGS. 1A and 2A, foot 200 is composed of multiple bones including a first metatarsal 210, a second metatarsal 212, a third metatarsal 214, a fourth metatarsal 216, and a fifth metatarsal 218. The metatarsals are connected distally to phalanges 220 and, more particularly, each to a respective proximal phalanx. The first metatarsal 210 is connected proximally to a medial cuneiform 222, while the second metatarsal 212 is connected proximally to an intermediate cuneiform 224 and the third metatarsal is connected proximally to lateral cuneiform 226. The fourth and fifth metatarsals 216, 218 are connected proximally to the cuboid bone 228. The joint 230 between a metatarsal and respective cuneiform (e.g., first metatarsal 210 and medial cuneiform 222) is referred to as the tarsometatarsal ("TMT") joint. The joint 232 between a metatarsal and respective proximal phalanx is referred to as a metatarsophalangeal joint. The angle 234 between adjacent metatarsals (e.g., first metatarsal 210 and second metatarsal 212) is referred to as the intermetatarsal angle ("IMA").

As noted, FIG. 1A is a frontal plane view of foot 200 showing a typical position for first metatarsal 210. The frontal plane, which is also known as the coronal plane, is generally considered any vertical plane that divides the body into anterior and posterior sections. On foot 200, the frontal plane is a plane that extends vertically and is perpendicular to an axis extending proximally to distally along the length of the foot. FIG. 1A shows first metatarsal 210 in a typical rotational position in the frontal plane. FIG. 1B shows first metatarsal 210 with a frontal plane rotational deformity characterized by a rotational angle 236 relative to ground, as indicated by line 238.

FIG. 2A is a top view of foot 200 showing a typical position of first metatarsal 210 in the transverse plane. The transverse plane, which is also known as the horizontal plane, axial plane, or transaxial plane, is considered any plane that divides the body into superior and inferior parts. On foot 200, the transverse plane is a plane that extends horizontally and is perpendicular to an axis extending dorsally to plantarly (top to bottom) across the foot. FIG. 2A shows first metatarsal 210 with a typical IMA 234 in the transverse plane. FIG. 2B shows first metatarsal 210 with a transverse plane rotational deformity characterized by a greater IMA caused by the distal end of first metatarsal 210 being pivoted medially relative to the second metatarsal 212.

FIG. 3A is a side view of foot 200 showing a typical position of first metatarsal 210 in the sagittal plane. The sagittal plane is a plane parallel to the sagittal suture which divides the body into right and left halves. On foot 200, the sagittal plane is a plane that extends vertically and is perpendicular to an axis extending proximally to distally along the length of the foot. FIG. 3A shows first metatarsal 210 with a typical rotational position in the sagittal plane. FIG. 3B shows first metatarsal 210 with a sagittal plane rotational deformity characterized by a rotational angle 240 relative to ground, as indicated by line 238.

Surgical techniques and instruments according to the disclosure can be useful to correct a misalignment of one or more bones, such as the metatarsal and opposed cuneiform, and/or promote fusion of the metatarsal and cuneiform across the TMT joint. In some applications, the technique involves forming two incisions: a comparatively small incision to access the TMT joint and a second stab incision between two metatarsals (e.g., between a second metatarsal and a third metatarsal). The end of the metatarsal and the end of the cuneiform can be prepared. For example, the clinician can insert a bone preparation instrument through the comparatively small incision to prepare the end face of one or both bones.

Before or after preparing one or both ends, a bone positioner having a metatarsal engagement member and tip can be installed to help facilitate realignment of the metatarsal relative to the cuneiform. The metatarsal engagement member can be positioned in contact with the external surface of the skin of the patient overlaying the medial side of the metatarsal. The tip can be inserted through the small stab incision between the adjacent metatarsals. For example, the tip can be inserted through the small stab incision and the tip positioned in contact with a lateral face of a metatarsal different than the metatarsal being moved. In either case, the bone positioner may include one more mechanisms that allow the metatarsal engagement member to be moved relative to the tip, resulting in the metatarsal moving in one or more planes relative to the cuneiform.

With the metatarsal suitably repositioned, the clinician may temporarily and/or permanently fixate the moved position of the metatarsal relative to the cuneiform. For example, the clinician may insert a fixation pin through the metatarsal and into the cuneiform (e.g., across the TMT joint) to hold the position of the metatarsal for subsequent installation of one or more permanent fixation devices. In some implementations, the clinician compresses the prepared end face of the metatarsal together with the prepared end face of the cuneiform before installing one or more temporary and/or permanent fixation devices.

In either case, in some examples, the clinician may grasp a plate holder instrument operatively connected to a bone plate and use the instrument to position the bone plate through the comparatively small incision. Through manipulation of the plate holder instrument, the clinician may position and hold the bone plate across the TMT joint while the clinician inserts one or more fixation elements through one or more corresponding fixation holes in the bone plate into the underlying metatarsal and/or cuneiform.

Figure 4:
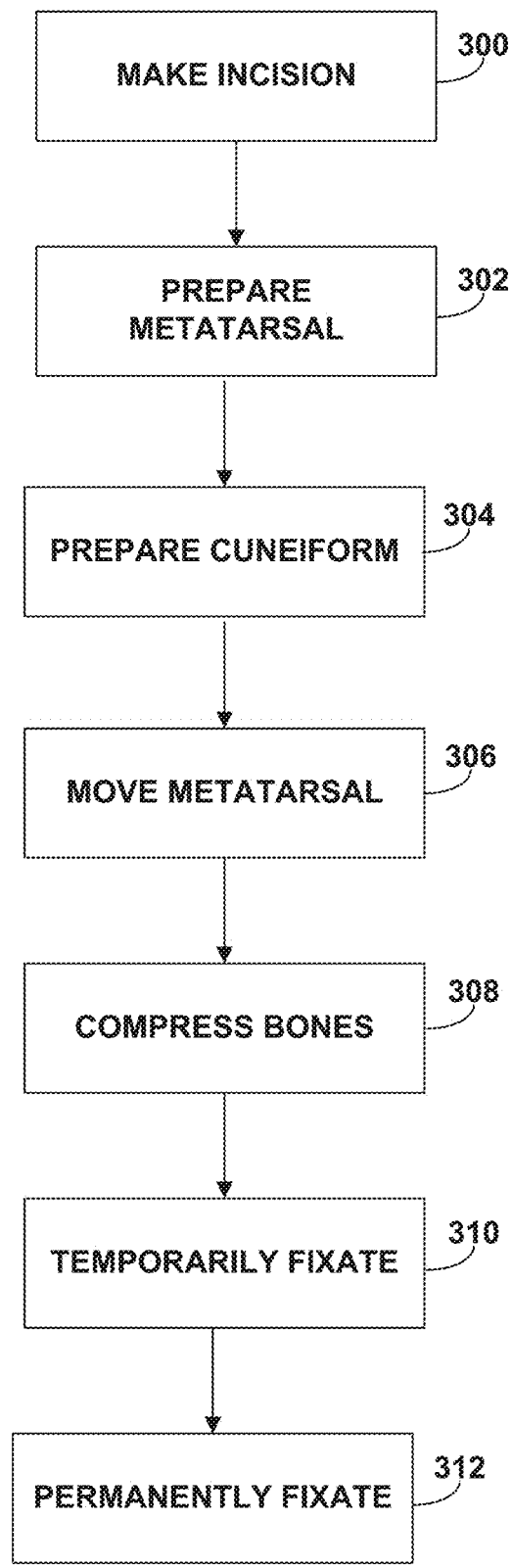
FIG. 4 is a flow diagram illustrating an example technique for performing a minimally invasive surgical procedure to correct a position of a metatarsal relative to an adjacent bone.

FIG. 4 is a flow diagram illustrating an example technique for performing a minimally invasive metatarsal realignment procedure. The example technique will be described with respect to first metatarsal 210 and medial cuneiform 222, although can be performed on other bones, as discussed above. For purposes of discussion, the technique of FIG. 4 will be discussed with respect to different example images illustrated in FIGS. 5-22.

Figure 5:
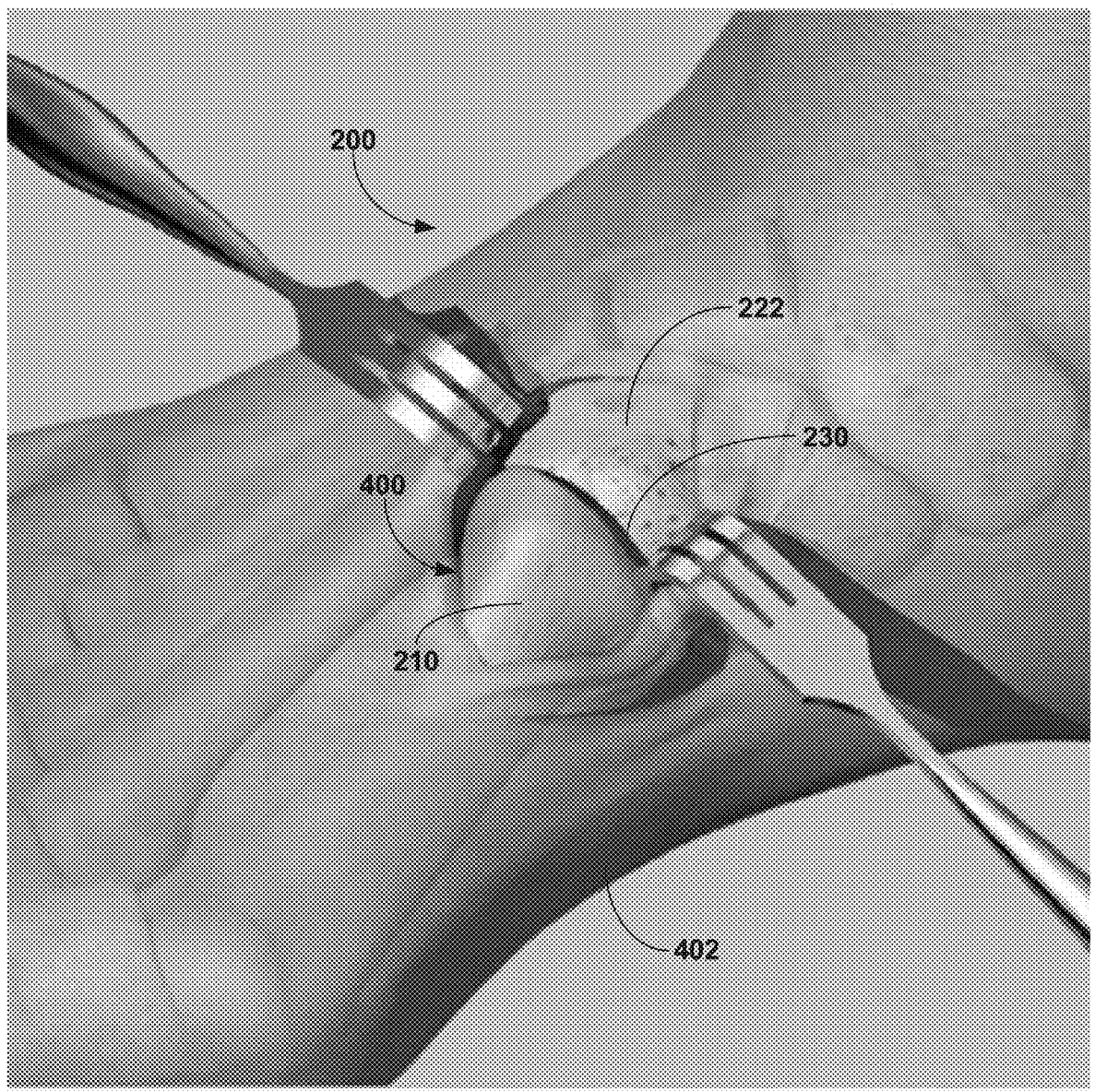
FIG. 5 is a perspective view of a foot showing example surgical access to a TMT joint.

FIG. 5 is a perspective view of a foot 200 showing example surgical access to the TMT joint. With reference to FIGS. 4 and 5, the example technique involves surgically accessing TMT joint 230 separating first metatarsal 210 from opposed medial cuneiform 222 (300). To surgically access the joint, the patient may be placed in a supine position on the operating room table and general anesthesia or monitored anesthesia care administered. Hemostasis can be obtained by applying thigh tourniquet or mid-calf tourniquet. An incision 400 (FIG. 5) can be made through the skin 402, such as on a dorsal side of the foot, a medial side of the foot, or on a dorsal-medial side of the foot.

To help identify the proper location to make incision 400, in some implementations, the clinician may image foot 200 prior to making the incision. For example, the clinician may take a fluoroscopic (e.g. X-ray) image of at least a portion of foot 200 encompassing TMT joint 230 prior to making incision 400. Imaging foot 200 can reveal to the clinician the location of TMT joint 230 about which incision 400 can be centered when subsequently cutting through skin 402. In these applications, the clinician may use a tool such as a ruler, incision guide, or other instrument fabricated at least partially from a radiopaque material to designate the location of TMT joint 230 under imaging.

Figure 6:
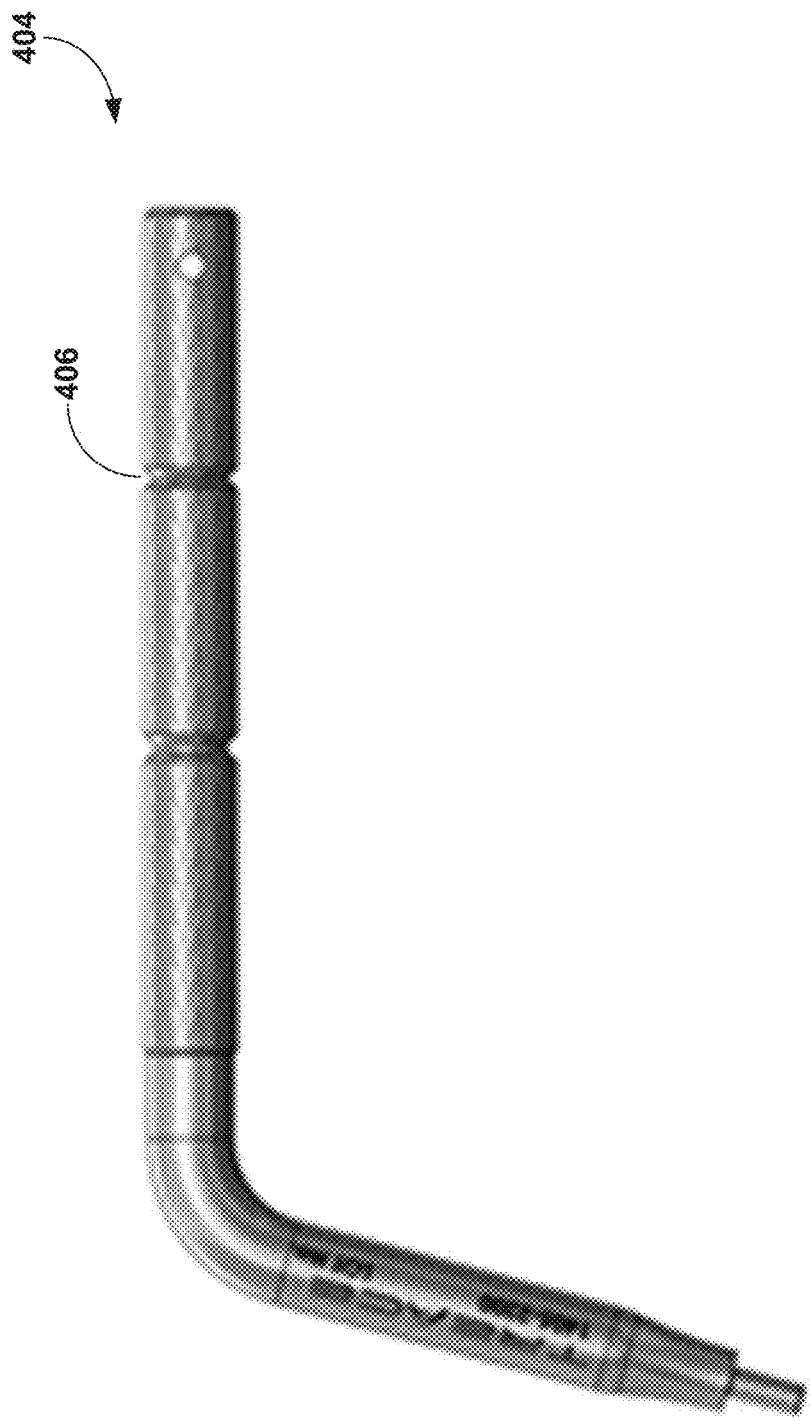
FIG. 6 is an image of one example configuration of an incision guide that can be used to help designate the location of a TMT joint prior to making an incision.

FIG. 6 is an image of one example configuration of an incision guide 404 that can be used to help designate the location of TMT joint 230 prior to making incision 400. In this example, incision guide 404 is shown as including one or more radio-identifiable marking lines 406, which are distinguishable from a remainder of the incision guide under imaging. The one or more radio-identifiable marking lines 406 can be formed from a different material than a remainder of the incision guide, have a different thickness than a remainder of the incision guide, and/or otherwise be distinguishable under imaging from the remainder of the incision guide. In either configuration, the clinician may align radio-identifiable marking line 406 with TMT joint 230 under imaging to designate the location for subsequently making incision 400.

Figure 7:
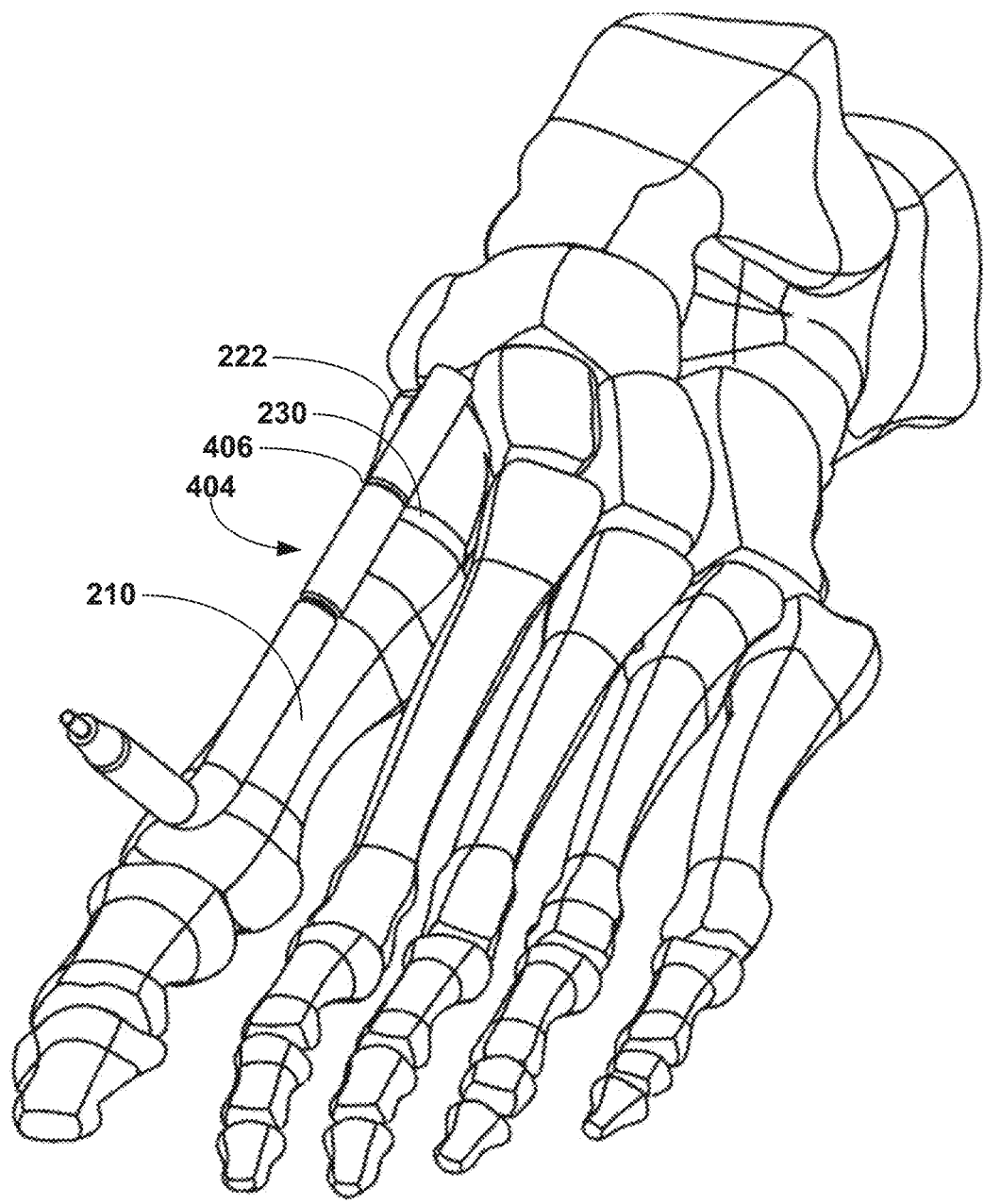
FIG. 7 is a perspective view of a foot showing the incision guide of FIG. 6 positioned over a metatarsal with a radio-identifiable marking line.

FIG. 7 is a perspective view of foot 200 showing incision guide 404 positioned over metatarsal 210 with radio-identifiable marking line 406 generally co-planar with TMT joint 230 between the metatarsal and medial cuneiform 222. By accurately identifying the location of TMT joint 230 prior to making incision 400, the clinician may make a comparatively smaller incision substantially centered on the TMT joint than if the clinician makes an exploratory incision without first identifying the precise location of the joint.

Independent of whether the clinician does or does not utilize an imaging device to identify TMT joint 230 prior to making incision 400, the clinician can make the incision to access the underlying joint. While the specific length of incision 400 (in the distal to proximal direction parallel to the long axis of first metatarsal 210) may vary depending on the anatomy of the specific patient undergoing the procedure and the clinician performing the surgery, in some examples, the incision may have a length less than 12 cm. For example, the clinician may cut incision 400 to have a length less than 10.5 cm, less than 8 cm, less than 6 cm, or less than 5 cm. In some instances, incision 400 may have a length ranging from 1 cm to 12 cm, such as from 1.5 cm to 8 cm, 2 cm to 6 centimeters, or from 3 cm to 4 cm.

With TMT joint 230 exposed, the technique of FIG. 4 involves preparing the end face of first metatarsal 210 and/or preparing the end face of medial cuneiform 222 (302, 304). While FIG. 4 schematically illustrates an example order in which the end face of the first metatarsal and the end face of the medial cuneiform can be prepared, it should be appreciated that the surgical technique is not limited to any particular order of preparation. For example, the clinician can prepare the end face of either the metatarsal or the cuneiform before preparing the end face of the other bone. Further, one or both of the end faces of the metatarsal and the cuneiform can be prepared before and/or after the metatarsal is moved relative to the cuneiform. Accordingly, unless otherwise specified, the order of bone preparation and/or movement is not limited.

In general, the clinician can prepare the end of each bone forming a TMT joint so as to promote fusion of the bone ends across the TMT joint following realignment. Bone preparation may involve using a tissue removing instrument to apply a force to the end face of the bone so as to create a bleeding bone face to promote subsequent fusion. Example tissue removing instruments that can be used include, but are not limited to, a saw, a rotary bur, a rongeur, a reamer, an osteotome, a curette, and the like. The tissue removing instrument can be applied to the end face of the bone being prepared to remove cartilage and/or bone. For example, the tissue removing instrument may be applied to the end face to remove cartilage (e.g., all cartilage) down to subchondral bone. Additionally or alternatively, the tissue removing instrument may be applied to cut, fenestrate, morselize, and/or otherwise reshape the end face of the bone and/or form a bleeding bone face to promote fusion. In instances where a cutting operation is performed to remove an end portion of a bone, the cutting may be performed freehand or with the aid of a cutting guide having a guide surface positionable over the portion of bone to be cut. When using a bone preparation guide, a cutting instrument can be inserted against the guide surface (e.g., between a slot define between two guide surfaces) to guide the cutting instrument for bone removal.

In some examples, the clinician cuts at least one bone defining the TMT joint 230 (e.g., one or both of first metatarsal 210 and medial cuneiform 222). The clinician may cut both bones defining the TMT joint or may cut only one bone defining the joint and perform a different preparation technique on the other bone.

Figure 8:
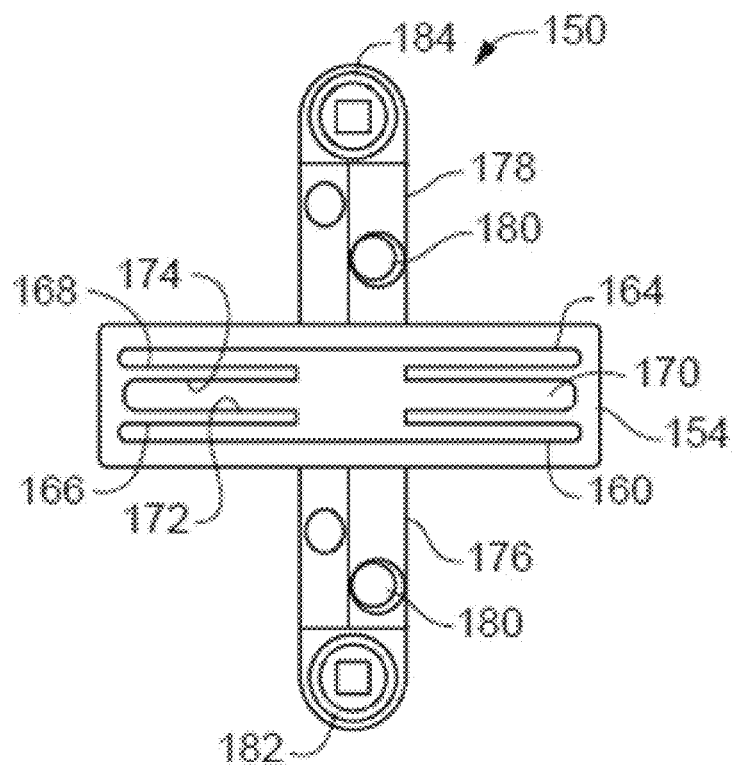
FIG. 8 illustrates one example bone preparation guide that may be used as part of a minimally invasive procedure.

While a variety of different bone preparation guides can be used to guide a cutting instrument, FIG. 8 illustrates one example bone preparation guide 150 that may be used as part of a minimally invasive procedures. In the illustrated example, bone preparation guide 150 includes a body 154 defining at least one guide surface for guiding a cutting instrument which, in the illustrated example, is shown as including two guide surfaces: a first guide surface 160 to define a first preparing plane and a second guide surface 164 to define a second preparing plane. A tissue removing instrument (e.g., a saw, rotary bur, osteotome, etc.) can be aligned with and/or guided along (e.g., in contact with) the surface(s) to remove tissue (e.g., remove cartilage or bone and/or make cuts to bone). The first and second guide surfaces 160, 164 can be spaced from each other by a distance, (e.g., between about 2 millimeters and about 10 millimeters, such as between about 4 and about 7 millimeters). In the embodiment shown, the first and second guide surfaces are parallel, such that cuts to adjacent bones using the guide surfaces will be generally parallel. However, in other examples, one guide surface can be angled relative to another guide surface at a non-zero degree angle.

In some configurations, as shown in FIG. 8, a first facing surface 166 is positioned adjacent the first guide surface 160 and/or a second facing surface 168 is positioned adjacent the second guide surface 164. In such configurations, the distance between the first guide surface and the first facing surface defines a first guide slot, and the distance between the second guide surface and the second facing surface defines a second guide slot. Each slot can be sized to receive a tissue removing instrument to prepare the bone ends. The first and second slots may be parallel or skewed. In the illustrated example, the facing surfaces each contain a gap, such that the surface is not a single, continuous surface. In other embodiments, one or both facing surfaces can be a single, continuous surface lacking any such gap.

The space between adjacent guide surfaces and/or cutting slots (when configured with multiple of such features) can be solid material or can include one or more openings. In the illustrated example, an opening 170 is defined by body 154 between the first and second guide surfaces. The opening can be an area between the guide surfaces useful for allowing a practitioner to have a visual path to bones during bone preparation and/or to receive an instrument. In the configuration shown, the opening extends across the body and a distance from a surface 172 opposite of the first facing surface 166 to a surface 174 opposite of the second facing surface 168.

The illustrated bone preparation guide also includes a first end 176 extending from the body 154 in a first direction and a second end 178 extending from the body in a second direction. The second direction can be different than the first direction (e.g., an opposite direction). As shown, each of the first end and the second end can include at least one fixation aperture 180 configured to receive a fixation pin to secure the bone preparation guide to an underlying bone. For example, first end 176 of bone preparation guide 150 may define a first fixation aperture through which a first pin can be inserted and the second end 178 of bone preparation guide 150 may define a second fixation aperture through which a second pin can be inserted. These two fixation apertures may be parallel aligned, such that first and second pins 112, 114 extend through the holes parallel to each other. The first end 176 and/or the second end 178 of bone preparation guide 150 may also define one or more additional fixation apertures that are angled (at a non-zero degree angle) or otherwise skewed relative to the two parallel fixation apertures.

In use, a clinician may insert the two parallel pins through fixation apertures 180 and may optionally insert one or more angled pins through the one or more angled fixation apertures. This combination of parallel and angled pins may prevent bone preparation guide 150 from being removed from the underlying bones being worked upon. When the clinician has completed using the bone preparation guide, the angled pin or pins may be removed leaving the two parallel pins inserted into the underlying bones. Bone preparation guide 150 can be slid or otherwise moved up and off the parallel pins and, in some examples, a compressor (e.g., a compressor-distractor) thereafter inserted down over the pins. The compressor can then be used to apply a force to the pins to compress the prepared ends of the two facing bones together.

In some examples as shown in FIG. 8, bone preparation guide 150 can also include a first adjustable stabilization member 182 engaged with the first end 176 and/or a second adjustable stabilization member 184 engaged with the second end 178. Each of the members can be threaded and engage a threaded aperture defined by the ends. The elevation of each end can be adjusted with respect to a bone by adjusting the stabilization member. In some embodiments, as shown, the stabilization members are cannulated such that they can receive a fixation pin. In other examples, bone preparation guide 150 does not include stabilization members and/or has a different configuration than that specifically illustrated. Details on example bone realignment instruments and techniques that can be used in conjunction with the present disclosure are described in U.S. Pat. No. 9,622,805, issued Apr. 18, 2017 and entitled "BONE POSITIONING AND PREPARING GUIDE SYSTEMS AND METHODS" the entire contents of which are incorporated herein by reference.

Figure 9:
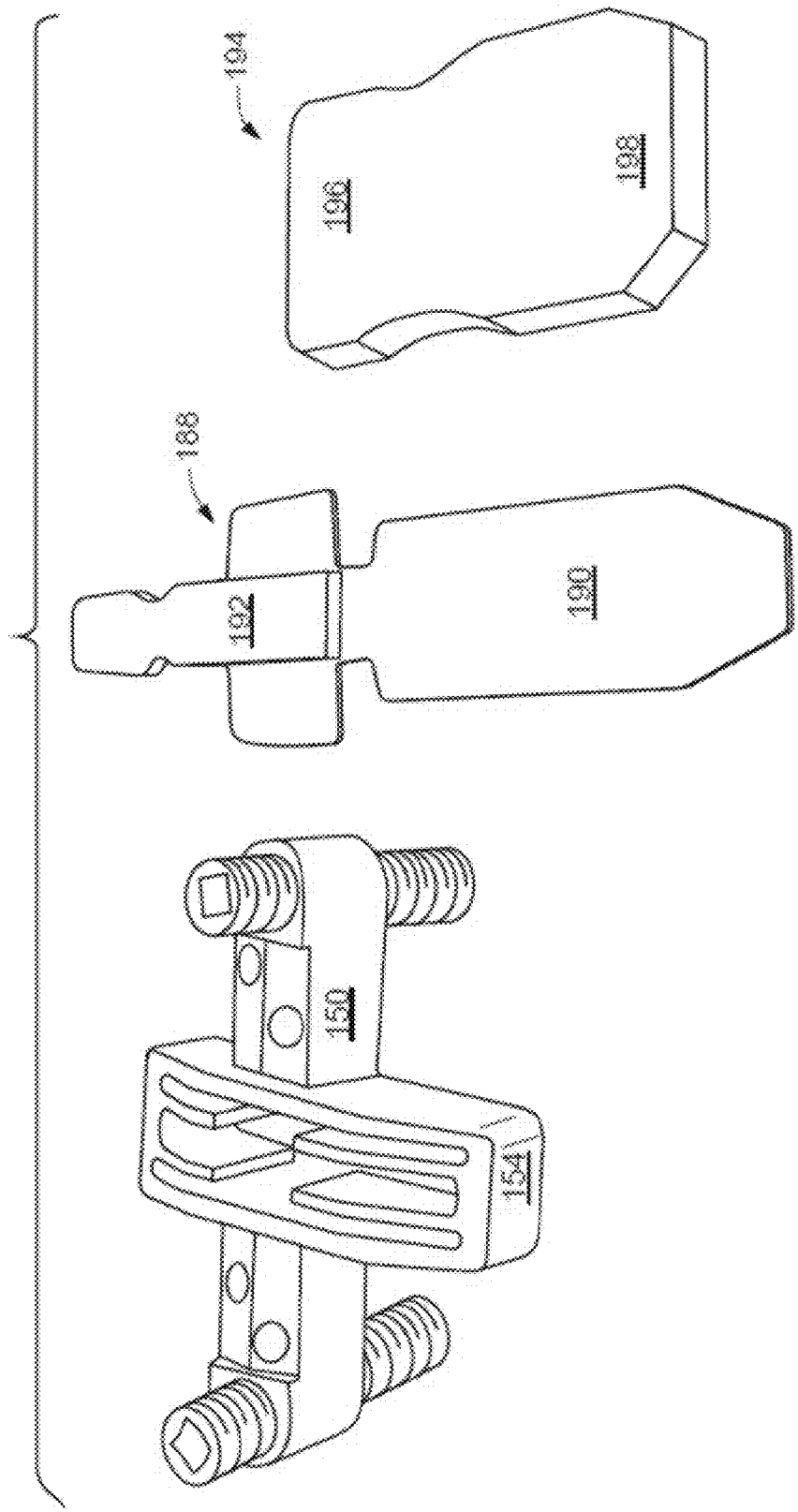
FIG. 9 illustrates example instrumentation that may be used with the example bone preparation guide of FIG. 8.

With reference to FIG. 9, bone preparation guide 150 may include or be used with a spacer 188 that extends downward from the body 154. Spacer 188 may be configured to be placed into a joint (e.g., within the TMT joint). In some embodiments, the spacer 188 is selectively engageable with the body of the bone preparation guide and removable therefrom. The spacer can have a first portion 190 configured to extend into a joint space and a second portion 192 engageable with the body 154. In the embodiment shown, the spacer can be received within opening 170, such that the spacer extends from the body in between the first and second guide surfaces. Such a spacer can be useful for positioning the body at a desired position with respect to a joint and for properly positioning the guide with respect to bones to be cut. The distance between the spacer and the first guide surface can define a length of tissue removal (e.g., bone or cartilage to be cut) from a first bone, and the distance between the spacer and the second guide surface can define a length of tissue removal (e.g., bone or cartilage to be cut) from a second bone.

When configured with spacer 188, the spacer can be inserted into TMT joint 230 after making incision 400. After inserting spacer 188 into the TMT joint, opening 170 of bone preparation guide 150 can be aligned with the spacer and the bone preparation guide installed one the spacer, thereby positioning the one or more guide surfaces defined by the bone preparation guide over one or more bone ends to be prepared. In other examples, spacer 188 may be engaged with bone preparation guide 150 prior to installation in TMT joint 230 and the spacer thereafter inserted into the joint as an assembly connected to the bone preparation guide. In still other examples, spacer 188 may be integrally and permanently attached to bone preparation guide 150 or the bone preparation guide may not include a spacer.

As also shown in FIG. 9, bone preparation guide 150 may include or be used with a tissue removal location check member 194. Tissue removal check member 194 may be engageable with the body 154 and configured to extend to a first bone and a second bone. The tissue removal location check member can have a first portion 196 configured to extend into contact with first and second bones and a second portion 198 engageable with the body. In the embodiment shown, the tissue removal check member 194 is configured to extend in the body 154 at both the first and second guiding surfaces. The tissue removal location check member 194 may be useful for allowing a practitioner to see where a tissue removing instrument guided by the surfaces will contact the bone to be prepared.

In addition to or in lieu of using a spacer, the systems and techniques according to the disclosure may utilize a fulcrum. A fulcrum may be a device positionable between the proximal base of the metatarsal being moved (e.g., first metatarsal 210) and an adjacent metatarsal (e.g., second metatarsal 212). The fulcrum can establish and/or maintain space between adjacent bones being moved, preventing lateral translation or base shift of the bones during rotation and/or pivoting.

When used, the fulcrum may be a standalone instrument or may be coupled to spacer 188 to define a bi-planar instrument. A bi-planar instrument can define a spacer body coupled to a fulcrum body that may be useful to provide a unitary structure (e.g., prior to or after being assembled) that can be positioned between two adjacent, intersecting joint spaces: a first joint space between opposed ends of a metatarsal and cuneiform and an intermetatarsal space between adjacent metatarsals. The spacer body can include a first portion insertable into the joint space and a second portion that projects above the joint space. The second portion projecting above the joint space can be coupled to a bone preparation guide, thereby facilitating positioning of the bone preparation guide over the metatarsal and/or cuneiform between which the spacer body is positioned. The fulcrum body can establish and/or maintain space between adjacent bones being moved, preventing lateral translation or base shift of the bones during rotation and/or pivoting.

Figure 10:
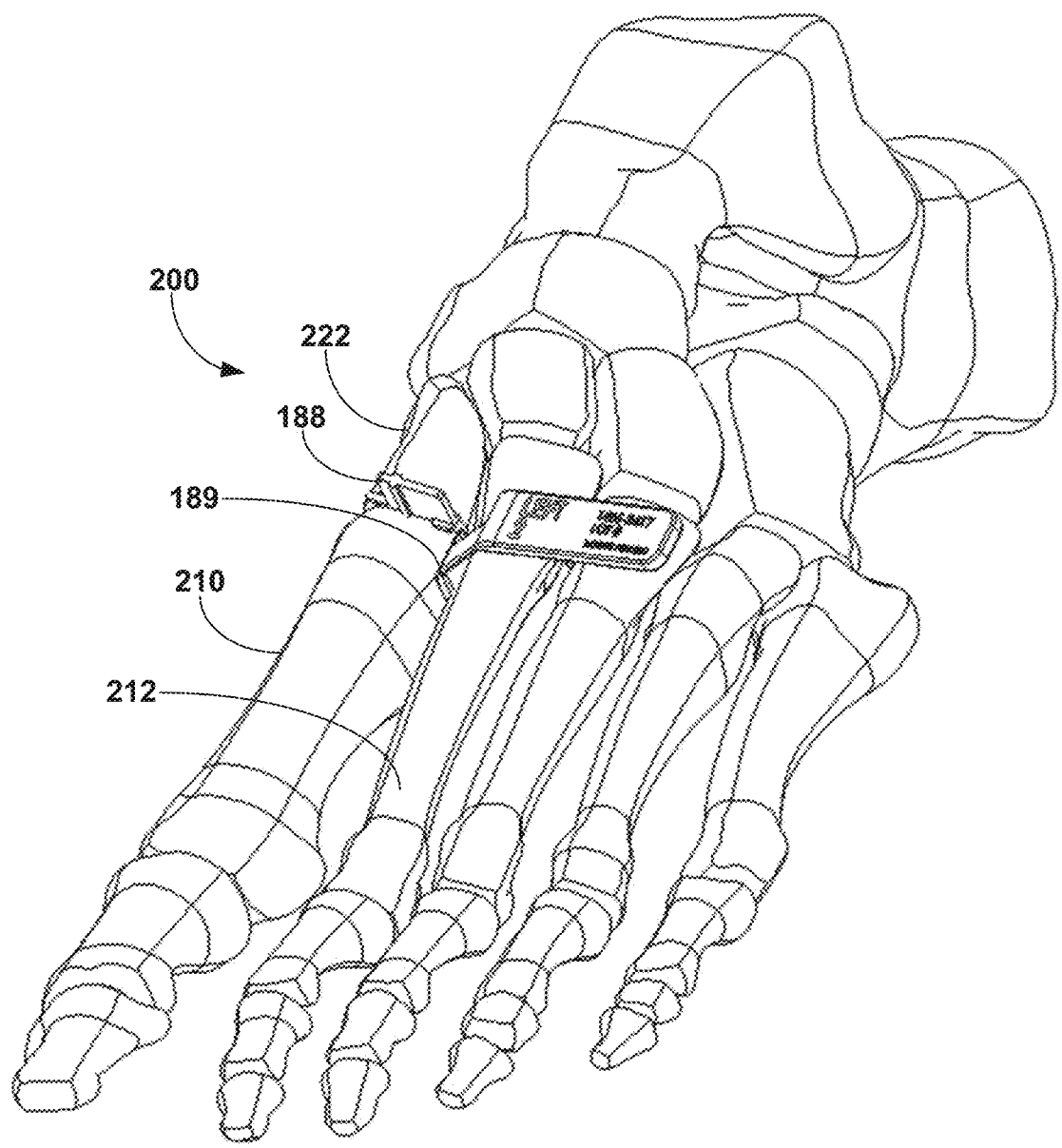
FIG. 10 is a perspective view of an example foot in which a bi-planar instrument is positioned in adjacent joint spaces.

FIG. 10 is a perspective view of an example foot 200 in which a bi-planar instrument is positioned in a first joint space and an intersecting second joint space, where a bone forming the first and second joint spaces is being realigned relative to one or more adjacent bones. In particular, FIG. 10 illustrates a bi-planar instrument having a spacer body 188 coupled to a fulcrum body 189. Spacer body 188 is positioned at an intersection between an end of first metatarsal 210 and medial cuneiform 222. Fulcrum body 189 is positioned between first metatarsal 210 and second metatarsal 212.

With further reference to FIG. 4, either before or after preparing one or both ends of first metatarsal 210 and medial cuneiform 222, the clinician may move the metatarsal in at least one plane (306). For example, the clinician may move metatarsal 210 in at least the transverse plane to close an intermetatarsal angle between the metatarsal and an adjacent bone (e.g., a second metatarsal) and/or a frontal plane (e.g., to reposition the sesamoid bones substantially centered under the metatarsal). In some examples, the clinician moves the bone portion in multiple planes, such as the transverse plane and/or frontal plane and/or sagittal plane. The clinician may or may not utilize a bone positioning device to facilitate movement of the bone portion.

Figure 11:
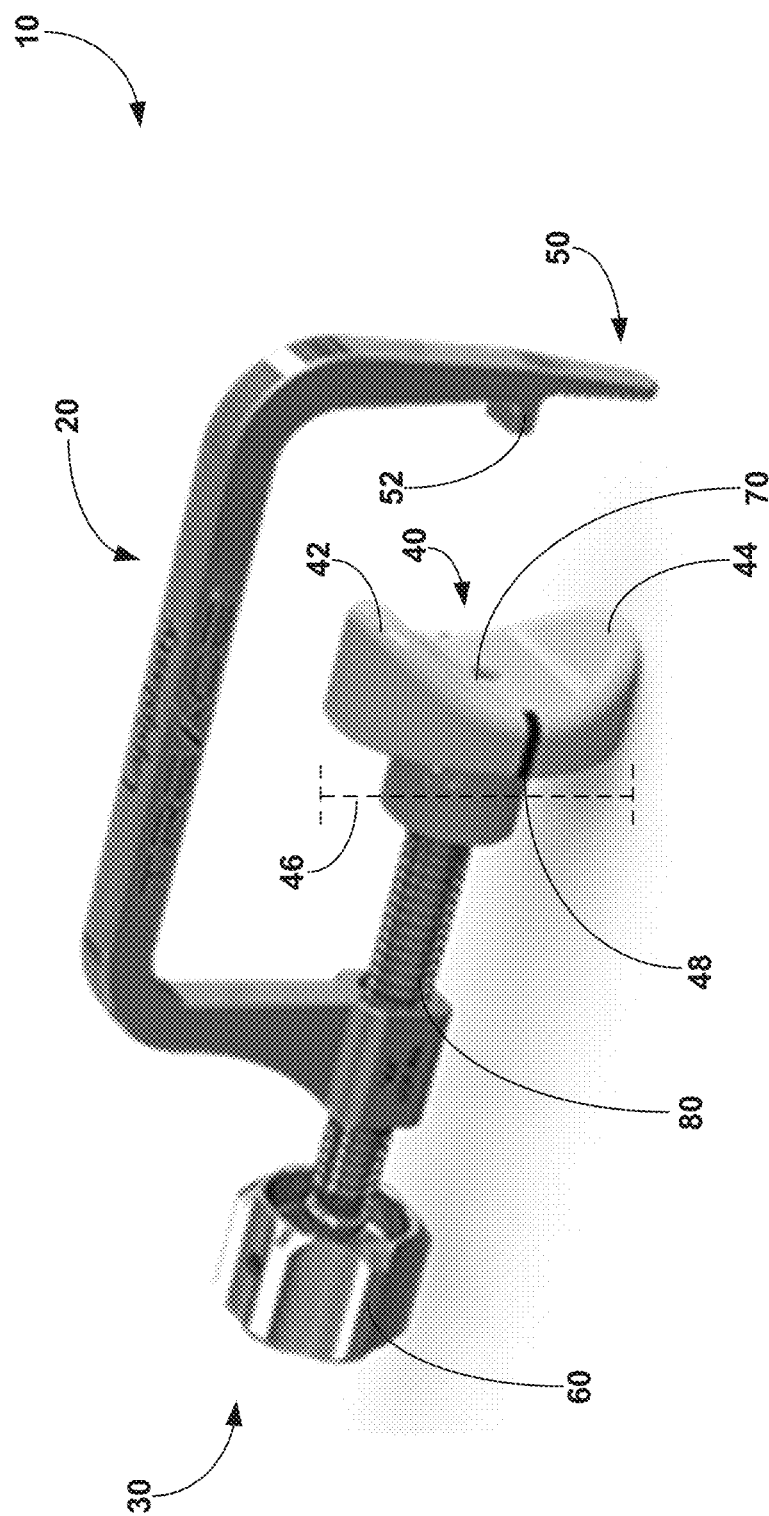
FIG. 11 shows a side perspective view of an example bone positioner that can be used to move a metatarsal relative to an adjacent bone.

FIG. 11 shows a side perspective view of an example bone positioner 10 (also referred to as a bone positioning device) that can be used to move a metatarsal relative to an adjacent bone. In some implementations, the bone positioning device includes a metatarsal engagement member, a tip, and a mechanism to move the metatarsal engagement member and the tip relative to each other in one or more planes. For example, the mechanism may move the metatarsal engagement member and the tip towards each other (e.g. moving the metatarsal engagement member towards the tip, moving the tip towards the metatarsal engagement member, or moving both simultaneously). The bone positioning device may also include an actuator to actuate the mechanism. When the mechanism engaged, it can cause the metatarsal engaged with the metatarsal engagement member to move to correct an alignment in at least one plane with respect to a second bone in contact with the tip.

In the embodiment of FIG. 11, bone positioning device 10 includes a main body member 20, a shaft 30, a metatarsal engagement member 40 is connected to the shaft, and a tip 50 is connected to the main body member. In general, main body member 20 can be sized and shaped to clear anatomy or other instrumentation (e.g., pins and guides) while positioned on a patient. In the embodiment of FIG. 11, the main body member 20 includes a generally C-shaped. In some embodiments, the main body is sized and configured to engage bones of a human foot. In addition, although bone positioning device 10 is illustrated as being formed of two components, main body member 20 and shaft 30, the guide can be fabricated from more components (e.g., three, four, or more) that are joined together to form the guide.

A shaft 30 can be movably connected to the main body member 20. In some embodiments, the shaft 30 includes threads 80 that engage with the main body member 20 such that rotation of the shaft translates the shaft with respect to the main body member. In other embodiments, the shaft can slide within the main body member and can be secured thereto at a desired location with a set screw. In yet other embodiments, the shaft can be moved with respect to the main body by a ratchet mechanism or yet other mechanism that rotates and/or linearly translates metatarsal engagement member 40 relative to tip 50. In the embodiment shown, the shaft moves along an axis that intersects the tip 50. In other embodiments, the shaft 30 and/or metatarsal engagement member 40 is offset from tip 50.

In general, metatarsal engagement member 40 is configured (e.g., sized and/or shaped) to be positioned in contact with an external surface of the skin 402 of the patient. As a result, force applied to and/or through metatarsal engagement member 40 is directed through the skin to the underlying metatarsal 210 rather than directly to the metatarsal. As a result, metatarsal engagement member 40 may be positioned against the skin of the patient without making an incision to facilitate direct contact between the metatarsal engagement member 40 and metatarsal 210.

Figure 12:
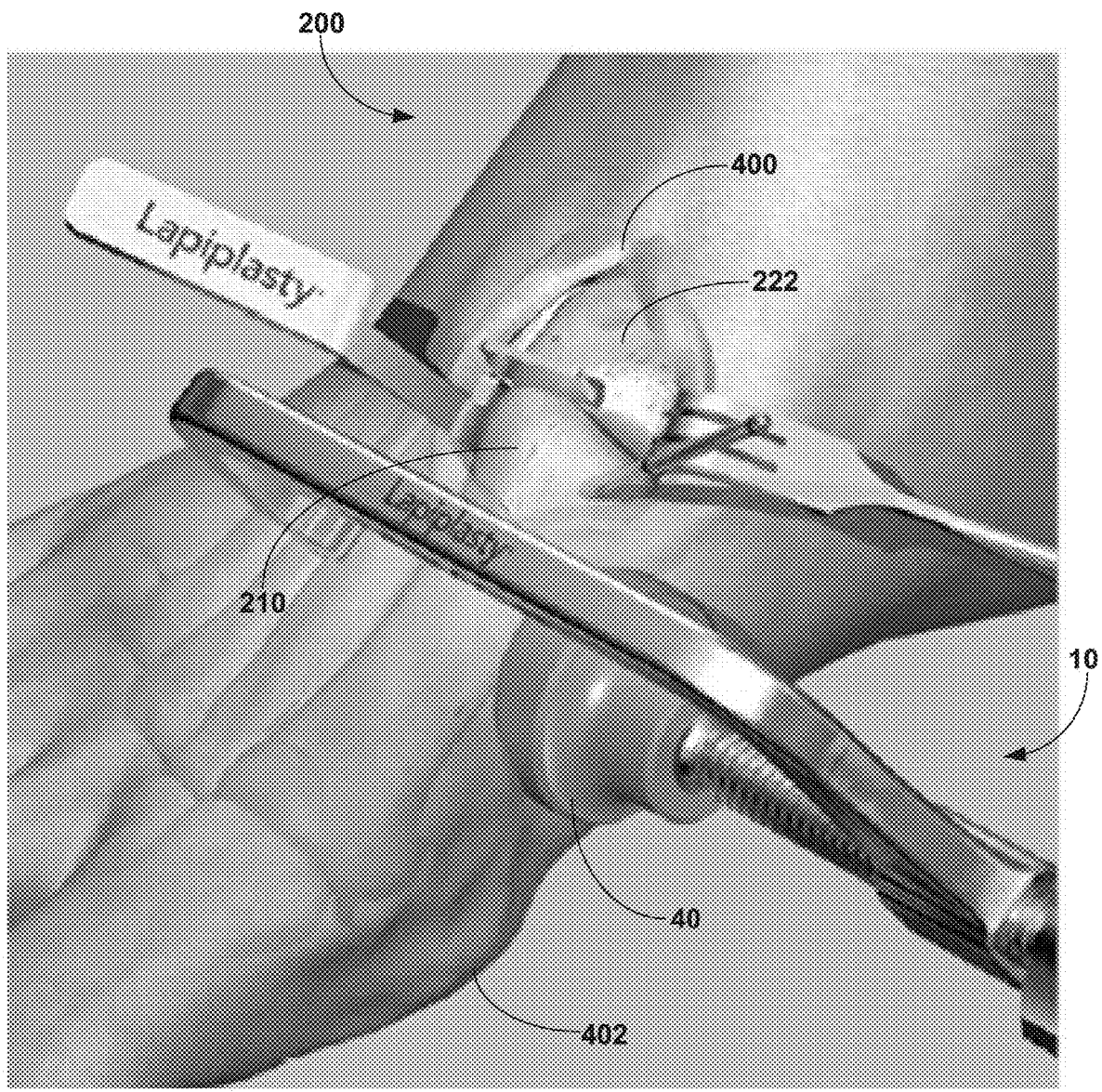
FIG. 12 is an illustration showing an example arrangement of the bone positioning device of FIG. 11 in which a metatarsal engagement member is positioned in contact with the external surface of the skin of the patient covering a side of a metatarsal.

FIG. 12 is an illustration showing an example arrangement of bone positioning device 10 in which metatarsal engagement member 40 is positioned in contact with the external surface of skin 402 of the patient covering a side of metatarsal 210. Bone positioning device 10 can apply a force to move metatarsal 210 through skin 402 in one or more planes. In the illustrated configuration, metatarsal engagement member 40 is positioned in contact with the external surface of skin 402 of the patient covering a medial side of metatarsal 210. For example, metatarsal engagement member 40 may be positioned in contact with a portion of skin that covers the medial-most half of metatarsal 210. This arrangement is useful, e.g., to move metatarsal 210 laterally to close the IMA between first metatarsal 210 and second metatarsal 212. In other configurations, the metatarsal engagement member 40 may be positioned in contact with the external surface of skin 402 of the patient covering a different portion of metatarsal 210. In still further implementations, the techniques of the disclosure may be performed without a bone positioning device or a bone positioning device that contacts metatarsal 210 directly rather than through skin 402. However, configuring bone positioning device 10 to deliver movement force through skin 402 can help facilitate a minimal incision procedures.

With further reference to FIG. 11, metatarsal engagement member 40 may be configured (e.g., sized and/or shaped) to contact skin overlying an underlying bone (e.g., first metatarsal 210). Metatarsal engagement member 40 may define a concave shape to generally conform and/or wrap partially around the underling cylindrical bone. The concave shape may include define a continuous radius of curvature, a V-shape, a planer region between outwardly extending sidewalls, and/or other shape having a concavity. In still other examples, metatarsal engagement member 40 may be planar. In either case, when configured with a concave shape, the bottom of the concavity can be centered between outwardly extending sidewalls 42, 44. Each sidewall can extend outward to the same height and/or at the same slope, or may extend to different heights and/or at different slopes.

While the specific dimensions of metatarsal engagement member 40 may vary depending on the manufacturer and/or user preferences, in some examples, the metatarsal engagement member may have a length sufficient at least partially conform around the skin-covered surfaces of the metatarsal being moved (e.g., first metatarsal 210). For example, metatarsal engagement member 40 may have a length 46 extending in a dorsal to plantar direction (when positioned in contact with a patient) that is at least 20 mm, such as at least 25 mm, at least 28 mm, at least 30 mm, or at least 35 mm. For example, the length 46 may range from 28 mm to 35 mm.

To help position bone positioning device 10 in the sagittal plane when installing on a patient's foot, metatarsal engagement member 40 may include a center line indicator 48. The center line indicator 48 may be a visual indicator (e.g., line) indicating a geometric center of metatarsal engagement member 40 between the dorsal and plantar ends of the metatarsal engagement member. In use, the clinician may substantially align center line indicator 48 with a midpoint (e.g., geometric center between the dorsal and plantar surfaces) of the metatarsal being moved (with the midpoint being covered by skin 402). The clinician may identify the midpoint by visual and/or tactile inspection and/or through radiographic (e.g., fluoroscopic) imaging. Additionally or alternative, the clinician can mark (with a surgical pen) the midpoint on the skin as a reference for alignment. Alignment of the metatarsal engagement member can then occur by aligning the center indicator mark to the marked midpoint of the metatarsal.

In the embodiment shown, the metatarsal engagement member 40 is provided on an end of the shaft 30. In the embodiment of the shaft shown having threads 80, the metatarsal engagement member 40 can be rotatably coupled to the shaft 30. In such embodiments, as the shaft is rotated relative to the main body member the metatarsal engagement member 40 may or may not rotate with respect to the main body member even as it translates with respect to the main body member along with the shaft 30 and rotates with respect to the shaft. The metatarsal engagement member may oscillate about the shaft 30, but generally does not rotate with respect to skin 402 and/or underlying bone after contact with the skin.

Tip 50 can be useful for contacting a bone, such as a bone different than the bone being moved by bone positioning device 10. For example, if metatarsal engagement member 40 is in contact with skin covering first metatarsal 210, the tip can be in contact with a lateral side of a different metatarsal (e.g., the second, third, fourth, or fifth metatarsal) and/or a lateral side of skin covering such metatarsal. In some examples, a small stab incision may be made between the different metatarsal and a laterally-adjacent metatarsal. For example, a stab incision may be made in an intermetatarsal space between the second metatarsal 212 and third metatarsal 214. Tip 50 of bone positioning device 10 can be inserted through the incision and the tip positioned in contact with the lateral side of the second metatarsal.

In different configurations, tip 50 may be straight or may be tapered to facilitate percutaneous insertion and contact with bone. The tip can also include a textured surface, such as serrated, roughened, cross-hatched, knurled, etc., to reduce slippage between the tip and bone. In the embodiment shown, tip 50 further includes a stop 52. Depth stop 52 can limit a depth of insertion into an intermetatarsal space (e.g., by contacting a dorsal surface of the metatarsal against which tip 50 is intended to be positioned).

As shown in FIG. 11, bone positioning device 10 can also include an actuator (e.g., a knob or a handle) 60 to actuate the mechanism, in this embodiment associated with the shaft. In the embodiment shown, the actuator can be useful for allowing a user to rotate the shaft with respect to the main body member 20. Actuator 60, shaft 30, and/or metatarsal engagement member 40 may include a cannulation 70 extending therethrough to allow the placement of a fixation wire (e.g., K-wire) through these components and into contact with or through a bone engaged with the metatarsal engagement member. For example, a fixation wire can be placed into the bone engaged with metatarsal engagement member 40 to fix the position of the metatarsal engagement member with respect to the bone. In another example, the fixation wire can be placed through the bone in contact with the metatarsal engagement member and into an adjacent bone to maintain a bone position of the bone in contact with the metatarsal engagement member and the adjacent bone.

Embodiments of the bone positioning device may include any suitable materials. In certain embodiments, the bone positioning device is fabricated at least partially from a radiolucent material such that it is relatively penetrable by X-rays and other forms of radiation, such as thermoplastics and carbon-fiber materials. Such materials are useful for not obstructing visualization of bones using an imaging device when the bone positioning device is positioned on bones.

Figure 13:
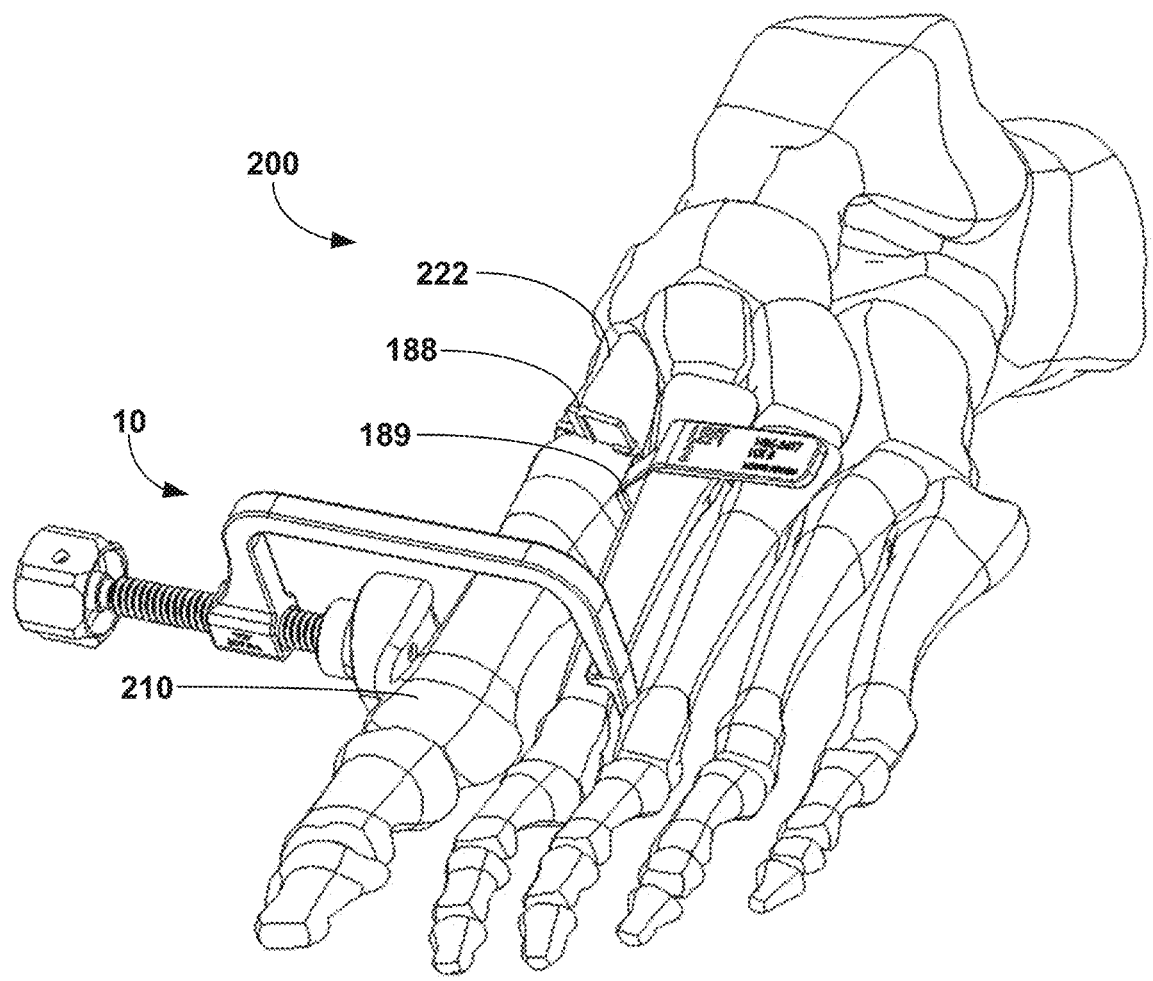
FIG. 13 is a perspective view of a foot showing a seeker and a fulcrum inserted between adjacent joint spaces and a bone positioner engaged with a first metatarsal.
Figure 14:
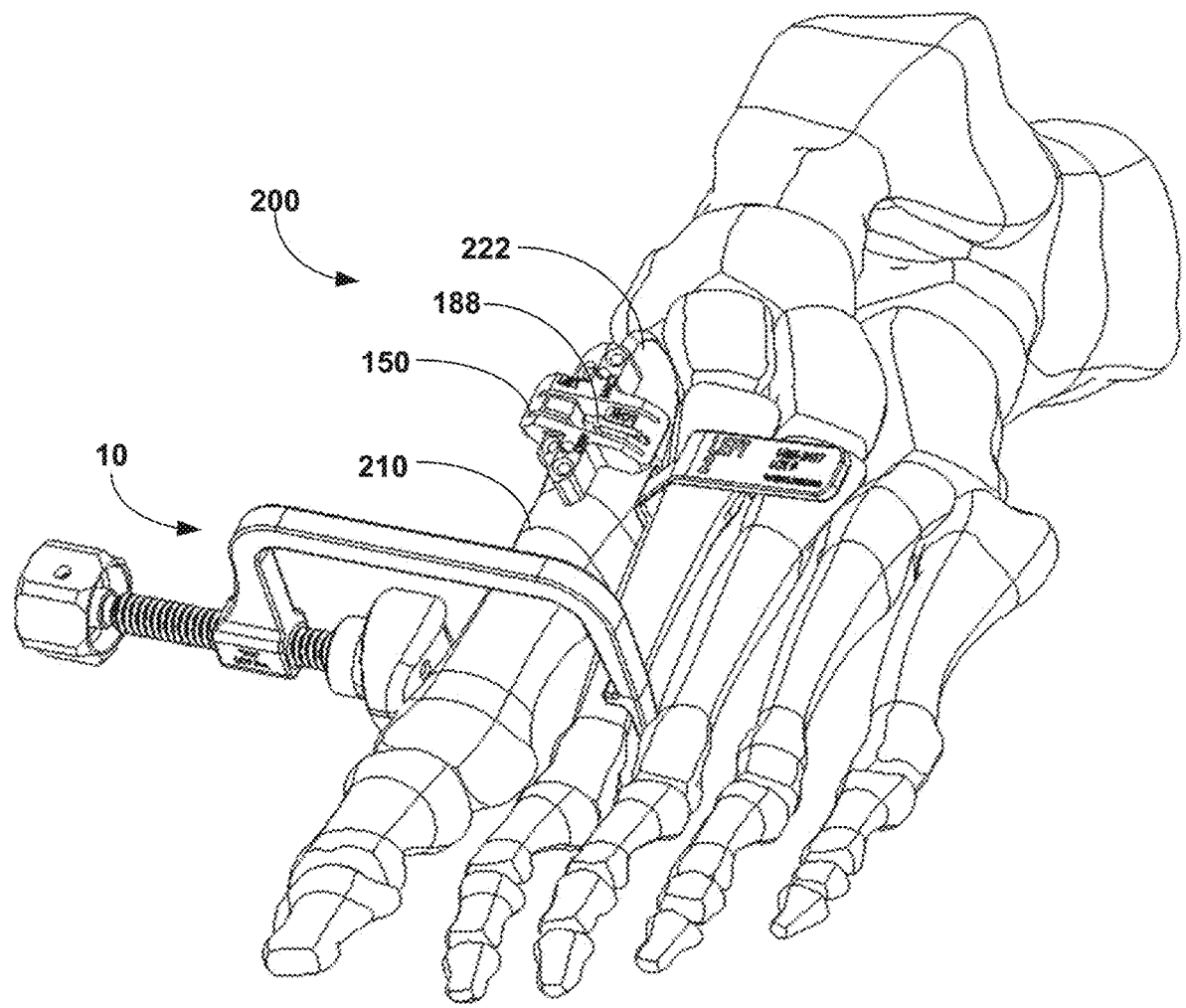
FIG. 14 is a perspective view of the foot from FIG. 13 further illustrated with a bone preparation guide installed on the seeker.
Figure 15:
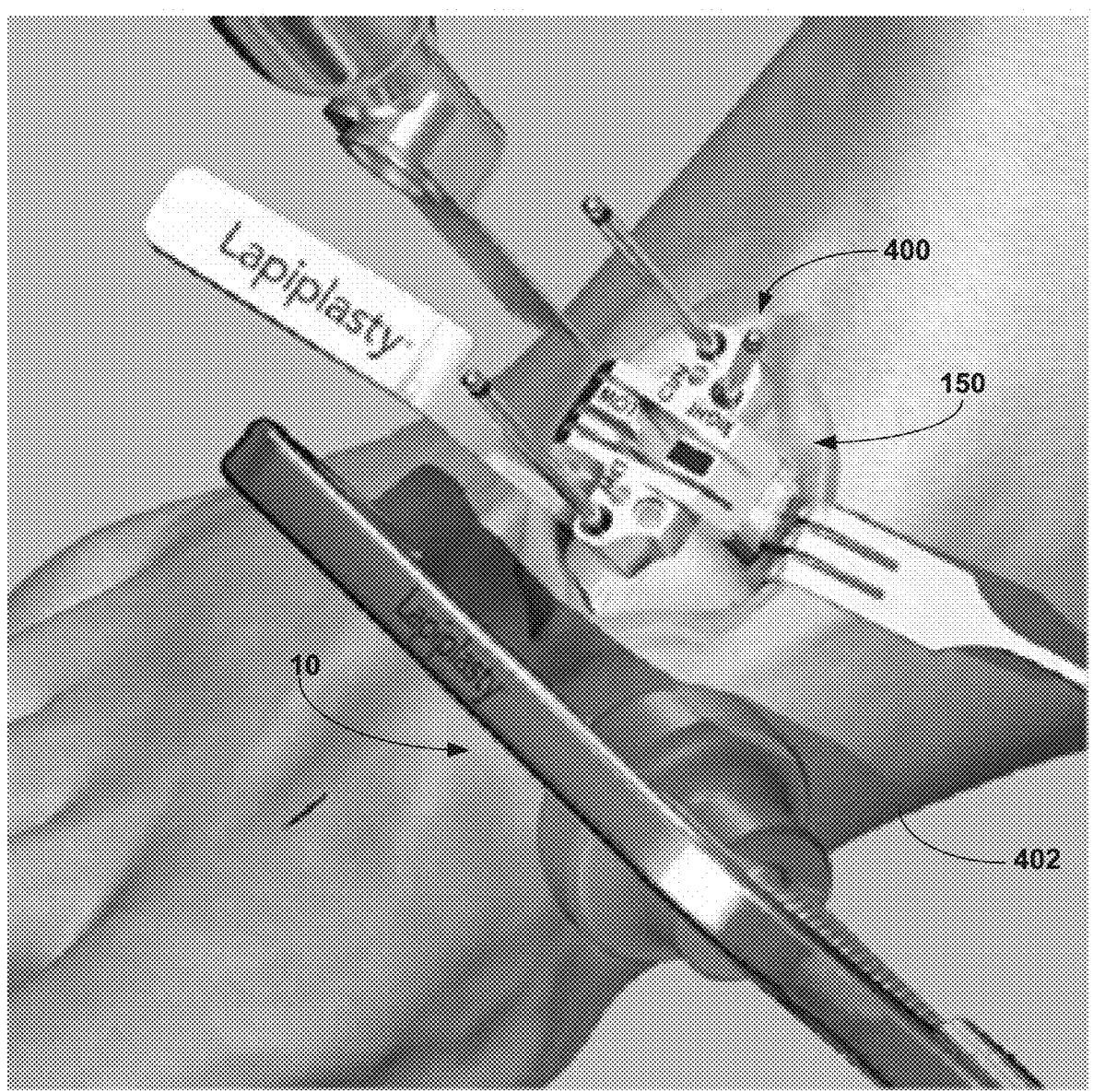
FIG. 15 is a further illustration of the surgical instrument arrangement of FIG. 14 showing the example location of an incision and skin of the patient relative to the surgical instruments.

FIG. 13 is a perspective view of foot 200 showing seeker 188 and fulcrum 189 inserted between adjacent joint spaces and bone positioner 10 engaged with first metatarsal 210. FIG. 14 is a perspective view of foot 200 from FIG. 13 further illustrated bone preparation guide 150 installed on seeker 188. In different examples, bone positioner 10 may be installed before and/or after installing bone preparation guide 150 and/or before or after preparing one or both bone ends. FIG. 15 is a further illustration of the surgical instrument arrangement of FIG. 14 showing the example location of incision 400 and skin 402 relative to the surgical instruments.

Independent of whether the clinician utilizes a bone positioning device or the configuration of such guide, the clinician can move metatarsal 210 in one or more planes. The clinician may move the metatarsal to help correct an anatomical misalignment of the metatarsal. For example, the clinician may move the metatarsal so the metatarsal is anatomically aligned in one or more planes (e.g., two planes, three planes).

In some examples, the clinician manually moves first metatarsal 210 in addition to or moving the metatarsal through a force applied by bone positioner 10. For example, the clinician may grasp a pin inserted into the first metatarsal and/or grasp the metatarsal with a tool (e.g., forceps) and manipulate the position of the metatarsal to a desired position. In some applications, bone positioner 10 may apply a force the moves first metatarsal 210 in the transverse plane to close the IMA with an adjacent metatarsal. However, the amount of frontal plane rotation and/or sagittal plane movement achieved by bone positioner 10 through the skin of the patient may be limited. Accordingly, the clinician may manually move first metatarsal 210 (e.g., by grasping a pin inserted into the metatarsal and at least partially projecting out of the metatarsal) to rotate the metatarsal in the frontal plane and/or move the metatarsal in the sagittal plane.

In general, an anatomically aligned position means that an angle of a long axis of a first metatarsal relative to a long axis of a second metatarsal is about 10 degrees or less in the transverse plane or sagittal plane. In certain embodiments, anatomical misalignment can be corrected in both the transverse plane and the frontal plane. In the transverse plane, a normal intermetatarsal angle ("IMA") between a first metatarsal and a second metatarsal is less than about 9 degrees. An IMA of between about 9 degrees and about 13 degrees is considered a mild misalignment of the first metatarsal and the second metatarsal. An IMA of greater than about 16 degrees is considered a severe misalignment of the first metatarsal and the second metatarsal. In some embodiments, the first metatarsal is moved to reduce the IMA from over 10 degrees to about 10 degrees or less (e.g., to an IMA of about 1-5 degrees), including to negative angles of about −5 degrees or until interference with the second metatarsal, by positioning the first metatarsal at a different angle with respect to the second metatarsal.

With respect to the frontal plane, a normal first metatarsal will be positioned such that its crista prominence is generally perpendicular to the ground and/or its sesamoid bones are generally parallel to the ground and positioned under the metatarsal. This position can be defined as a metatarsal rotation of 0 degrees. In a misaligned first metatarsal, the metatarsal is axially rotated between about 4 degrees to about 30 degrees or more. In some embodiments, methods in accordance with the invention are capable of anatomically aligning the metatarsal by reducing the metatarsal rotation from about 4 degrees or more to less than 4 degrees (e.g., to about 0 to 2 degrees) by rotating the metatarsal with respect to the medial cuneiform.

In some applications, independent of whether the clinician performs the specific bone realignment technique discussed above, the clinician may compress the end faces of the prepared bones (e.g., first metatarsal 210, medial cuneiform 222) together. For example, the technique of FIG. 4 includes optionally compressing the prepared end faces of the bone portions together prior to fixating (308). The clinician may compress the end faces together with hand pressure and/or using a compressing instrument physically attached to both the first bone portion and the second bone portion. For instance, the clinician may attach a compressing instrument to metatarsal 210 with one or more fixation pins and also attach the compressing instrument to medial cuneiform 222 using one or more fixation pins. In some examples, the clinician lifts bone preparation guide off two or more pins that extend parallel to each other, at least one of which is inserted into metatarsal 210 and at least one of which is inserted into medial cuneiform 222. The clinician can then install a compressor back down on the parallel pins.

When used, the compressing instrument may have a mechanism (e.g., threaded rod, rack and pinion) that presses against the pins inserted through the two bone portions to compress the end faces of the two bone portions together. Additional details on example compressing instruments that may be used can be found in US Patent Publication No. 2020/0015856, published Jan. 16, 2020 and entitled "COMPRESSOR-DISTRACTOR FOR ANGULARLY REALIGNING BONE PORTIONS," the entire contents of which are incorporated herein by reference.

Figure 16:
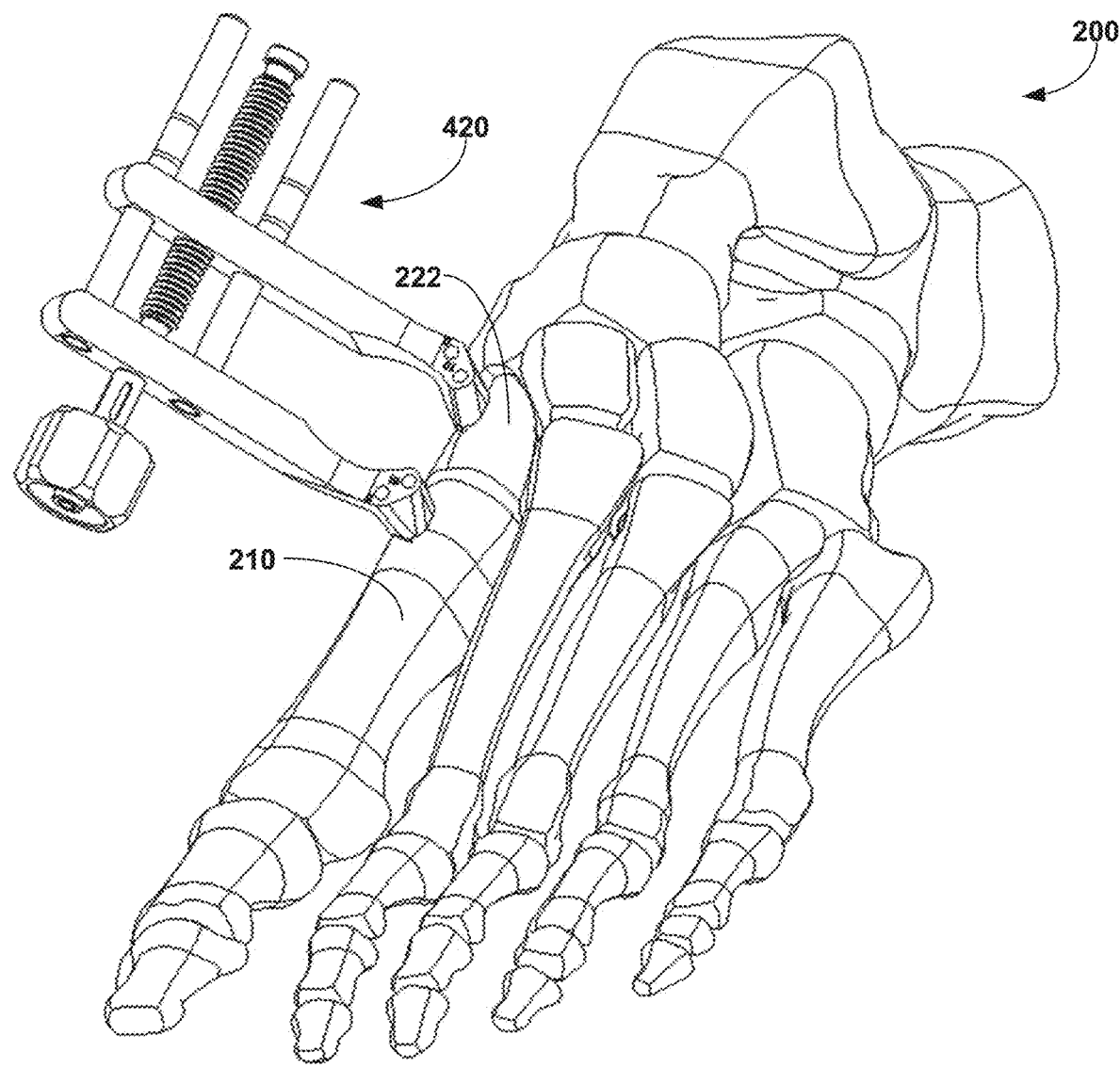
FIG. 16 is a perspective view of a foot illustrating an example compressing instrument that may be used to compress the prepared end faces of the metatarsal and medial cuneiform together.

FIG. 16 is a perspective view of foot 200 illustrating an example compressing instrument 420 that may be used to compress the prepared end faces of first metatarsal 210 and medial cuneiform 222 together. Compressing instrument 420 may be attached using at least one fixation pin inserted through an arm of the compressing instrument into first metatarsal 210 and using at least one fixation pin inserted through an arm of the compressing instrument into medial cuneiform 222.

In addition to or in lieu of compressing the prepared end faces of the bones together, the technique of FIG. 4 may involve temporarily or provisionally fixating a moved position of first metatarsal 210 relative to medial cuneiform 220 prior to attaching a permanent fixation device (310). In some implementations, the clinician inserts one or more fixation pins through first metatarsal 210 and into an adjacent bone (e.g., second metatarsal 212, medial cuneiform 222), such as through the end faces of the first metatarsal 210 and medial cuneiform 220 in addition to or in lieu of compressing the end faces with a compressing instrument. The fixation pin may be a k-wire, olive wire (e.g., pin with region of enlarged cross-section) or other fixation pin structure. The fixation pin crossing joint 230 between first metatarsal 210 and medial cuneiform 220 can help provisionally fixate and/or compress the end faces of the two bone portions together prior to installation of permeant fixation device (and subsequent fusion of the bone faces together). When used, the one or more fixation pins can be removed from the end faces of the two bone portions and across the joint between the bone portions after installation of permanent fixation device.

Independent of whether the clinician provisionally fixates the moved position of first metatarsal 210 relative to medial cuneiform 220, the technique of FIG. 4 involves installing one or more permanent fixation devices to first metatarsal 210 and medial cuneiform 220 across joint 230 (312). The one or more permanent fixation devices may hold the moved position of first metatarsal 210 relative to medial cuneiform 220, allowing the end faces of the bone portions to fuse together through a subsequent healing process.

Any one or more bone fixation devices can be used including, but not limited to, a bone screw (e.g., a compressing bone screw), a bone plate, a bone staple, an external fixator, a pin (e.g., an intramedullary implant), and/or combinations thereof. The bone fixation device may be secured on one side to metatarsal 210, bridge the TMT joint 230, and be secured on an opposite side to the proximal medial cuneiform 222

In one example, two bone plates may be placed across the TMT joint to provide bi-planar plating. For example, a first bone plate may be positioned on a dorsal side of the metatarsal and medial cuneiform. A second bone plate may be positioned on a medial/dorsal-medial side of the metatarsal and medial cuneiform. Independent of the number or configuration of bone plates, the plates may be applied with the insertion of bone screws.

A variety of different of different bone plate configurations can be used to permanently fixate a metatarsal to a cuneiform. In some examples, the bone plate is configured as a linear bone plate in which all the fixation holes extending through the bone plate are co-linear with each other. In other examples, the bone plate includes one or more fixation holes extending through one or more branch(es) that are non-co-linear with the remaining co-axially arranged fixation holes. For instance, in various examples, the bone plate may include at least one branch extending outwardly from a longitudinal axis of the bone plate to define at least one of a Y-shape, an L-shape, a T-shape, a U-shape, and/or other shape profile.

Figure 17:
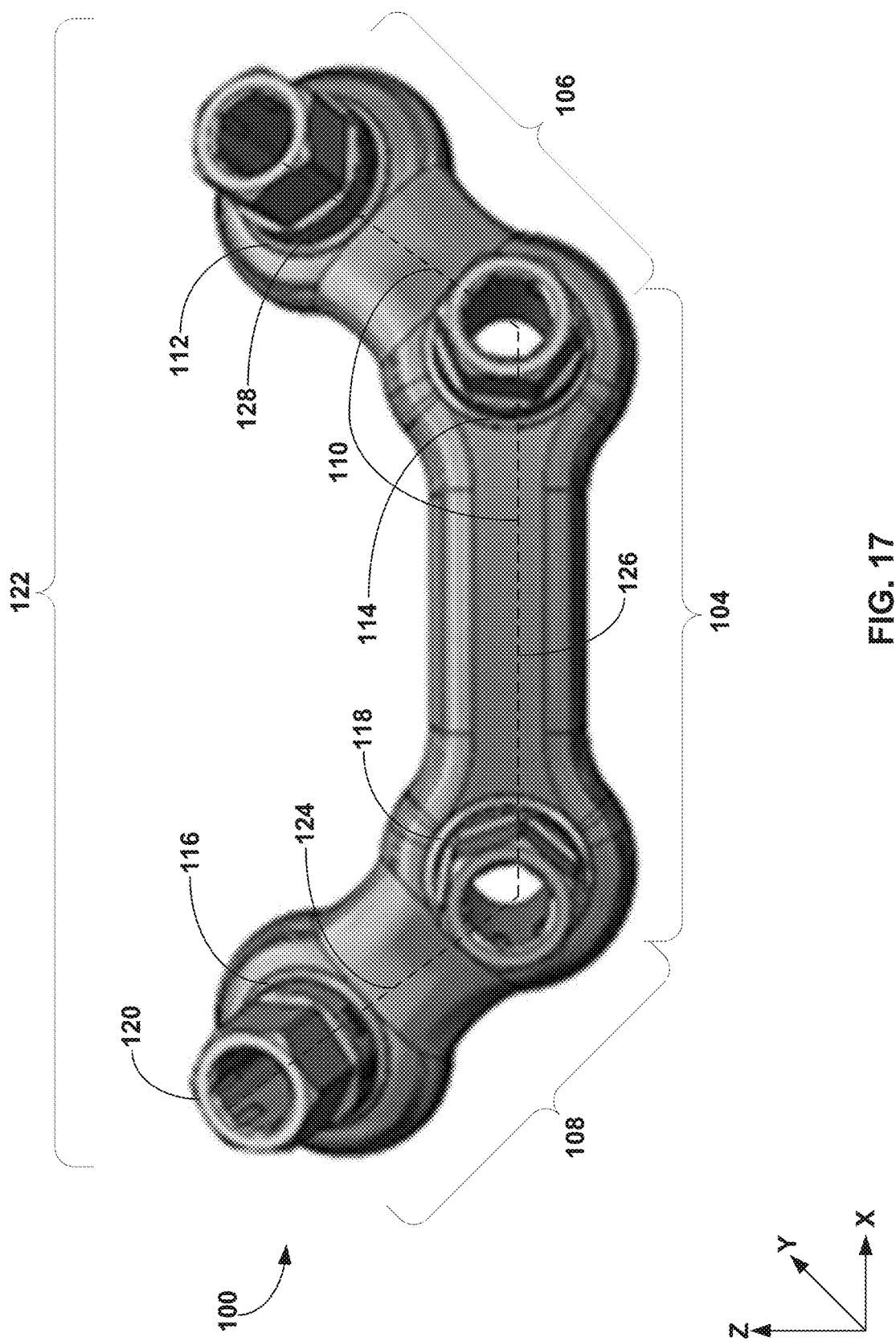
FIG. 17 is illustration of an example bone plate that can be used to help permanently fixate a moved position of a metatarsal relative to an opposed cuneiform.

FIG. 17 is illustration of an example bone plate 100 that can be used to help permanently fixate a moved position of a metatarsal relative to an opposed cuneiform. In particular, bone plate 100 illustrates an example bone plate having a U-shaped profile. Configuring bone plate 100 with a U-shaped profile can be useful to help facilitate a minimally invasive surgical procedure. Because of the comparatively short length of the surgical incision in such a procedure, installation of a straight fixation plate through the incision may result in one or more fixation holes being positioned under the skin of the patient and therefore inaccessible for the clinician to insert screws through the fixation holes. By configuring bone plate 100 with a shaped profile (e.g., U-shape), one or more fixation holes extending through the arm(s) of the U-shape may wrap into a region of the incision accessible by the clinician for inserting screws.

As shown in FIG. 17, bone plate 100 can have a body 102 defining a base 104, a first arm 106 extending at an angle from the base, and a second arm 108 extending at an angle from the base. The first and second arms 106, 108 may extend at the same angle away from base 104 or may extend at different angles. In some examples, the first and second arms 106, 108 each extend at an angle 110 from base 104 ranging from 30 degrees to 175 degrees, such as from 45 degrees to 150 degrees, or from 75 degrees to 135 degrees. For example, angle 110 may be greater than or equal to 90 degrees.

In either case, bone plate 100 may include one or more fixation holes extending through the thickness of body 102. In these examples, body 102 may include one or more fixation holes in first arm 106, one or more additional fixation holes in second arm 108, and base 104 may or may not include any fixation holes.

In the illustrated example, first arm 106 has at least one fixation hole, which is illustrated as two fixation holes 112 and 114. Second arm 108 also has at least one fixation hole, which is also illustrated as two fixation holes 116 and 118. Fixation hole 114 is at the intersection of first arm 106 and base 104. Fixation hole 118 is at the intersection of second arm 108 and base 104. Base includes a region between fixation holes 114 and 118 the forms a bridge devoid of any fixation holes, which can be placed bridging across TMT joint 230.

In the illustrated configuration, one or more drill guides 120 are threadingly inserted into one or more of the fixation holes. Drill guides 120 can provide a structure for guiding a drill to drill into the underlying bone (e.g., prior to inserting a screw). In some implementations, drill guides 120 may also be used to grasp plate 100 with a plate holder to manipulate the plate during placement.

Although bone plate 100 is illustrated as being configured with four fixation holes the bone plate may include fewer fixation holes or more fixation holes. For example, first arm 106 and second arm 108 of bone plate 100 may each include fewer fixation holes (e.g., one) and/or more fixation holes (e.g., three, four). The dimensions (e.g., length) of the arms and/or base can be adjusted to accommodate the particular number of fixation holes, among other factors.

Each feature described as a fixation hole may be an opening extending through the thickness of body 102 that is sized to receive a corresponding screw. Each fixation hole may typically have a circular cross-sectional shape although may have other cross-sectional shapes without departing from the scope of the disclosure. The fixation hole may extend perpendicularly through the thickness of body 102 or may taper (e.g., such that the hole is larger adjacent the top surface of the plate than adjacent the bone-facing surface of the plate). In still other examples, the fixation hole may extend at a non-perpendicular angle through the thickness of body 102 and/or be configured for polyaxial screw alignment. In either case, bone plate 100 can be secured to underlying bone portions by inserting fixation elements through corresponding fixation holes. Example fixation elements that can be used are screws, may be locking screws and/or non-locking screws.

When configured with a U-shape, bone plate 100 may define a maximum length 122 less than the combined length of the individual linear segments of the plate (e.g., the combine lengths 124, 126, and 128). In some examples, maximum length 112 is less than the length of incision 400 whereas the combined length of the individual linear segments of the plate may have a length greater than the length of incision 400. As a result, fixation holes (e.g., 112, 116) that be positioned at a location accessible through incision 400 when bone plate 100 is configured with a U-shape but may otherwise be inaccessible if the same place is reconfigured as a linear bone plate.

Access may be particularly challenging when the clinician positions the bone plate at a location offset from the incision location. For example, the clinician may position the base of the U-shaped bone plate at location that is offset at least 45 degrees from the center of the incision, such as at least 60 degrees, at least 75 degrees, or approximately 90 degrees or more. For instance, the clinician may make a dorsal incision and position the base of the U-shaped bone plate on a medial side of the TMT joint. The clinician may position the base of the bone plate across the TMT joint with the legs extending upwardly in a dorsal direction relative to the base.

Figure 18:
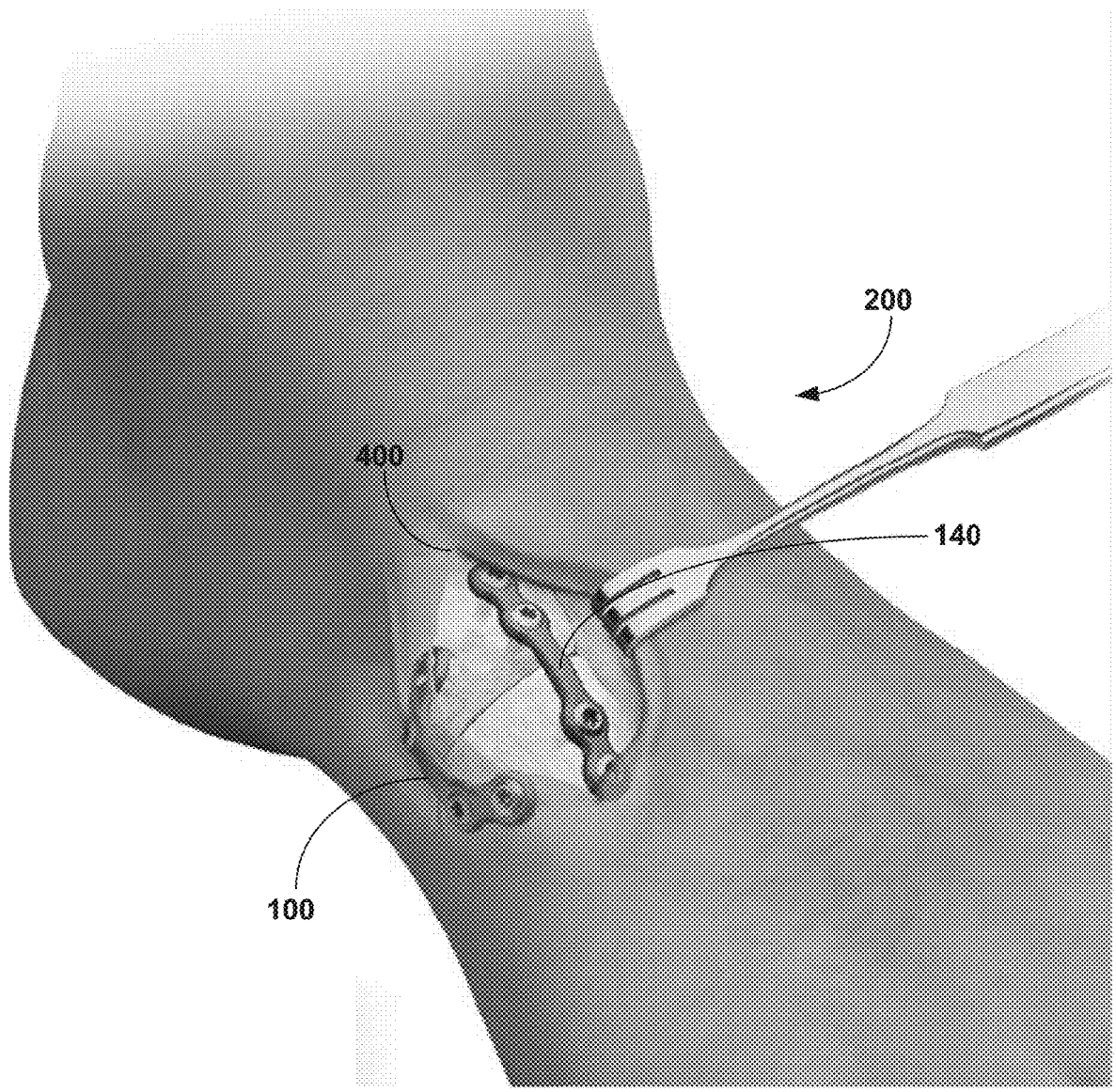
FIG. 18 is a perspective view of a foot showing an example insertion location of the bone plate of FIG. 17.

FIG. 18 is a perspective view of foot 200 showing an example insertion location of bone plate 100. As shown in this example, the arms of U-shaped bone plate wrap into region accessible by through incision 400. In this example, a second bone plate 140 that has a linear profile is attached on a dorsal side of the metatarsal and cuneiform, across the TMT joint.

To install bone plate 100 (or another bone plate) in a minimal incision procedure, the clinician may utilize a plate holder to help manipulate and/or hold the bone plate within the incision. The plate holder may be an instrument configured to releasably grasp an external surface of the plate and/or be inserted into a fixation hole of the plate, such as a drill guide inserted through the fixation hole. Using the plate holder, the clinician may be able to controllably and precisely position the bone plate and/or hold the bone plate during installation of one or more screws in the small incision created to access the TMT joint space. This can help address space constrains caused by the comparatively small length incision, which can make it difficult for the clinician to properly position the bone plate using their fingers along.

In general, a plate holder may be any instrument that can be releasably connected to a bone plate to help facilitate installation of the bone plate and then detached after and/or during installation. In various examples, the plate holder may be operatively coupled to an exterior surface of the bone plate (e.g., by grasping a protrusion from the plate and/or opposed sides of the plate) and/or an interior surface of the bone plate (e.g., by inserting into one or more fixation holes of the bone plate). Further purposes of installation, when one or more drill guides 120 are inserted into the fixation holes of the bone plate, the drill guides may be considered part of the bone plate that the plate holder can grasp and/or be inserted into.

FIG. 19 illustrates one example plate holder 450 that is configured as a tenaculum or forceps-style plate holder. In this example, plate holder 450 includes a first arm 452 and a second arm 454 that are pivotably connected together. Each arm extends from a proximal end 456 to a distal end 458. The distal end of each arm may be linear or, as illustrated, may be curved to define opposed converging radiuses of curvature. When so configured, the arms may be engaged with (e.g., wrapped at least partially about) a feature of bone plate 100. As illustrated, arms 452, 454 are wrapped around drill guides 120 inserted into fixation holes of the bone plate. In other examples, the bone plate may include a feature (e.g., a recess, cavity, projection) that one or both arms 452, 454 can be operatively engaged with (e.g., when the tenaculum is closed) to releasably secure the plate holder to the bone plate. In some examples, plate holder 450 includes a locking mechanism (e.g., ratchet, set screw, etc.) that can lock the arms 452, 454 at a fixed position (e.g., when grasping plate 100) but be released by the clinician to remove the plate holder from the plate.

FIG. 20 illustrates another example plate holder 470 configured to releasably attached to one or more drill guides 120 inserted into one or more fixation holes of a bone plate, such as bone plate 100. Plate holder 470 may include a handle 472 connected to a body defining one more slots and/or apertures 474 into which a drill guide 120 can be inserted to releasably attach the bone plate to the plate holder.

Figure 21:
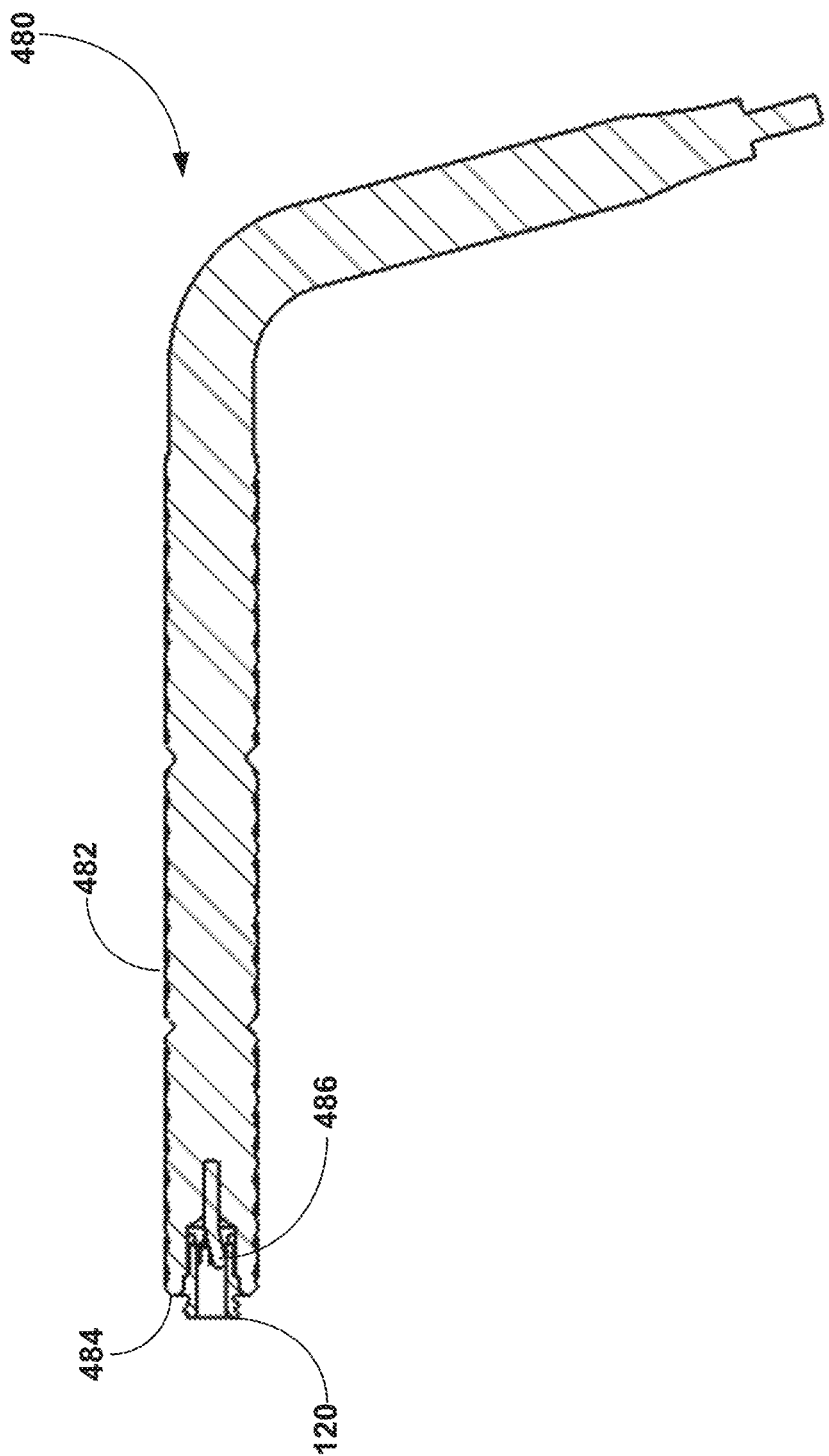

FIG. 21 illustrates another example plate holder 480 that is configured as a plate bender-style plate holder. In this example, plate holder 480 defines a shaft 482 terminating in a distal end 484. In different configurations, the distal end 484 of shaft 482 can be configured (e.g., sized and/or shaped) to be inserted into a fixation hole of a bone plate and/or drill guide 120 inserted into the fixation hole and/or to be inserted over an exterior surface of the drill guide (as illustrated in FIG. 21). In some examples, plate holder 480 may include a retention mechanism 486, such as a spring, clasp, O-ring, or other device to provide frictional engagement between the plate holder and bone plate (e.g., drill guide inserted into the bone plate) to help releasably attached the plate holder to the bone plate. In use, the clinician may engage one or more plate holders 480, such as at least two plate holders positioned on different side of the bone plate bridge that crosses the TMT joint, and use the plate holders to manipulate the position of the plate. Additionally or alternatively, the clinician may use the plate holders to bend the bone plate to a desired shape, e.g., specific to the anatomy of the patient undergoing the procedure. In some examples, incision guide 404 also functions as plate holder 480 and/or a plate bender.

Independent of the specific configuration of a plate holder may be operatively connected to a bone plate. The clinician may manipulate the plate holder and, correspondingly, bone plate, to insert the bone plate through incision 400 until the bone plate is positioned across the TMT joint with at least one fixation hole positioned over an underlying metatarsal and at least one fixation hole positioned over an underlying cuneiform. The clinician can then optionally drill a hole into each underlying bone portion through a bone plate fixation hole (e.g., via a drill guide), remove the drill guide, and then insert a screw to secure the bone plate to the underlying bone. In some examples, the clinician installs screws through fixation holes of the bone plate not attached to the plate holder then removes the plate holder and inserts screws through the remaining fixation holes.

In general, bone plate 100 may be planar (e.g., in the X-Z plane indicated on FIG. 17) or may include one or more bends or curves that position at least a portion of the bone plate out of plane with a reminder of the bone plate. For example, as illustrated in FIG. 17, the ends of the legs of the bone plate (e.g., through which fixation hole 112, 116 are positioned) may be out of plane with the base of the bone plate and/or base 104 may be curved such that fixation holes 114, 118 are out of plane with each other.

In some configurations, the curvature of the bone plate may direct drill guides inserted into adjacent pairs of fixation holes to be directed away from one another, e.g., to form a diverging angle relative to each other rather than a converging angle or be parallel to each other. This may be useful to allow the plate holder to be positioned against the outer surface of the diverging drill guide and help prevent the plate holder from inadvertently slipping off the drill guides.

As an additional feature, the handle and/or arms of the plate holder may be contoured (e.g., curved) out of plane from the proximal end (e.g., where the clinician's hand holds the instrument) to allow for easy placement against a metatarsal. For example, when so configured, the instrument may allow for the bone plate to be placed on the medial side of the metatarsal with the curvature of the instrument generally conforming to the curvature of the anatomy. This conformity can allow for minimal tissue retraction during plate placement.

Figure 22:
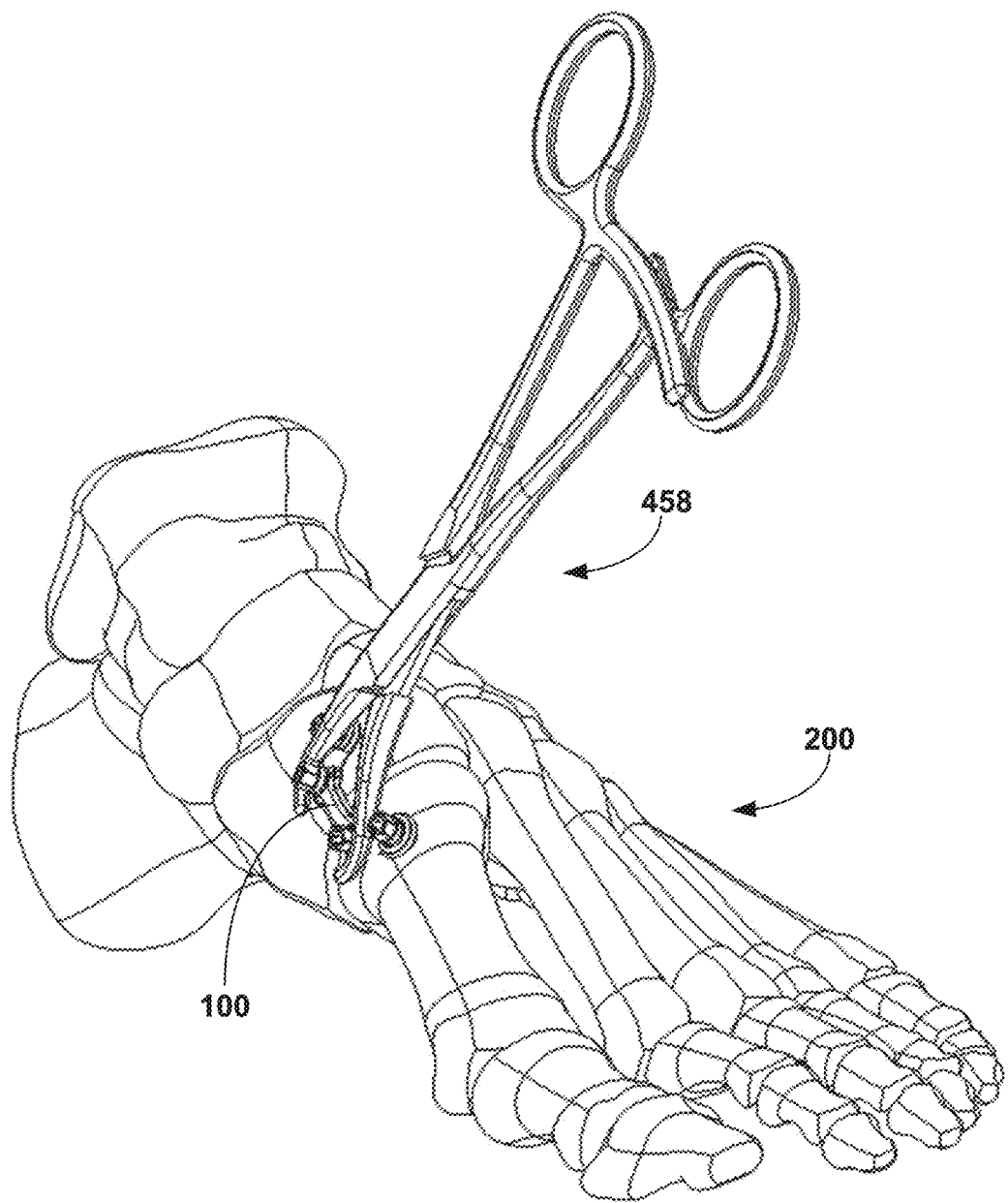
FIG. 22 is an illustration of a foot showing an example plate holder manipulating a plate for placement across a TMT joint.

FIG. 22 is an illustration of foot 200 showing an example of plate holder 458 manipulating plate 100 for placement across a TMT joint. While example plate holders have generally been described in conjunction with placement of a U-shaped plate, a plate holder may be releasably attached to, and used to position, a plate having a different configuration (e.g., a straight plate) in addition to or in lieu of a U-shaped plate.

Various examples have been described. These and other examples are within the scope of the following claims.

The invention claimed is:

1. A method of performing a minimal incision metatarsal correction procedure, the method comprising:
   preparing an end of a metatarsal;
   preparing an end of a cuneiform separated from the metatarsal by a tarsometatarsal joint;
   moving the metatarsal relative to the cuneiform using a bone positioning device comprising a metatarsal engagement member and a tip, the metatarsal engagement member being positioned in contact with a skin of a patient covering a medial side of the metatarsal and the tip being positioned on a lateral side of a different metatarsal, wherein moving the metatarsal comprises applying a force via the bone positioning device to the skin of the patient covering the medial side of the metatarsal to move the metatarsal in a transverse plane to close an intermetatarsal angle between the metatarsal and an adjacent metatarsal and to rotate the metatarsal in a frontal plane, the metatarsal rotating relative to the metatarsal engagement member; and
   after moving the metatarsal relative to the cuneiform, causing the metatarsal to fuse to the cuneiform.

2. The method of claim 1, further comprising:
making an incision between the different metatarsal and a laterally-adjacent metatarsal;
inserting the tip of the bone positioning device through the incision; and
positioning the tip in contact with the lateral side of a different metatarsal.

3. The method of claim 2, wherein:
the metatarsal is a first metatarsal;
the cuneiform is a medial cuneiform;
the different metatarsal is a second metatarsal; and
the laterally-adjacent metatarsal is a third metatarsal.

4. The method of claim 1, wherein the metatarsal engagement member defines a concave surface configured to contact the skin of the patient covering the medial side of the metatarsal, the concave surface is formed by a pair of sidewalls, and the metatarsal engagement member defines a length extending in a dorsal to plantar direction that is at least 28 mm.

5. The method of claim 1, wherein moving the metatarsal relative to the cuneiform using the bone positioning device comprises engaging a mechanism that moves the metatarsal engagement member and the tip relative to each other.

6. The method of claim 5, wherein the mechanism comprises at least one of a ratchet and a threaded shaft.

7. The method of claim 1, wherein causing the metatarsal to fuse to the cuneiform comprises installing at least one of a plate, a pin, a screw, and a staple across the tarsometatarsal joint between the metatarsal and the cuneiform.

8. The method of claim 1, wherein causing the metatarsal to fuse to the cuneiform comprises installing a U-shaped plate across the tarsometatarsal joint.

9. The method of claim 8, wherein the U-shaped plate comprises:
a first metatarsal-side fixation hole, a second metatarsal-side fixation hole, a first cuneiform-side fixation hole, and a second cuneiform-side fixation hole;
the first metatarsal-side fixation hole is spaced from the first cuneiform-side fixation hole by a bridge;
the second metatarsal-side fixation hole is angularly offset relative to the bridge; and
the second metatarsal-side fixation hole is angularly offset relative to the bridge.

10. The method of claim 9, wherein installing the U-shaped plate across the tarsometatarsal joint comprises positioning the bridge across the tarsometatarsal joint with the first metatarsal-side fixation hole and the first cuneiform-side fixation hole positioned plantarly relative to the second metatarsal-side fixation hole and the second cuneiform-side fixation hole.

11. The method of claim 8, wherein installing the U-shaped plate across the tarsometatarsal joint comprises installing the U-shaped plate on a medial side of the metatarsal and the cuneiform, and further comprising installing a second plate on a dorsal side of the metatarsal and the cuneiform.

12. The method of claim 1, wherein causing the metatarsal to fuse to the cuneiform comprises installing a plate across the tarsometatarsal joint, and further comprising attaching a plate holder to the plate and using the plate holder to position the plate over the metatarsal and the cuneiform while installing the plate.

13. The method of claim 12, wherein the plate holder comprises an instrument configured to at least one of grasp an external surface of the plate and be inserted into a fixation hole of the plate.

14. The method of claim 12, wherein the plate comprises a U-shaped plate that includes a first fixation hole with a first drill guide inserted into the first fixation hole and a second fixation hole with a second drill guide inserted into the second fixation hole, wherein the plate holder comprises a forceps with converging angled tips configured to be positioned against an external surface of the first drill guide and the second drill guide.

15. The method of claim 1, further comprising making an incision through the skin to access the tarsometatarsal joint between the metatarsal and the cuneiform, wherein the incision has a length less than 6 cm.

16. The method of claim 1, further comprising:
making an incision through the skin to access the tarsometatarsal joint between the metatarsal and the cuneiform, and
prior to making the incision, imaging at least a portion of the metatarsal and the cuneiform to identify a location of the tarsometatarsal joint.

17. The method of claim 16, further comprising positioning a radio-identifiable marking line on an incision guide on the location of the tarsometatarsal joint to designate an incision location.

18. The method of claim 1, wherein:
preparing the end of the metatarsal comprises preparing the end of the metatarsal with a bone preparation guide, and/or
preparing the end of the cuneiform comprises preparing the end of the cuneiform with the bone preparation guide.

19. The method of claim 18, wherein the bone preparation guide comprises at least one guide surface configured to be positioned over at least one of the metatarsal and the cuneiform.

20. The method of claim 19, wherein the at least one guide surface comprises a first guide surface configured to guide a cutting instrument across the metatarsal and a second guide surface configured to guide the cutting instrument across the medial cuneiform, and further comprising:
a first facing surface spaced from the first guide surface to define a first cutting slot between the first guide surface and the first facing surface, and
a second facing surface spaced from the second guide surface to define a second cutting slot between the second guide surface and the second facing surface.

21. The method of claim 18, further comprising attaching the bone preparation guide to at least one of the metatarsal and the cuneiform by inserting at least one fixation pin into at least one fixation pin receiving aperture of the bone preparation guide and into the at least one of the metatarsal and the cuneiform.

22. The method of claim 1, wherein:
preparing the end of the metatarsal comprises at least one of cutting and fenestrating the end of the metatarsal, and
preparing the end of the cuneiform comprises at least one of cutting and fenestrating the end of the cuneiform.

23. The method of claim 1, further comprising, after moving the metatarsal relative to the cuneiform and prior to causing the metatarsal to fuse to the cuneiform, provisionally fixating the position of the metatarsal relative to the cuneiform.

24. The method of claim 1, wherein the metatarsal is a first metatarsal and the cuneiform is a medial cuneiform.

* * * * *